United States Patent
Huang

(10) Patent No.: US 12,258,334 B2
(45) Date of Patent: Mar. 25, 2025

(54) BRANCHED SUGAR ALCOHOL-BASED COMPOUNDS, AND COMPOSITIONS AND METHODS THEREOF

(71) Applicant: CellMosaic Inc., Woburn, MA (US)

(72) Inventor: Yumei Huang, Lexington, MA (US)

(73) Assignee: CellMosaic Inc., Woburn, MA (US)

( * ) Notice: Subject to any disclaimer, the term of this patent is extended or adjusted under 35 U.S.C. 154(b) by 1056 days.

(21) Appl. No.: 17/045,286

(22) PCT Filed: Apr. 30, 2019

(86) PCT No.: PCT/US2019/029854
§ 371 (c)(1),
(2) Date: Oct. 5, 2020

(87) PCT Pub. No.: WO2019/213046
PCT Pub. Date: Nov. 7, 2019

(65) Prior Publication Data
US 2021/0170037 A1  Jun. 10, 2021

Related U.S. Application Data

(60) Provisional application No. 62/665,250, filed on May 1, 2018.

(51) Int. Cl.
| | | |
|---|---|---|
| C07D 405/14 | (2006.01) | |
| A61K 47/56 | (2017.01) | |
| A61K 47/68 | (2017.01) | |
| C08G 83/00 | (2006.01) | |

(52) U.S. Cl.
CPC ............ *C07D 405/14* (2013.01); *A61K 47/56* (2017.08); *A61K 47/68033* (2023.08); *A61K 47/68037* (2023.08); *A61K 47/6809* (2017.08); *C08G 83/003* (2013.01)

(58) Field of Classification Search
CPC .................. C07D 405/14; A61K 47/56; A61K 47/68033; A61K 47/68037; A61K 47/6809; C08G 83/003
See application file for complete search history.

(56) References Cited

PUBLICATIONS

Chemical Abstract Service STNext database, Registry No. 51580-45-1 [entered STN: Nov. 16, 1984]. (Year: 1984).*

* cited by examiner

*Primary Examiner* — Samantha L Shterengarts
*Assistant Examiner* — Sagar Patel
(74) *Attorney, Agent, or Firm* — Milstein Zhang & Wu LLC

(57) ABSTRACT

The invention provides novel sugar alcohol-based dendrimer-like molecules. These sugar alcohol-based molecules have multiple functional groups that can be used to label, conjugate, and immobilize large amounts of molecules or multiple types of molecules of interest for diagnostic, therapeutic, and research usage. Methods of synthesizing these sugar alcohol-based dendrimer-like molecules and conjugates are also within the scope of the invention.

19 Claims, No Drawings

BRANCHED SUGAR ALCOHOL-BASED COMPOUNDS, AND COMPOSITIONS AND METHODS THEREOF

PRIORITY CLAIMS AND RELATED APPLICATIONS

This application is the U.S. national phase of and claims priority to PCT/US2019/029854, filed Apr. 30, 2019, which claims the benefit of priority to U.S. Provisional Application No. 62/665,250, filed May 1, 2018.

FIELD OF THE INVENTION

The invention relates to novel sugar alcohol-based, dendrimer-like compounds and synthetic methods. More particularly, the invention provides novel chemical entities that are useful for labeling, conjugating, and immobilizing molecules of interest for diagnostic, therapeutic, and research usage. The invention also provides novel conjugates prepared using sugar alcohol-based dendrimer-like compounds.

BACKGROUND OF THE INVENTION

Hydrophilic linkers have been adapted by biochemists to modulate the properties of various molecules. Such linkers, which are available in different motifs, have been used as agents of drug delivery, aqueous solubility enhancers for hydrophobic molecules, tethers or spacers in conjugation, encapsulating molecules in nanotechnology, and in cosmetic formulations. Polyethylene glycol (PEG) is one of the most commonly used hydrophilic linkers. Lower molecular weight (MW) heterobifunctional PEG compounds are the most frequently used compounds for linking hydrophobic compounds.

However, in many cases, the hydrophilicity of PEG is not enough for some hydrophobic molecules to have sufficient solubility for biological applications. Thus, better hydrophilic linkers need to be developed.

A new type of hydrophilic crosslinking reagent based on sugar alcohol was described recently (U.S. Pat. Nos. 8,907,079B2, 9,511,150B2, WO2013/012961A2). These new chemicals are based on sugar alcohols and exhibit great promise for improved solubility for many hydrophobic molecules after modification and can be used to conjugate a variety of biomolecules for diverse applications.

There is an ongoing need for improved hydrophilic linkers and crosslinking reagents.

SUMMARY OF THE INVENTION

The invention provides bifurcated (e.g., branched or dendrimer-like) sugar alcohol (SA) molecules, their applications in conjugate preparation, and methods for synthesizing these dendrimer-like molecules. The invention is based, in part, on SAs with better hydrophilicity than PEG. The invention is also based, in part, on SAs that can be derivatized and modified to allow for the incorporation of various functional groups and activation groups. The invention is also based, in part, on SAs that can be further reacted with various other SAs to prepare branched or hyperbranched SA macromolecules with multiple crosslinking groups for high loading.

In one aspect, the invention generally relates to a bifurcated SA monomer having a chemical structure of Formula I:

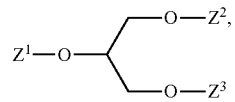

wherein
each of $Z^1$, $Z^2$, and $Z^3$ is independently selected from the group consisting of $R^{11}$ and

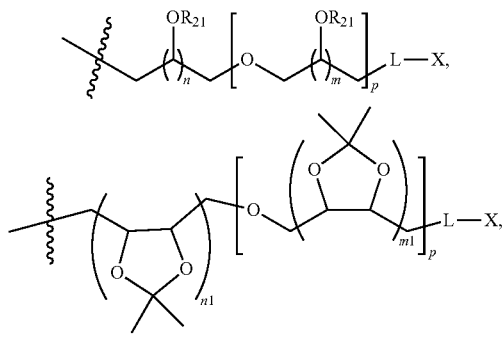

and at least one of $Z^1$, $Z^2$, and $Z^3$ is not $R^{11}$;

each $R^{11}$ is independently selected from the group consisting hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to about 8;
m is an integer selected from 1 to about 8;
p is an integer selected from 0 to about 50;
n1 is an integer selected from 1 to about 4;
m1 is an integer selected from 1 to about 4;
each L is independently selected from the group consisting of $R^2$ and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(=$G^2$)-$G^1$-, —S—S—, —S—$(CH_2)_2$—S($O)_2$—, —S($O)_2$—$(CH_2)_2$—S—, —S($O)_2$—N($R^3$)—, —N($R^3$)—S($O)_2$—, —C(O)—NH—NH—$CH_2$—, —C(O)—NH—N=CH—, —CH=N—NH—C(O)—, —$CH_2$—NH—NH—C(O)—, —N($R^3$)—S($O)_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—

$CH_2$—, -$G^4$—N=CH—, —C(—$NH_2^+$)—NH—, —NH—C(=$NH_2^+$)—, —O—P(=O)(O$^-$)—NH—, —NH—P(=O)(O$^-$)—O—, —$CH_2$—CH($NH_2$)—$CH_2$—S—, —S—$CH_2$—CH($NH_2$)—$CH_2$—, —O—P(=O)(O$^-$)—O—, —O—P(=O)(S$^-$)—O—, —O—P(=S)(S$^-$)—O—,

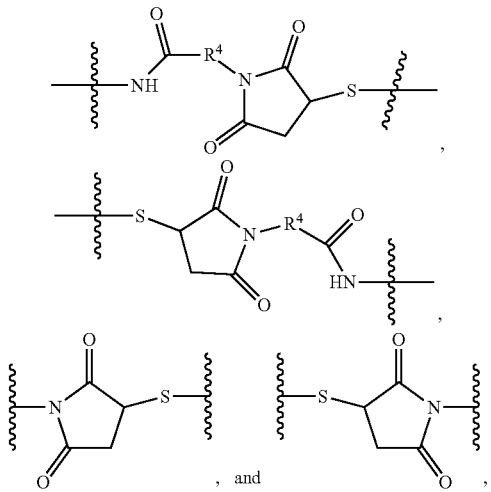

, and wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —($CH_2CH_2O$)$_{1-10}$—, —($CH_2CH_2O$)$_{1-10}$—$CH_2$—, —$CH_2$—(CHOH)$_{1-6}$—, —(CHOH)$_{1-6}$—$CH_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl, and
each $R^4$ is independently selected from $C_1$-$C_{16}$ alkyl,
each X is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —S(=O)$_2$-J, —NH—C(=O)—$R^9$—S—C(=O)—$R^5$, —$NH_2$, —$NHR^5$, —N($R^5$) $R^5$, —$NHR^7$, —NH-Fmoc, —NH-Boc, N-(phthalimidyl), —C(=O) H, —C(=O)—$R^5$, —NH—C(=O)—$R^9$—C(=O)—$R^5$, —C(=O)OH, NH—C(=O)—$R^9$—C(=O)OH, —N=C=S, —N=C=O, —C≡C—$R^5$, —N=N$^+$=N$^-$, —O—$NH_2$, —O—NH-Fmoc, —O—NH-Boc, —O—N-(Boc)$_2$, —O—N(-phthalimidyl), —NH—C(=O)—$R^9$—O—NH-Boc, —NH—C(=O)—$R^9$—O—N-(Boc)$_2$, NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluene-sulfonylhydrazide, —$R^5$—NH—C(=$NH_2^+$)—$NH_2$, —NH—C(=$NH_2^+$)—$CH_2CH_2CH_2$—SH,

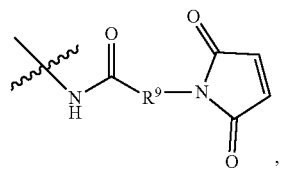

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=N$^+$H$_2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group,
wherein
each $R^5$ is independently selected from hydrogen, $C_1$-$C_8$ alkyl, alicyclyl, heteroalicyclyl, benzyl, or aryl, wherein any ring in $R^5$ is optionally substituted;
each $R^6$ is independently selected from benzoyl, acetyl, benzyl, $C_1$-$C_8$ alkyl silyl, tetrahydropyranyl, tetrahydrofuranyl, and tetrahydrothiofuranyl;
each $R^7$ is independently selected from trityl, MMT, and DMT;
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each $R^9$ is independently selected from $C_1$-$C_{16}$ alkyl; and
each J is independently selected from Cl, Br and I.

In another aspect, the invention generally relates to a solid phase linked compound comprising one bifurcated SA monomer unit, wherein the bifurcated SA monomer has the chemical structure Formula I:

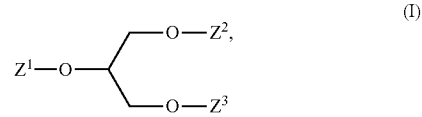

(I)

wherein the bifurcated SA monomer is bound to the solid phase through a linking group, W, formed by a reaction between the X group of the $Z^1$ unit and the functional group on the solid phase,
wherein
the solid phase is a commercial polystyrene resin that functioned with any of the following functional group: 4-benzyloxybenzyl alcohol, trityl alcohol, 2-chlorotrityl chloride, trityl chloride, 4-methyltrityl chloride, 4-methoxytrityl chloride, 4-(4-hydroxymethyl-3-methoxyphenoxy) butyryl MBHA, 4-(2'4'-dimethoxyphenylhydroxymethyl) phenoxy, 4-(4-hydroxymethyl-3-methoxyphenoxy) butyryl BHA, 4-hydroymethylbenzoyl MBHA, 4-(4-hydroxymethyl-3-methoxyphenoxy) butyryl MBHA, HMBA AM, TentaGel S PHB, Tentagel S HMBA, 4-hydroxymethylphenoxyacetyl AM, alcohol, ketone, amine, aminomethyl, carbonate, carboxylic acid, thiol, photocleavable;

each of $Z^1$, $Z^2$, and $Z^3$ is independently selected from the group consisting of $R^{11}$ and

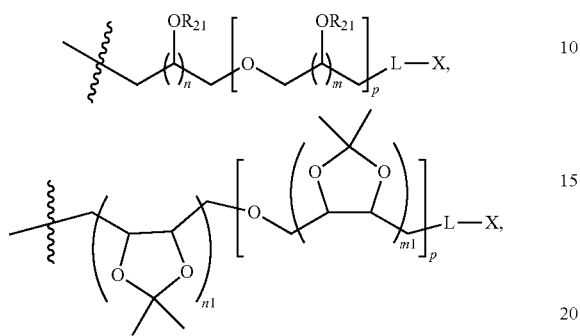

and at least one of $Z^1$, $Z^2$, and $Z^3$ is not $R^{11}$;

each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R_{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to about 8;
m is an integer selected from 1 to about 8;
p is an integer selected from 0 to about 50;
n1 is an integer selected from 1 to about 4;
m1 is an integer selected from 1 to about 4;

each L and W is independently selected from the group consisting of $R^2$ and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(=$G^2$)-$G^1$-, —S—S—, —S—$(CH_2)_2$—$S(O)_2$—, —$S(O)_2$—$(CH_2)_2$—S—, —$S(O)_2$—N($R^3$)—, —N($R^3$)—$S(O)_2$—, —C(O)—NH—NH—$CH_2$—, —C(O)—NH—N=CH—, —CH=N—NH—C(O)—, —$CH_2$—NH—NH—C(O)—, —N($R^3$)—$S(O)_2$—N($R^3$)—, —C(O)—NH—CH($CH_2SH$)—, —N=CH—, —NH—$CH_2$—, —NH—C(O)—$CH_2$—C(O)—NH—, —$CH_2$—$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

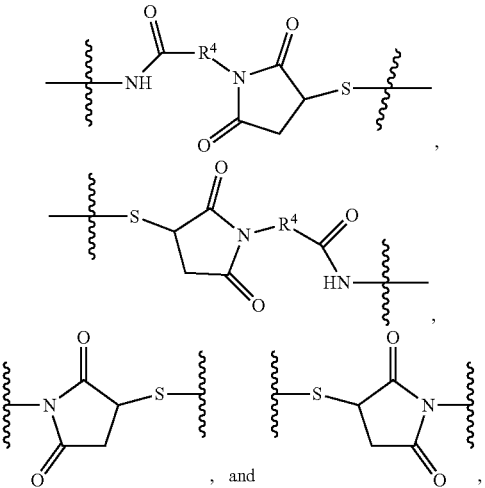

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —$(CH_2CH_2O)_{1-10}$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —$(OCH_2CH_2)_{1-3}$, optionally substituted alicyclyl, and optionally substituted heteroalicyclyl,
each $R^4$ is independently selected from $C_1$-$C_{16}$ alkyl;
each X is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —$S(=O)_2$-J, —NH—C(=O)—$R^9$—S—C(=O)—$R^5$, —$NH_2$, —$NHR^5$, —N($R^5$) $R^5$, —$NHR^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=$N^+$=$N^-$, —O—$NH_2$, —O—NH-Fmoc, —O—NH-Boc, —O—N-$(Boc)_2$, —O—N(-phthalimidyl), —NH—C(=O)—$R^9$—O—NH-Boc, —NH—C(=O)—$R^9$—O—N-$(Boc)_2$, —NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, —NH—C(=$NH_2^+$)—$CH_2CH_2CH_2$—SH,

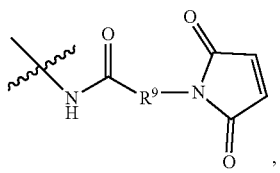

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C($=$N$^+$H$_2$)—O—R$^5$, a hydroxymethyl phosphine derivative, an ethyl vinyl, a maleimide, a vinylsulfone, an allyl sulfone, a thioester, a cisplatin derivative, an aziridine, an acryloyl group;

wherein each R$^5$ is independently selected from hydrogen, C$_1$-C$_8$ alkyl, alicyclyl, heteroalicyclyl, benzyl, or aryl, wherein any ring in R$^5$ is optionally substituted;

each R$^6$ is independently selected from benzoyl, acetyl, benzyl, C$_1$-C$_8$ alkyl silyl, tetrahydropyranyl, tetrahydrofuranyl, and tetrahydrothiofuranyl;

each R$^7$ is independently selected from trityl, MMT, and DMT;

each R$^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each R$^9$ is independently selected from C$_1$-C$_{16}$ alkyl; and each J is independently selected from Cl, Br and I.

In yet another aspect, the invention generally relates to a dendrimer-like SA molecule comprising two or more bifurcated SA monomer units, B$_1$, wherein each B$_1$ has the chemical structure Formula I:

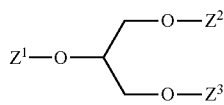

(I)

and each B$_1$ unit is bound to one or more other monomeric units through a linking group, W, formed by a reaction between the X group of the Z$^1$ unit and the X group of the Z$^2$ or Z$^3$ unit;

wherein each of Z$^1$, Z$^2$, and Z$^3$ is independently selected from the group consisting of R$^{11}$ and

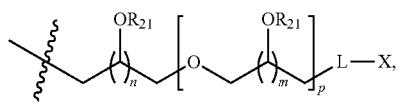

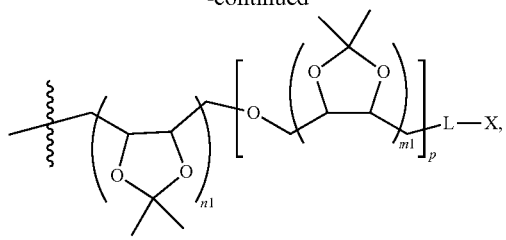

and at least one of Z$^1$, Z$^2$, and Z$^3$ is not R$^{11}$;

each R$^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, C$_1$-C$_8$ alkyl silyl, methyl ethers, and ethoxyethyl ethers;

R$^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, C$_1$-C$_8$ alkyl silyl, methyl ethers, ethoxyethyl ethers, C$_1$-C$_8$ alkyl, cyclic ortho ester, acetonide of vicinal alcohol;

n is an integer selected from 2 to about 8;

m is an integer selected from 1 to about 8;

p is an integer selected from 0 to about 50;

n1 is an integer selected from 1 to about 4;

m1 is an integer selected from 1 to about 4;

each L and W is independently selected from the group consisting of a bond, R$^2$, and a structure of —V$_1$—R$^2$—V$_2$—, wherein V$_1$, and V$_2$ are independently selected from the group consisting of a Diels-Alder adduct, a 1,3-dipolar adduct, —C(R$^4$)($=$N)—O—, —O—C(R$^4$)($=$N)—, —S—CH$_2$—C($=$O)—NH—, —NH—C($=$O)—CH$_2$—S—, —C($=$G$^2$)-G$^1$-, -G$^1$-C($=$G$^2$)-, -G$^3$-, -G$^1$-C(-G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N$=$CH—, —CH$=$N—NH—C(O)—, —CH$_2$—NH—NH—C(O)—, —N(R$^3$)—S(O)$_2$—N(R$^3$)—, —C(O)—NH—CH(CH$_2$SH)—, —N$=$CH—, —NH—CH$_2$—, —NH—C(O)—CH$_2$—C(O)—NH—, —CH$=$N-G$^4$-, —CH$_2$—NH-G$^4$-, -G$^4$-NH—CH$_2$—, -G$^4$-N$=$CH—, —C($=$NH$_2^+$)—NH—, —NH—C($=$NH$_2^+$)—, —O—P($=$O)(O$^-$)—NH—, —NH—P($=$O)(O$^-$)—O—, —CH$_2$—CH(NH$_2$)—CH$_2$—S—, —S—CH$_2$—CH(NH$_2$)—CH$_2$—, —O—P($=$O)(O$^-$)—O—, —O—P($=$O)(S$^-$)—O—, —O—P($=$S)(S$^-$)—O—,

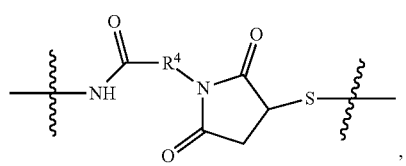

-continued

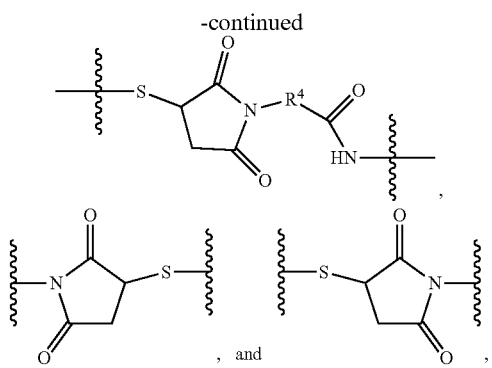, and wherein
 each $G^1$ is independently selected from $NR^3$, O, and S;
 each $G^2$ is independently O or S;
 each $G^3$ is independently selected from S, O, $NR^3$, and $SO_2$;
 each $G^4$ is independently O or $NR^3$;
 each $R^2$ is independently selected from a bond, $C_1$-$C_{12}$ alkyl, —$(CH_2CH_2O)_{1-10}$—, —$(CH_2CH_2O)_{1-10}$—$CH_2$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
 each $R^3$ is independently selected from hydrogen, $C_1$-$C_8$ alkyl, —$(OCH_2CH_2)_{1-3}$, optionally substituted alicyclyl, and optionally substituted heteroalicyclyl,
 each $R^4$ is independently selected from $C_1$-$C_{16}$ alkyl;
 each X is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —S(=O)$_2$-J, —NH—C(=O)—$R^9$—S—C(=O)—$R^5$, —$NH_2$, —$NHR^5$, —$N(R^5)$ $R^5$, —$NHR^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=$N^+$=$N^-$, —O—$NH_2$, —O—NH-Fmoc, —O—NH-Boc, —O—N-$(Boc)_2$, —O—N(-phthalimidyl), —NH—C(=O)—$R^9$—O—NH-Boc, —NH—C(=O)—$R^9$—O—N-$(Boc)_2$, NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, —NH—C(=$NH_2^+$)—$CH_2CH_2CH_2$—SH,

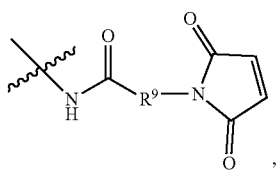

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$N^+$$H_2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;
 each $R^5$ is independently selected from hydrogen, $C_1$-$C_8$ alkyl, alicyclyl, heteroalicyclyl, benzyl or aryl, wherein any ring in $R^5$ is optionally substituted;
 each $R^6$ is independently selected from benzoyl, acetyl, benzyl, $C_1$-$C_8$ alkyl silyl, tetrahydropyranyl, tetrahydrofuranyl, and tetrahydrothiofuranyl;
 each $R^7$ is independently selected from trityl, MMT, and DMT;
 each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
 each $R^9$ is independently selected from $C_1$-$C_{16}$ alkyl; and
 each J is independently selected from Cl, Br, and I.

In yet another aspect, the invention generally relates to a conjugate formed by a reaction of a molecule ($M_1$) with the X group of $Z^1$ of a bifurcated monomer unit $B_1$ or a dendrimer-like SA molecule B comprising two or more bifurcated monomer units $B_1$, wherein the conjugate has a chemical structure Formula (III) or (IV):

$$M_1\text{-}(L_2\text{-}B_1)_r \quad \text{(III) or}$$

$$M_1\text{-}(L_2\text{-}B)_r \quad \text{(IV),}$$

wherein
 each $M_1$ is independently selected from the group consisting of a solid support, a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;
 r is an integer selected from 1 to about 50;
 $L_2$ is a linking group that formed by a reaction of $M_1$ with the X group of $Z^1$ and is independently selected from the group consisting of $R^{22}$ and a structure of —$V_{11}$—$R^{22}$—$V_{22}$—, wherein $V_{11}$ and $V_{22}$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(-$G^2$)-$G^1$-, —S—S—, —S—$(CH_2)_2$—$S(O)_2$—, —$S(O)_2$—$(CH_2)_2$—S—, —$S(O)_2$—$N(R^3)$—, —$N(R^3)$—$S(O)_2$—, —C(O)—NH—NH—$CH_2$—, —C(O)—NH—N=CH—, —CH=N—NH—C(O)—, —$CH_2$—NH—NH—C(O)—, —$N(R^3)$—$S(O)_2$—$N(R^3)$—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

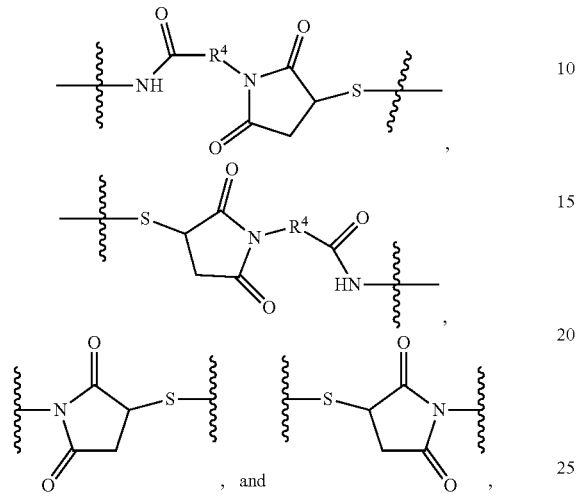

wherein
each G$^1$ is independently selected from NR$^3$, O, and S;
each G$^2$ is independently O or S;
each G$^3$ is independently selected from S, O, NR$^3$, and SO$_2$;
each G$^4$ is independently O or NR$^3$;
each R$^{22}$ is independently selected from a bond, C$_1$-C$_{12}$ alkyl, —(CH$_2$CH$_2$O)$_{1-10}$—, —(CH$_2$CH$_2$O)$_{1-10}$—CH$_2$—, —CH$_2$—(CHOH)$_{1-6}$—, —CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each R$^3$ is independently selected from hydrogen, C$_1$-C$_8$ alkyl, —(OCH$_2$CH$_2$)$_{1-3}$, optionally substituted alicyclyl, and optionally substituted heteroalicyclyl;
each R$^4$ is independently selected from C$_1$-C$_{16}$ alkyl; and
each B comprising two or more bifurcated SA monomer units B$_1$, wherein each B$_1$ has the chemical structure Formula I:

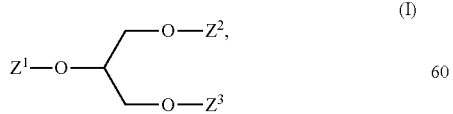
(I)

and each B$_1$ unit is bound to one or more other monomeric units through a linking group, W, formed by a reaction between the X group of the Z$^1$ unit and the X group of the Z$^2$ or Z$^3$ unit;

wherein
each of Z$^1$, Z$^2$, and Z$^3$ is independently

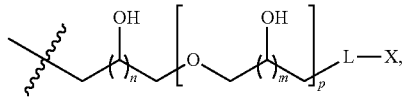

wherein
n is an integer selected from 2 to about 8;
m is an integer selected from 1 to about 8;
p is an integer selected from 0 to about 4;
each L and W is independently selected from the group consisting of a bond, R$^2$, and a structure of —V$_1$—R$^2$—V$_2$—, wherein V$_1$, and V$_2$ are independently selected from the group consisting of a Diels-Alder adduct, a 1,3-dipolar adduct, —C(R$^4$)(=N)—O—, —O—C(R$^4$)(=N)—, —S—CH$_2$—C(=O)—NH—, —NH—C(=O)—CH$_2$—S, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

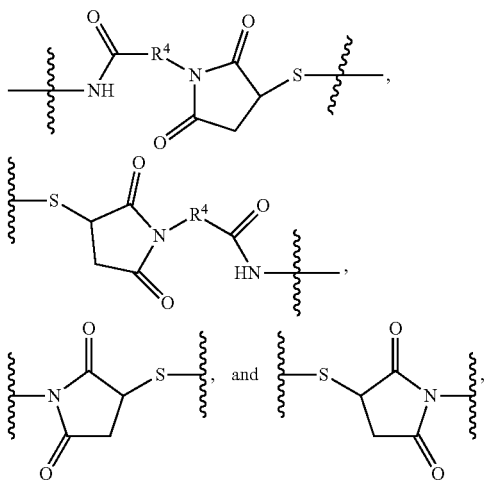

wherein
each G$^1$ is independently selected from NR$^3$, O, and S;
each G$^2$ is independently O or S;
each G$^3$ is independently selected from S, O, NR$^3$, and SO$_2$;
each G$^4$ is independently O or NR$^3$;
each R$^2$ is independently selected from a bond, C$_1$-C$_{12}$ alkyl, —(CH$_2$CH$_2$O)$_{1-10}$—, —(CH$_2$CH$_2$O)$_{1-10}$—CH$_2$—, —(CH$_2$CH$_2$O)$_{1-10}$—CH$_2$—, —CH$_2$—

—(CHOH)$_{1-6}$—, —(CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl, each $R^4$ is independently selected from $C_1$-$C_{16}$ alkyl, each X is independently selected from —OH, -J, —R$^5$J, —C(=O)-J, —C(=O)—CH$_2$-J, —NH—C(=O)—CH$_2$-J, —OR$^5$, —OR$^6$, —OR$^7$, —O-mesyl, —O-tosyl, —NH—C(=O)—CH$_2$—O-mesyl, —NH—C(=O)—CH$_2$—O-tosyl, —SH, —S—S-t-butyl, —SR$^7$, —SR$^5$, —S—S—R$^8$, —NH—C(=O)—R$^9$—S—S—R$^8$, —NH—C(=O)—CH$_2$—SH, —S(=O)$_2$-J, —NH—C(=O)—R$^9$—S—C(=O)—R$^5$, —NH$_2$, —NHR$^5$, —N(R$^5$) R$^5$, —NHR$^7$, —NH-Fmoc, —NH-Boc, N-(phthalimidyl), —C(=O) H, —C(=O)—R$^5$, NH—C(=O)—R$^9$—C(=O)—R$^5$, —C(=O)OH, NH—C(=O)—R$^9$—C(=O)OH, —N=C=S, —N=C=O, —C≡C—R$^5$, —N=N$^+$=N$^-$, —O—NH$_2$, —O—NH-Fmoc, —O—NH-Boc, —O—N-(Boc)$_2$, —O—N(-phthalimidyl), —NH—C(=O)—R$^9$—O—NH-Boc, —NH—C(=O)—R$^9$—O—N-(Boc)$_2$, —NH—C(=O)—R$^9$—O—N(-phthalimidyl), —NH—NH$_2$, —C(=O)—NH—NH$_2$, —NH—C(=O)—NH—NH$_2$, —NH—C(=S)—NH—NH$_2$, -toluene-sulfonylhydrazide, —R$^5$—NH—C(=NH$_2^+$)—NH$_2$, —NH—C(=NH$_2^+$)—CH$_2$CH$_2$CH$_2$—SH,

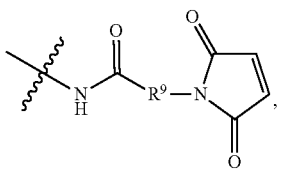

a diazirine, an optionally substituted trifluoromethylphenyldiazirine, an azide, an ester, a carbonate group, an ethyl vinyl, a maleimide, a vinylsulfone, an allyl sulfone, a thioester, an aziridine, each $R^5$ is independently selected from hydrogen, $C_1$-$C_8$ alkyl, alicyclyl, heteroalicyclyl, benzyl, or aryl, wherein any ring in $R^5$ is optionally substituted;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^9$ is independently selected from $C_1$-$C_{16}$ alkyl; and each J is independently selected from Cl, Br, and I.

In yet another aspect, the invention generally relates to a conjugate has a chemical structure Formula (V) or (VI):

$$B\text{-}(L_1\text{-}M_2)_q \quad \text{(V)}$$

$$B_1\text{-}(L_1\text{-}M_2)_q \quad \text{(VI)},$$

wherein the conjugate is formed by a reaction of one or several molecules (M$_2$) with one or several X groups of any of the $Z^2$ and $Z^3$ of a bifurcated SA monomer B$_1$ or a dendrimer-like SA molecule B comprising two or more bifurcated SA monomer units B$_1$, wherein each M$_2$ is independently selected from the group consisting of a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;

q is an integer selected from 1 to about 50;

each $L_1$ is independently selected from the group consisting of $R^{22}$ and a structure of —V$_{11}$—R$^{22}$—V$_{22}$—, wherein V$_{11}$ and V$_{22}$ are independently selected from the group consisting of a Diels-Alder adduct, a 1,3-dipolar adduct, —C(R$^4$)(=N)—O—, —O—C(R$^4$)(=N)—, —S—CH$_2$—C(=O)—NH—, —NH—C(=O)—CH$_2$—S—, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N—CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

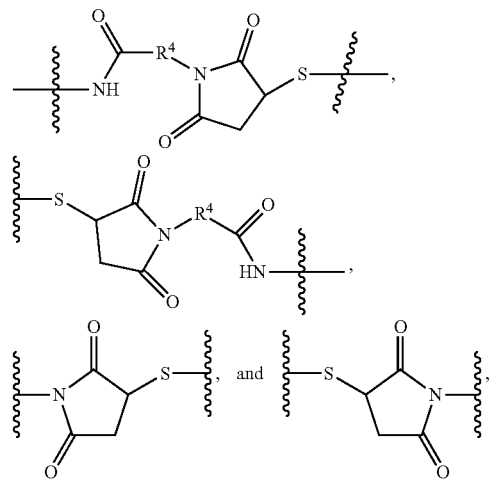

wherein each G$^1$ is independently selected from NR$^3$, O, and S;

each G$^2$ is independently O or S;

each G$^3$ is independently selected from S, O, NR$^3$, and SO$_2$;

each G$^4$ is independently O or NR$^3$;

each $R^{22}$ is independently selected from a bond, $C_1$-$C_{12}$ alkyl, —$(CH_2CH_2O)_{1-10}$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —$(OCH_2CH_2)_{1-3}$, optionally substituted alicyclyl, and optionally substituted heteroalicyclyl;

each $R^4$ is independently selected from $C_1$-$C_{16}$ alkyl; and each B comprising two or more bifurcated SA monomer units $B_1$, wherein each $B_1$ has the chemical structure Formula I:

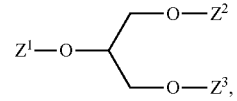

(I)

and each $B_1$ unit is bound to one or more other monomeric units through a linking group, W, formed by a reaction between the X group of the $Z^1$ unit and the X group of the $Z^2$ or $Z^3$ unit;

wherein each of $Z^1$, $Z^2$, and $Z^3$ is independently

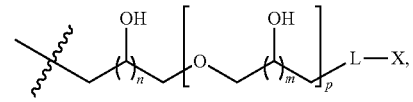

wherein
n is an integer selected from 2 to about 8;
m is an integer selected from 1 to about 8;
p is an integer selected from 0 to about 4;
each L and W is independently selected from the group consisting of a bond, $R^2$, and a structure of —$V_1$—$R^2$—$V_2$—, wherein $V_1$ and $V_2$ are independently selected from the group consisting of a Diels-Alder adduct, a 1,3-dipolar adduct, —$C(R^4)$(=N)—O—, —O—$C(R^4)$(=N)—, —S—$CH_2$—$C$(=O)—NH—, —NH—$C$(=O)—$CH_2$—S, —$C$(=$G^2$)-$G^1$-, -$G^1$-$C$(=$G^2$)-, -$G^3$-, -$G^1$-$C$(=$G^2$)-$G^1$-, —S—S—, —S—$(CH_2)_2$—$S(O)_2$—, —S(O)_2$—$(CH_2)_2$—S—, —$S(O)_2$—$N(R^3)$—, —$N(R^3)$—$S(O)_2$—, —$C(O)$—NH—NH—$CH_2$—, —$C(O)$—NH—N=CH—, —CH=N—NH—$C(O)$—, —$CH_2$—NH—NH—$C(O)$—, —$N(R^3)$—$S(O)_2$—$N(R^3)$—, —$C(O)$—NH—CH($CH_2SH$)—, —N=CH—, —NH—$CH_2$—, —NH—$C(O)$—$CH_2$—$C(O)$—NH—, —CH=N-$G^4$-, —$CH_2$—NH-$G^4$-, -$G^4$-NH—$CH_2$—, -$G^4$-N=CH—, —$C$(=$NH_2^+$)—NH—, —NH—$C$(=$NH_2^+$)—, —O—$P$(=O)($O^-$)—NH—, —NH—$P$(=O)(O)—O—, —$CH_2$—CH($NH_2$)—$CH_2$—S—, —S—$CH_2$—CH($NH_2$)—$CH_2$—, —O—$P$(=O)($O^-$)—O—, —O—$P$(=O)($S^-$)—O—, —O—$P$(=S)($S^-$)—O—,

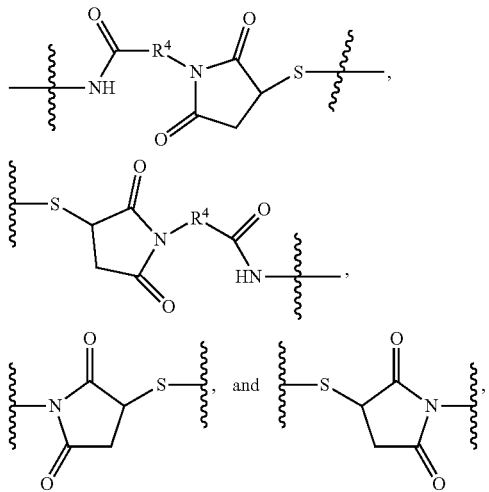

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —$(CH_2CH_2O)_{1-10}$—, —$(CH_2CH_2O)_{1-10}$—$CH_2$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —$(OCH_2CH_2)_{1-3}$, optionally substituted alicyclyl, and optionally substituted heteroalicyclyl,
each $R^4$ is independently selected from $C_1$-$C_{16}$ alkyl;
each X is independently selected from —OH, -J, —$R^5$J, —$C$(=O)-J, —$C$(=O)—$CH_2$-J, —NH—$C$(=O)—$CH_2$-J, —$OR^5$, —$OR^6$, —$OR^7$, —O-mesyl, —O-tosyl, —NH—$C$(=O)—$CH_2$—O-mesyl, —NH—$C$(=O)—$CH_2$—O-tosyl, —SH, —S—S-t-butyl, —$SR^7$, —$SR^5$, —S—S—$R^8$, —NH—$C$(=O)—$R^9$—S—S—$R^8$, —NH—$C$(=O)—$CH_2$—SH, —$S$(=O)$_2$-J, —NH—$C$(=O)—$R^9$—S—$C$(=O)—$R^5$, —$NH_2$, —$NHR^5$, —$N(R^5)$ $R^5$, —$NHR^7$, —NH-Fmoc, —NH-Boc, N-(phthalimidyl), —$C$(=O) H, —$C$(=O)—$R^5$, NH—$C$(=O)—$R^9$—$C$(=O)—$R^5$, —$C$(=O)OH, NH—$C$(=O)—$R^9$—$C$(=O)OH, —N=C=S, —N=C=O, —C≡C—$R^5$, —N=$N^+$=$N^-$, —O—$NH_2$, —O—NH-Fmoc, —O—NH-Boc, —O—N-(Boc)$_2$, —O—N(-phthalimidyl), —NH—$C$(=O)—$R^9$—O—NH-Boc, —NH—$C$(=O)—$R^9$—O—N-(Boc)$_2$, NH—$C$(=O)—$R^9$—O—N(-phthalimidyl), —NH—$NH_2$, —$C$(=O)—NH—$NH_2$, —NH—$C$(=O)—NH—$NH_2$, —NH—$C$(=S)—NH—$NH_2$, -toluenesulfonylhydrazide, —$R^5$—NH—$C$(=$NH_2^+$)—$NH_2$, —NH—$C$(=$NH_2^+$)—$CH_2CH_2CH_2$—SH,

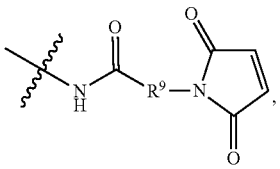

a diazirine, an optionally substituted trifluoromethylphenyldiazirine, an azide, an ester, a carbonate group, an ethyl vinyl, a maleimide, a vinylsulfone, an allyl sulfone, a thioester, an aziridine, each $R^5$ is independently selected from hydrogen, $C_1$-$C_8$ alkyl, alicyclyl, heteroalicyclyl, benzyl, or aryl, wherein any ring in $R^5$ is optionally substituted;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^9$ is independently selected from $C_1$-$C_{16}$ alkyl; and each J is independently selected from Cl, Br, and I.

In yet another aspect, the invention generally relates to a conjugate having a chemical structure Formula (VII) or (VIII):

$$M_1\text{-}(L_1\text{-}B_1\text{-}(L_1\text{-}M_2)q)r \quad \text{(VII), or}$$

$$M_1\text{-}(L_1\text{-}B\text{-}(L_1\text{-}M_2)q)r \quad \text{(VIII)}$$

wherein the conjugate is formed by a reaction of a molecule ($M_1$) with the X group of $Z^1$ of a bifurcated SA monomer unit $B_1$ or a dendrimer-like SA molecule B comprising two or more bifurcated SA monomer units $B_1$ and a reaction of one or several molecules ($M_2$) with one or several X groups of any of the $Z^2$ and $Z^3$ of a bifurcated SA monomer unit $B_1$ or a dendrimer-like SA molecule B comprising two or more bifurcated SA monomer units $B_1$, wherein q is an integer selected from 1 to about 50;

r is an integer selected from 1 to about 50;

each $M_1$ is independently selected from the group consisting of a solid support, a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;

each $M_2$ is independently selected from the group consisting of a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;

each $L_1$ is independently selected from the group consisting of $R^{22}$ and a structure of —$V_{11}$—$R^{22}$—$V_{22}$—, wherein $V_{11}$ and $V_{22}$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S, —C(=$G^2$)-$G^1$-, -$G^1$-C(=$G^2$)-, -$G^3$-, -$G^1$-C(=$G^2$)-$G^1$-, —S—S—, —S—$(CH_2)_2$—$S(O)_2$—, —$S(O)_2$—$(CH_2)_2$—S—, —$S(O)_2$—N($R^3$)—, —N($R^3$)—$S(O)_2$—, —C(O)—NH—NH—$CH_2$—, —C(O)—NH—N—CH—, —CH=N—NH—C(O)—, —$CH_2$—NH—NH—C(O)—, —N($R^3$)—$S(O)_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)(O)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

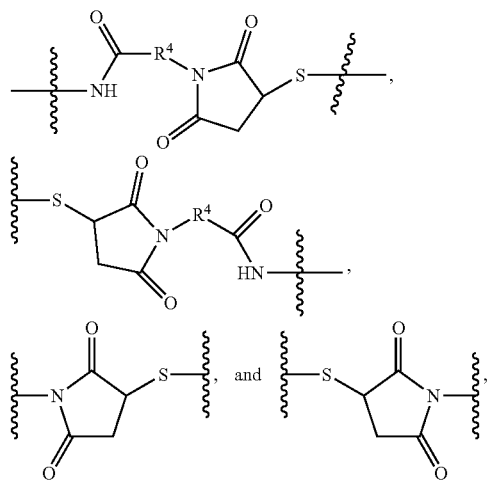

wherein each $G^1$ is independently selected from $NR^3$, O, and S;

each $G^2$ is independently O or S;

each $G^3$ is independently selected from S, O, $NR^3$, and $SO_2$;

each $G^4$ is independently O or $NR^3$;

each $R^{22}$ is independently selected from a bond, $C_1$-$C_{12}$ alkyl, —$(CH_2CH_2O)_{1-10}$—, $(CH_2CH_2O)_{1-10}$—$CH_2$—, —$CH_2$—$(CHOH)_{1-6}$—, —$CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —$(OCH_2CH_2)_{1-3}$, optionally substituted alicyclyl, and optionally substituted heteroalicyclyl;

each $R^4$ is independently selected from $C_1$-$C_{16}$ alkyl; and each B comprising two or more bifurcated SA monomer units $B_1$, wherein each $B_1$ has the chemical structure Formula I:

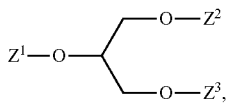

(I)

and each $B_1$ unit is bound to one or more other monomeric units through a linking group, W, formed by a reaction between the X group of the $Z^1$ unit and the X group of the $Z^2$ or $Z^3$ unit;

wherein each of $Z^1$, $Z^2$, and $Z^3$ is independently

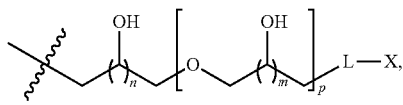

wherein n is an integer selected from 2 to about 8;

m is an integer selected from 1 to about 8;

p is an integer selected from 0 to about 4;

each L and W is independently selected from the group consisting of a bond, $R^2$, and a structure of $-V_1-R^2-V_2-$, wherein $V_1$ and $V_2$ are independently selected from the group consisting of a Diels-Alder adduct, a 1,3-dipolar adduct, $-C(R^4)$ $(=N)-O-$, $-O-C(R^4)(=N)-$, $-S-CH_2-$ $C(=O)-NH-$, $-NH-C(=O)-CH_2-S-$, $-C(=G^2)-G^1-$, $-G^1-C(=G^2)-$, $-G^3-$, $-G^1-C(=G^2)-$ $G^1-$, $-S-S-$, $-S-(CH_2)_2-S(O)_2-$, $-S(O)_2-(CH_2)_2-S-$, $-S(O)_2-N(R^3)-$, $-N(R^3)-S(O)_2-$, $-C(O)-NH-NH-$ $CH_2-$, $-C(O)-NH-N=CH-$, $-CH=N-$ $NH-C(O)-$, $-CH_2-NH-NH-C(O)-$, $-N(R^3)-S(O)_2-N(R^3)-$, $-C(O)-NH-CH$ $(CH_2SH)-$, $-N=CH-$, $-NH-CH_2-$, $-NH-C(O)-CH_2-C(O)-NH-$, $-CH=N-$ $G^4-$, $-CH_2-NH-G^4-$, $-G^4-NH-CH_2-$, $-G^4-$ $N=CH-$, $-C(=NH_2^+)-NH-$, $-NH-C$ $(=NH_2^+)-$, $-O-P(=O)(O^-)-NH-$, $-NH-P(=O)(O^-)-O-$, $-CH_2-CH$ $(NH_2)-CH_2-S-$, $-S-CH_2-CH(NH_2)-$ $CH_2-$, $-O-P(=O)(O^-)-O-$, $-O-P(=O)$ $(S^-)-O-$, $-O-P(=S)(S^-)-O-$,

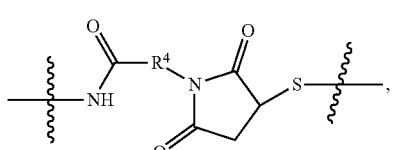

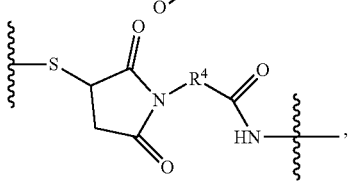

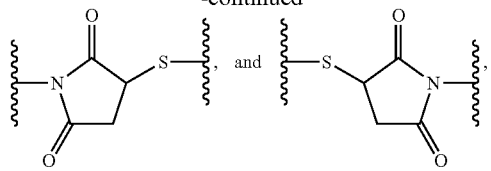

wherein each $G^1$ is independently selected from $NR^3$, O, and S;

each $G^2$ is independently O or S;

each $G^3$ is independently selected from S, O, $NR^3$, and $SO_2$;

each $G^4$ is independently O or $NR^3$;

each $R^2$ is independently selected from a bond, $C_1$-$C_{12}$ alkyl, $-(CH_2CH_2O)_{1-10}-$, $-(CH_2CH_2O)_{1-10}-$ $CH_2-$, $-(CH_2CH_2O)_{1-10}-CH_2-$, $-CH_2-$ $(CHOH)_{1-6}-$, $-(CHOH)_{1-6}-CH_2-$, $-(CHOH)_{1-6}-$, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, $-(OCH_2CH_2)_{1-3}$, optionally substituted alicyclyl, and optionally substituted heteroalicyclyl, each $R^4$ is independently selected from $C_1$-$C_{16}$ alkyl; and each X is independently selected from $-OH$, $-J$, $-R^5J$, $-C(=O)-J$, $-C(=O)-CH_2-J$, $-NH-C(=O)-$ $CH_2-J$, $-OR^5$, $-OR^6$, $-OR^7$, $-O$-mesyl, $-O$-tosyl, $-NH-C(=O)-CH_2-O$-mesyl, $-NH-C(=O)-$ $CH_2-O$-tosyl, $-SH$, $-S-S$-t-butyl, $-SR^7$, $-SR^5$, $-S-S-R^8$, $-NH-C(=O)-R^9-S-S-R^8$, $-NH-C(=O)-CH_2-SH$, $-S(=O)_2-J$, $-NH-C$ $(=O)-R^9-S-C(=O)-R^5$, $-NH_2$, $-NHR^5$, $-N(R^5)\ R^5$, $-NHR^7$, $-NH$-Fmoc, $-NH$-Boc, N-(phthalimidyl), $-C(=O)\ H$, $-C(=O)-R^5$, $NH-C(=O)-R^9-C(=O)-R^5$, $-C(=O)OH$, $NH-C(=O)-R^9-C(=O)OH$, $-N=C=S$, $-N=C=O$, $-C\equiv C-R^5$, $-N=N^+=N^-$, $-O-NH_2$, $-O-NH$-Fmoc, $-O-NH$-Boc, $-O-N$-(Boc)$_2$, $-O-N$(-phthalimidyl), $-NH-C(=O)-R^9-O-$ NH-Boc, $-NH-C(=O)-R^9-O-N$-(Boc)$_2$, $NH-C(=O)-R^9-O-N$(-phthalimidyl), $-NH-$ $NH_2$, $-C(=O)-NH-NH_2$, $-NH-C(=O)-$ $NH-NH_2$, $-NH-C(=S)-NH-NH_2$, -toluenesulfonylhydrazide, $-R^5-NH-C(=NH_2^+)-NH_2$, $-NH-C(=NH_2^+)-CH_2CH_2CH_2-SH$,

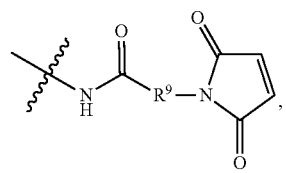

a diazirine, an optionally substituted trifluoromethylphenyldiazirine, an azide, an ester, a carbonate group, an ethyl vinyl, a maleimide, a vinylsulfone, an allyl sulfone, a thioester, an aziridine, each $R^5$ is independently selected from hydrogen, $C_1$-$C_8$ alkyl, alicyclyl, heteroalicyclyl, benzyl, or aryl, wherein any ring in $R^5$ is optionally substituted;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^9$ is independently selected from $C_1$-$C_{16}$ alkyl; and;

each J is independently selected from Cl, Br, and I.

In yet another aspect, the invention generally relates to a method for preparing a bifurcated SA monomer having a chemical structure of Formula I:

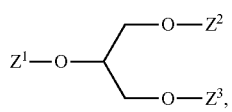

(I)

wherein
each of $Z^1$, $Z^2$, and $Z^3$ is independently selected from the group consisting of $R^{11}$ and

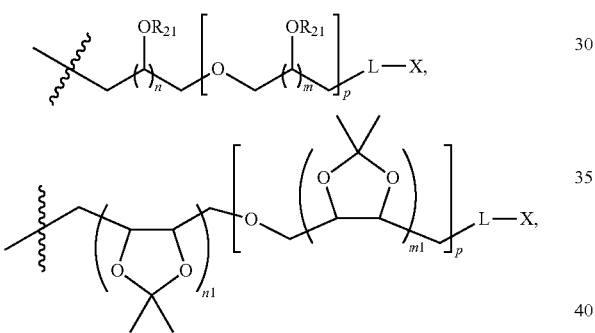

and at least one of $Z^1$, $Z^2$, and $Z^3$ is not $R^{11}$;

each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to about 8;
m is an integer selected from 1 to about 8;
p is an integer selected from 0 to about 50;
n1 is an integer selected from 1 to about 4;
m1 is an integer selected from 1 to about 4;

each L is independently selected from the group consisting of $R^2$ and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(=$G^2$)-$G^1$-, —S—S—, —S—$(CH_2)_2$—$S(O)_2$—, —$S(O)_2$—$(CH_2)_2$—S—, —$S(O)_2$—N($R^3$)—, —N($R^3$)—$S(O)_2$—, —C(O)—NH—NH—$CH_2$—, —C(O)—NH—N=CH—, —CH=N—NH—C(O)—, —$CH_2$—NH—NH—C(O)—, —N($R^3$)—$S(O)_2$—N($R^3$)—, —C(O)—NH—CH($CH_2SH$)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

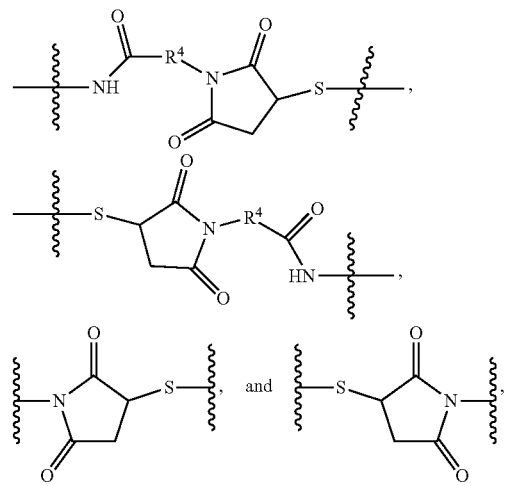

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —$(CH_2CH_2O)_{1-10}$—, —$(CH_2CH_2O)_{1-10}$, —$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —$(OCH_2CH_2)_{1-3}$, optionally substituted alicyclyl, and optionally substituted heteroalicyclyl,
each $R^4$ is independently selected from $C_1$-$C_{16}$ alkyl;

each X is independently selected from —OH, -J, —R⁵J, —C(=O)-J, —C(=O)—CH₂-J, —NH—C(=O)—CH₂-J, —OR⁵, —OR⁶, —OR⁷, —O-mesyl, —O-tosyl, —NH—C(=O)—CH₂—O-mesyl, —NH—C(=O)—CH₂—O-tosyl, —SH, —S—S-t-butyl, —SR⁷, —SR⁵, —S—S—R⁸, —NH—C(=O)—R⁹—S—S—R⁸, —NH—C(=O)—CH₂—SH, —S(=O)₂-J, —NH—C(=O)—R⁹—S—C(=O)—R⁵, —NH₂, —NHR⁵, —N(R³) R⁵, —NHR⁷, —NH-Fmoc, —NH-Boc, N-(phthalimidyl), —C(=O) H, —C(=O)—R⁵, NH—C(=O)—R⁹—C(=O)—R⁵, —C(=O)OH, NH—C(=O)—R⁹—C(=O)OH, —N=C=S, —N=C=O, —C≡C—R⁵, —N=N⁺=N⁻, —O—NH₂, —O—NH-Fmoc, —O—NH-Boc, —O—N-(Boc)₂, —O—N(-phthalimidyl), —NH—C(=O)—R⁹—O— NH-Boc, —NH—C(=O)—R⁹—O—N-(Boc)₂, NH—C(=O)—R⁹—O—N(-phthalimidyl), —NH— NH₂, —C(=O)—NH—NH₂, —NH—C(=O)— NH—NH₂, —NH—C(=S)—NH—NH₂, -toluene-sulfonylhydrazide, —R⁵—NH—C(=NH₂⁺)—NH₂, —NH—C(=NH₂⁺)—CH₂CH₂CH₂—SH,

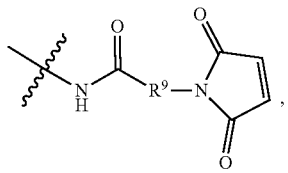

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=N⁺H₂)—O—R⁵, a hydroxymethyl phosphine derivative, an ethyl vinyl, a maleimide, a vinylsulfone, an allyl sulfone, a thioester, a cisplatin derivative, an aziridine, an acryloyl group;

each R⁵ is independently selected from hydrogen, C₁-C₈ alkyl, alicyclyl, heteroalicyclyl, benzyl, or aryl, wherein any ring in R⁵ is optionally substituted;

each R⁶ is independently selected from benzoyl, acetyl, benzyl, C₁-C₈ alkyl silyl, tetrahydropyranyl, tetrahydrofuranyl, and tetrahydrothiofuranyl;

each R⁷ is independently selected from trityl, MMT, and DMT;

each R⁸ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each R⁹ is independently selected from C₁-C₁₆ alkyl; and each J is independently selected from Cl, Br and I, wherein the method comprises:
(i) providing a glycerol;
(ii) combining the glycerol with reagents that can selectively protect the two terminal primary OH groups with R²³ to form an intermediate having a chemical structure of

(iii) providing a first SA molecule with a free primary OH group and have a chemical structure of

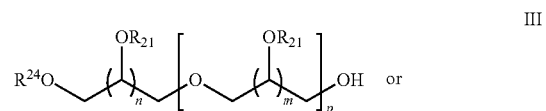

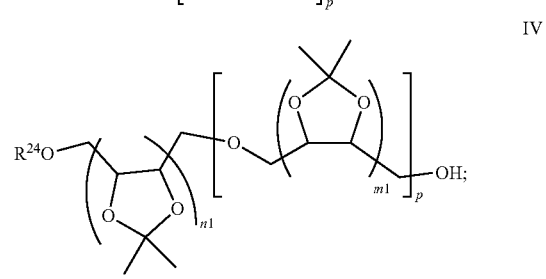

(iv) substituting the primary OH group of III or IV with good leaving group;
(v) combining the first SA molecule and glycerol under conditions that permit the condensation of these two units to form a bifurcated SA monomer;
(vi) removing one or both protecting groups (R²³) of the primary OH groups of glycerol of the bifurcated SA monomer;
(vii) providing a second SA molecule with a free primary OH group and have a chemical structure of

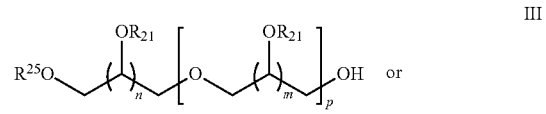

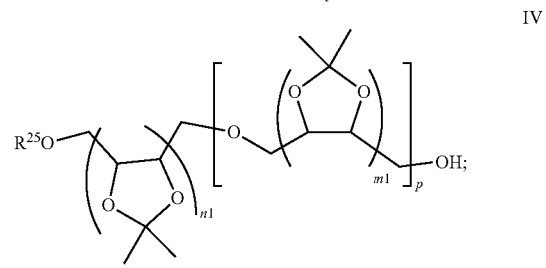

(viii) substituting the primary OH group of the second SA molecule with good leaving group;
(ix) combining the bifurcated SA monomer and one or two of the second SA molecules under conditions that permit the condensation of these two units to form a large bifurcated SA monomer;
(x) combining this bifurcated SA monomer with reagents that selectively deprotect R²⁴ or R²⁵ groups of the SA molecules; and
(xi) reacting further with reagents that allow introduction of linker (L) and different functional group X to form a bifurcated SA monomer having a chemical structure of formula

In yet another aspect, the invention generally relates to a solid phase-based method for assembling a dendrimer-like SA molecule comprising two or more bifurcated SA monomer units, $B_1$, and each $B_1$ unit is bound to one or more other monomeric units through a linking group, W, formed by a reaction between the X group of the $Z^1$ unit and the X group of the $Z^2$ or $Z^3$ unit;
wherein
each $B_1$ has the chemical structure Formula I:

wherein
each of $Z^1$, $Z^2$, and $Z^3$ is independently selected from the group consisting of $R^{11}$ and

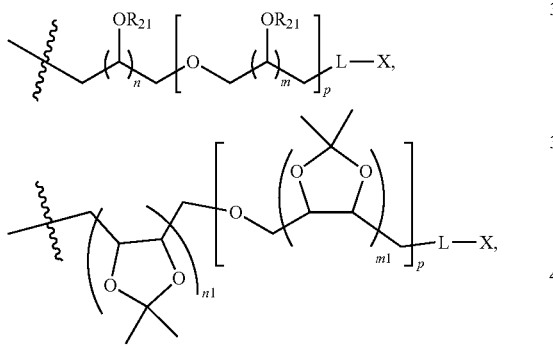

and at least one of $Z^1$, $Z^2$, and $Z^3$ is not $R^{11}$;
each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;
$R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, acetonide of vicinal alcohol;
n is an integer selected from 2 to about 8;
m is an integer selected from 1 to about 8;
p is an integer selected from 0 to about 50;
n1 is an integer selected from 1 to about 4;
m1 is an integer selected from 1 to about 4;
each L and W is independently selected from the group consisting of a bond, $R^2$, and a structure of —$V_1$—$R^2$—$V_2$—, wherein $V_1$, and $V_2$ are independently selected from the group consisting of a Diels-Alder adduct, a 1,3-dipolar adduct, —C($R^4$)(=N)—O—, —O—C($R^4$)(=N)—, —S—CH$_2$—C(=O)—NH—, —NH—C(=O)—CH$_2$—S, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—, —CH=N-$G^4$-, —CH$_2$—NH-$G^4$-, -$G^4$-NH—CH$_2$—, -$G^4$-N=CH—, —C(=NH$_2^+$)—NH—, —NH—C(=NH$_2^+$)—, —O—P(=O)(O$^-$)—NH—, —NH—P(=O)(O)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

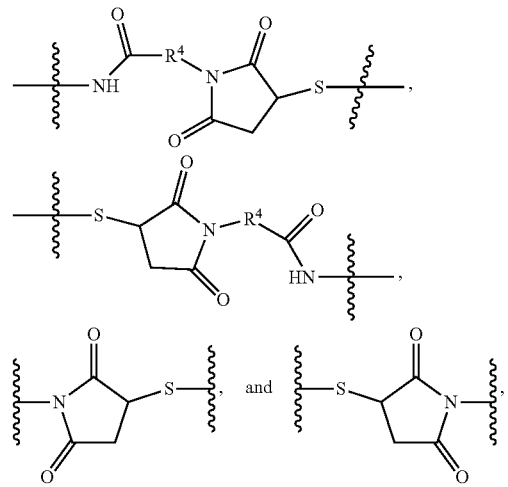

wherein
each $G^1$ is independently selected from NR$^3$, O, and S;
each $G^2$ is independently O or S;
each $G^3$ is independently selected from S, O, NR$^3$, and SO$_2$;
each $G^4$ is independently O or NR$^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, —(CH$_2$CH$_2$O)$_{1-10}$—CH$_2$—, —CH$_2$—(CHOH)$_{1-6}$—, —(CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl,
each $R^4$ is independently selected from $C_1$-$C_{16}$ alkyl;

each X is independently selected from —OH, -J, —R$^5$J, —C(=O)-J, —C(=O)—CH$_2$-J, —NH—C(=O)—CH$_2$-J, —OR$^5$, —OR$^6$, —OR$^7$, —O-mesyl, —O-tosyl, —NH—C(=O)—CH$_2$—O-mesyl, —NH—C(=O)—CH$_2$—O-tosyl, —SH, —S—S-t-butyl, —SR$^7$, —SR$^5$, —S—S—R$^8$, —NH—C(=O)—R$^9$—S—S—R$^8$, —NH—C(=O)—CH$_2$—SH, —S(=O)$_2$-J, —NH—C(=O)—R$^9$—S—C(=O)—R$^5$, —NH$_2$, —NHR$^5$, —N(R$^5$) R$^5$, —NHR$^7$, —NH-Fmoc, —NH-Boc, N-(phthalimidyl), —C(=O) H, —C(=O)—R$^5$, NH—C(=O)—R$^9$—C(=O)—R$^5$, —C(=O)OH, NH—C(=O)—R$^9$—C(=O)OH, —N=C=S, —N=C=O, —C≡C—R$^5$, —N=N$^+$=N$^-$, —O—NH$_2$, —O—NH-Fmoc, —O—NH-Boc, —O—N-(Boc)$_2$, —O—N(-phthalimidyl), —NH—C(=O)—R$^9$—O—NH-Boc, —NH—C(=O)—R$^9$—O—N-(Boc)$_2$, NH—C(=O)—R$^9$—O—N(-phthalimidyl), —NH—NH$_2$, —C(=O)—NH—NH$_2$, —NH—C(=O)—NH—NH$_2$, —NH—C(=S)—NH—NH$_2$, -toluenesulfonylhydrazide, —R$^5$—NH—C(=NH$_2^+$)—NH$_2$, —NH—C(=NH$_2^+$)—CH$_2$CH$_2$CH$_2$—SH,

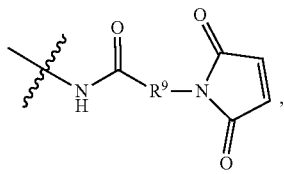

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=N$^+$H$_2$)—O—R$^5$, a hydroxymethyl phosphine derivative, an ethyl vinyl, a maleimide, a vinylsulfone, an allyl sulfone, a thioester, a cisplatin derivative, an aziridine, an acryloyl group;

each R$^5$ is independently selected from hydrogen, C$_1$-C$_8$ alkyl, alicyclyl, heteroalicyclyl, benzyl or aryl, wherein any ring in R$^5$ is optionally substituted;

each R$^6$ is independently selected from benzoyl, acetyl, benzyl, C$_1$-C$_8$ alkyl silyl, tetrahydropyranyl, tetrahydrofuranyl, and tetrahydrothiofuranyl;

each R$^7$ is independently selected from trityl, MMT, and DMT;

each R$^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each R$^9$ is independently selected from C$_1$-C$_{16}$ alkyl; and each J is independently selected from Cl, Br, and I, wherein the method comprises:

(i) providing a solid phase support, wherein solid phase is a commercial polystyrene resin that functioned with any of the following functional group: 4-benzyloxybenzyl alcohol, trityl alcohol, 2-chlorotrityl chloride, trityl chloride, 4-methylotrityl chloride, 4-methoxytrityl chloride, 4-(4-hydroxymethyl-3-methoxyphenoxy) butyryl MBHA, 4-(2'4'-dimethoxyphenylhydroxymethyl) phenoxy, 4-(4-hydroxymethyl-3-methoxyphenoxy) butyryl BHA, 4-hydroymethylbenzoyl MBHA, 4-(4-hydroxymethyl-3-methoxyphenoxy) butyryl MBHA, HMBA AM, TentaGel S PHB, Tentagel S HMBA, 4-hydroxymethylphenoxyacetyl AM, alcohol, ketone, amine, aminomethyl, carbonate, carboxylic acid, thiol, photocleavable;

(ii) providing a first bifurcated SA monomer having a chemical structure of (I)

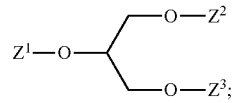

wherein X group of Z$^1$ is selected from the group consisting of —OH, —NH$_2$, —ONH$_2$, —COOH;

(iii) combining solid phase with the first bifurcated SA monomer unit under conditions that permit the attachment of the first bifurcated SA monomer unit onto resin;

(iv) conducting reactions on solid support to activate the X group of Z$^2$ or Z$^3$, or to introduce extra linker or linking group;

(v) providing a second bifurcated SA monomer unit having a chemical structure of (I)

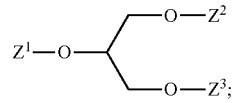

(vi) combining the solid phase with the second bifurcated SA monomer unit under conditions that permit the condensation of one or two of the second bifurcated SA monomer units with the first bifurcated SA monomer unit;

(vii) repeating steps iv to vi to generate higher order dendrimer; and (viii) once the desired dendrimer is achieved, cleaving the dendrimer from the solid support to release the dendrimer-like SA molecule.

The foregoing aspects and embodiments of the invention may be more fully understood by referencing the following FIGURES, detailed description, and claims.

DEFINITIONS

The term "conjugation" or "bioconjugation", as used herein, refers to a chemical process that links two or more molecules together to create new molecules. One of the molecules is preferably a biomolecule. Thus, "bioconjugation" or "conjugation" refers to any chemical process that involves changing a molecule's properties through covalent modification, labeling, conjugation, or immobilization. Conjugation reactions include, for example, amide bond formation through pre-activated carboxylate, such as NHS ester formation with amine; thioether formation through the reaction of sulfhydryl with maleimide or alkyl halide; hydrazone formation through the reaction of hydrazine with ketone or aldehyde; oxime formation through the reaction of aminooxy with ketone or aldehyde; semicarbazone formation through the reaction of semicarbazide with ketone or aldehyde; and reductive amination to conjugate aldehydes and amines. Other less common conjugation reactions include click chemistry (Cu(I)-promoted azide-alkyne [3+2] cycloaddition), the Diels-Alder reaction, and photochemical reactions involving azide.

The term "conjugate", as used herein, refers to a product produced by a "conjugation" reaction of two or more molecules. Examples of molecules that can be conjugated include small molecules, antibodies and their fragments, proteins (soluble and membrane proteins), enzymes, nucleic acids and their analogs, peptides and peptidomimetics, fluorescent compounds, chemiluminescent compounds, radioactive compounds, isotopic containing compounds, biotin and avidin/streptavidin, toxins, drugs, solid support media, and other biologically active molecules. Examples of conjugates include antibody-drug conjugates, protein-drug conjugates, peptide-drug conjugates, oligo-drug conjugates, peptide-oligo conjugates, protein-oligo conjugates, antibody-enzyme conjugates, antibody-protein conjugates, protein-protein conjugates, protein-peptide conjugates, protein-oligo conjugates, fluorescent compounds, immobilized proteins, immobilized peptides, immobilized enzymes, and immobilized oligos.

The term "sugar alcohol" (SA) or "sugar alcohols" (SAs), as used herein, refers to a sugar alcohol that has a general formula of OH—$CH_2$—(CHOH),—OH, wherein n ranges from 0 to approximately 12. In some cases, SA refers to polyol, polyhydric alcohol, or polyalcohol. Examples of natural sugar alcohols are glycol (2-carbon), glycerol (3-carbon), erythritol (4-carbon), threitol (4-carbon), arabitol (5-carbon), xylitol (5-carbon), ribitol (5-carbon), mannitol (6-carbon), sorbitol (6-carbon), dulcitol (6-carbon), and iditol (6-carbon). Sugar alcohols can also be synthetic. When r is 1, sugar alcohol refers to a keto sugar or ketose. Examples of natural ketoses are dihydroxyacetone (3-carbon), erythrulose (4-carbon), ribulose (5-carbon), xylulose (5-carbon), fructose (6-carbon), psicose (6-carbon), sorbose (6-carbon), tagatose (6-carbon), sedoheptulose (7-carbon).

The term "sugar alcohol" (SA unit) or "sugar alcohol units" (SA units), as used herein, refers to an "unmodified" or "modified" mono sugar alcohol. An "unmodified" SA unit has the general formula —$CH_2$—$(CHOH)_n$—$CH_2$— wherein n ranges from 0 to approximately 12. A "modified" SA unit refers to a SA unit in which one or more of its OH groups has been chemically modified by substitution with another functional group. A "modified" SA unit also refers to a SA unit in which one or both of its —$CH_2OH$ groups has been oxidized and then further modified with other functional groups. A "modified" SA unit also refers to a SA unit wherein the hydrogen atom at one or more of the OH groups has been replaced by a chemical protecting group, leaving group, or other functional group. Examples of OH protecting groups include $C_1$-$C_8$ alkyl, benzoyl, acetyl, benzyl, $C_1$-$C_6$ alkyl silyl, tetrahydropyranyl, tetrahydrofuranyl, and tetrahydrothiofuranyl.

The terms "crosslink", "crosslinking", "crosslinked", and grammatical derivatives thereof, refer to the covalent bonding or bonds between molecules or between molecules and solid supports.

The terms "crosslinking group", "functional group", "activated group", and "chemically reactive group", as used herein, refer to distinct, definable portions or units of a molecule that react readily with electrophilic or nucleophilic groups on other molecules to form a new molecule through covalent bonding. Crosslinking groups include, for example, OH, protected OH, carboxylic acid, protected carboxylic groups, amines, protected amines, thiols, protected thiols, disulfides, alkyl groups, benzophenones, anthraquinones, diazo groups, azido groups, acyl azides, alkynes, diazonium groups, diazirenes, dienes, dienophils, 1,3-dipoles, dipolarophiles, alkenes, ketenes, olefins, alkenes with allylic hydrogen, dicarbonyl groups, epoxides, oxiranes, organosilanes, isothiocyanate, isocyanate, phosphonium groups, tosylates, mesylates, acyl azides, esters (e.g., N-hydroxysuccinimidyl ester and 1-benzotriazolyly esters), sulfonyl chlorides, anhydrides, tetrahydropyranyl groups, tetrahydrofuranyl groups, tetrahydrothiofuranyl groups, carbonate groups (e.g., N-hydroxysuccinimidyl carbonates and 1-benzotriazolyl carbonates), aldehydes, ketones, aryl ketones, glyoxals, imidoesters, anhydrides, fluorophenyl esters, hydroxymethyl phosphine derivatives, haloacetyl groups, ethyl vinyls, aryl halides, trityl halides, alkyl halides, acyl halides, silyl halides, maleimides, vinylsulfones, thioesters, cisplatin derivatives, fluorobenzene derivatives, aziridines, acryloyl groups, aminooxy, protected aminooxy, semicarbazide, thiosemicarbazide, hydrazine, guanidinyl, phosphoramidites, and sugar groups. An extensive description of such groups of typical art can be found in the following reference: Greg T. Hermanson "Bioconjugate Techniques", 2008 Elsevier, Inc.

The term "crosslinking reagent", as used herein, refers to a molecule that includes a crosslinking group and is capable of crosslinking with another molecule.

The term "leaving group", as used herein, refers to a chemical moiety that can be substituted with another chemical moiety. Examples of leaving groups include halides (e.g., chloride, bromide, iodide), methanesulfonyl (mesyl), p-toluenesulfonyl (tosyl), trifluromethyl sulfonyl (triflate), and trifluoromethylsulfonate. An extensive description of leaving groups of typical art can be found in: Jerry March, Advanced Organic Chemistry: Reactions, Mechanisms, and Structure, $4^{th}$ Ed., John Wiley and Sons, New York, 1992, 352-357.

The term "protecting group" (PG), as used herein, refers to a molecular group or chemical moiety that blocks a functional group from reacting during other chemical operations/transformations. A protecting group is inert to these chemical operations/transformations but can be removed or cleaved by specific chemical, enzymatic, or photochemical means in such a way that it liberates the original functional group for further reaction. A wide variety of protecting groups are available and known in the art. An extensive description of protecting groups of typical art can be found in: Theodora W. Green and Peter G. M. Wuts, Protective Groups in Organic Synthesis, $2^{nd}$ ed., Wiley-Interscience, New York, 1991.

The term "OH protecting group", as used herein, refers to a molecular group or chemical moiety that blocks an OH group from reacting during other chemical operations/transformations. Examples of chemical moieties include, but are not limited to, alkyl, aryl, benzoyl, acetyl, benzyl, alkyl silyl, tetrahydropyranyl, tetrahydrofuranyl, and tetrahydrothiofuranyl.

The terms "linker" or "linkage" or "linking group", as used herein, refer to groups or bonds that are normally formed as the result of a chemical reaction and typically with covalent bond(s). A linker may contain an extra spacer(s), such as ethylene glycol, methylene, a peptide, or a peptidomimetic oligomer. Linkers include, for example, substituted or un-substituted heteroalicyclyl $C_1$-$C_{12}$ alkyl, —$(CH_2CH_2O)_{1-10}$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, substituted or un-substituted alicyclyl, heteroalicyclyl, aryl, peptides, and peptidomimetic oligomers. The linkers may include linking groups, such as acyl-based linking groups (e.g., —C(O)—NH— and —OC(O)NH—). Exemplary linking groups include, but are not limited to —C(R$^4$)(=N)—O—, —O—C(R$^4$)(=N)—, —S—CH$_2$—C(=O)—NH—, —NH—C(=O)—CH$_2$—S—, Diels-Alder adduct, a 1,3-dipolar adduct, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

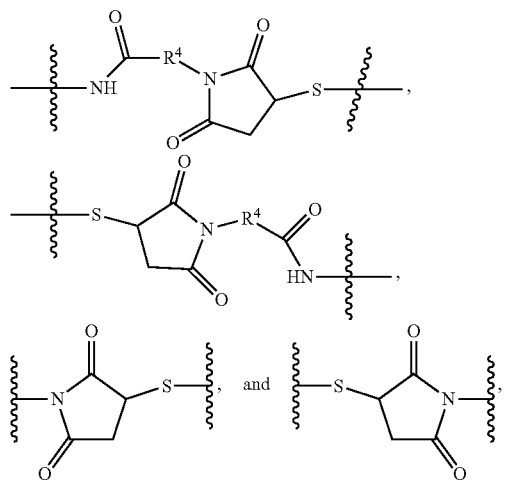

wherein each G$^1$ is independently selected from NR$^3$, O, and S; each G$^2$ is independently O or S; each G$^3$ is independently selected from S, O, NR$^3$, and SO$_2$; each G$^4$ is independently O or NR$^3$; each R$^3$ is independently selected from hydrogen, C$_1$-C$_8$ alkyl, —(OCH$_2$CH$_2$)$_{1-3}$, optionally substituted alicyclyl, and optionally substituted heteroalicyclyl; each R$^4$ is independently C$_1$-C$_{16}$ alkyl;

The term "alkyl", as used herein, refers to a branched, unbranched, or cyclic hydrocarbon having, for example, from 1 to 20 carbon atoms, and often 1 to about 12, 1 to 6, or 1 to 4 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups.

The term "SA molecule", as used herein, refers to a molecule that includes an SA unit. SA molecule refers to any of the SA crosslinking reagents, SA macromolecules, linear SA macromolecules, branched SA macromolecules, and hyperbranched SA macromolecules.

The term "bifurcated", as used herein, refers to a molecule that have two or more branches or forks.

The term "SA macromolecule" as used herein refers to a high molecular weight compound derivatized from the sugar alcohol. Typically, an SA macromolecule is at least two SA units long. The preferred size of an SA macromolecule ranges from approximately 1000 Da to approximately 120,000 Da.

The term "branching", as used herein, refers to the replacement of a substituent, for example a hydrogen atom on a sugar alcohol, by another covalently bonded chain of a sugar alcohol, or by a chain of another type.

The terms "peptide" or "polypeptide", as used herein, refer to a polymer of amino acid residues linked together by a peptide bond. Typically, a peptide is at least two amino acids long. A peptide bond is commonly known in biochemistry as an amide linkage between the carboxyl group of one amino acid and the amino group of another amino acid. The preferred size of peptides ranges from about 2 to about 40 amino acids. The term peptide may also apply to amino acid polymers in which one or more amino acid residues are artificial chemical analogs of a corresponding naturally occurring amino acid. An amino acid polymer in which one or more amino acid residues is an "unnatural" amino acid not corresponding to any naturally occurring amino acid is also encompassed by the term "peptide".

The term "protein", as used herein, refers to a polymer of amino acid residues linked together by a peptide bond. The term is meant to include proteins and polypeptides of any size, structure, or function. However, a protein is typically at least 10 amino acids long. A protein may be naturally occurring, recombinant, synthetic, or any combination of these. A protein may also be a fragment of a naturally occurring protein. A protein may be a single molecule or it may be a multi-molecular complex. The term protein may also apply to amino acid polymers in which one or more amino acid residues are artificial chemical analogs of a corresponding naturally occurring amino acid. An amino acid polymer in which one or more amino acid residues is an "unnatural" amino acid not corresponding to any naturally occurring amino acid is also encompassed by the use of the term "protein".

The term "protein fragment", as used herein, refers to a peptide that is a portion of another protein. For example, protein fragments may be polypeptides obtained by digesting a full-length protein. A protein fragment typically comprises at least two amino acids.

The term "therapeutic agent", as used herein, refers to a compound, or a molecule that is useful in the treatment of a disease. Therapeutic agents include, for example, antibody fragments, drugs, toxins, nucleases, hormones, immunomodulators, pro-apoptotic agents, anti-angiogenic agents, boron compounds, photoactive agents, dyes and radioisotopes, proteins, and constructs that include proteins, oligonucleotides, oligonucleotide analogs, polysaccharides, metabolites, enzymes, polypeptides, and toxins. Therapeutic agents include prodrugs of bioactive agents and constructs.

The term "therapeutic moiety", as used herein, refers to a functional moiety that is derived from a "therapeutic agent".

The term "diagnostic agent", as used herein, refers to a compound, or a molecule that alone or in combination with another agent is able to be used for revealing, pinpointing, and defining the localization of a pathological process. Diagnostic agents include, for example, radioactive substances, fluorescent dyes, chemiluminescent compounds, mass tags, chromophores, biotin, toxins, proteins, enzymes, antibodies, antibody fragments, polypeptides, avidin, streptavidin, oligonucleotides, oligonucleotide analogs, polysaccharides, metabolites, chelating agents, drugs, chemotherapeutic agents, cytotoxic agents, immunosuppressive agents, and radioligands.

The term "diagnostic moiety", as used herein, refers to a functional moiety that is derived from a "diagnostic agent".

The term "a biologically functional moiety", as used herein, refers to a moiety that can elicit some kind of biological function or interact with biological systems to elicit some kind of biological function. "Biologically functional moiety" also refers to a moiety that can aid in detecting or diagnosing some biological function. Examples of biologically functional moieties include therapeutic moieties and diagnostic moieties.

The term "antibody", as used herein, refers to a full-length immunoglobulin molecule or an immunologically active portion of an immunoglobulin molecule, such as an antibody fragment. "Antibody" is used in the broadest sense and includes monoclonal antibodies, polyclonal antibodies, multispecific antibodies (e.g., bispecific antibodies), and antibody fragments. The immunoglobulin disclosed herein can be of any type, for example, IgM, IgD, IgG, IgE, IgA, or any subclass of immunoglobulin, such as IgG1, IgG2a, IgG2b, IgG3, IgA1, and IgA2. Antibodies may be murine, human, humanized, chimeric, rabbit, chicken, or derived from other species.

The term "antibody fragment", as used herein, refers to a portion of an antibody, such as F(ab')2, Fab', Fab, Fv, sFv, diabodies, linear antibodies, fragments produced by a Fab expression library, anti-idiotypic (anti-Id) antibodies, the complementarity determining region (CDR), the extracellular domain (EDC), and epitope-binding fragments of any of the above that immunospecifically bind to cancer cell antigens, viral antigens or microbial antigens, single-chain antibody molecules, and multispecific antibodies formed from antibody fragments. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker (scFv proteins).

The terms "nucleic acid", "oligonucleotide", "oligo", or "polynucleotide", as used herein, refer to a polymer of nucleotides. The polymer may include, without limitation, natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O (6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). Nucleic acids and oligonucleotides may also include other polymers of bases having a modified backbone, such as a locked nucleic acid (LNA), a peptide nucleic acid (PNA), or a threose nucleic acid (TNA).

The term "small interfering RNA" or "siRNA", as used herein, refers to small inhibitory double-stranded RNA molecules that induce the RNA interference (RNAi) pathway. siRNA generally have from about 18 to about 30 base pairs and exhibit varying degrees of complementarity to their target mRNA in the antisense strand. Some, but not all, siRNA have unpaired overhanging bases on the 5' or 3' end of the sense strand and/or antisense strand. The term "siRNA" includes duplexes of two separate strands, as well as single strands that can form hairpin structures comprising a duplex region.

The term "polyglycerol", as used herein, refers to a polymerized glycerol. Glycerol has the structure OH—$CH_2$—CH(OH)—$CH_2$—OH. A polyglycerol contains two or more glycerol units.

Polyglycerol is prepared by general polymerization of glycerol at a higher temperature or under basic conditions.

The term "hydrophobic moiety", as used herein, refers to a nonpolar molecule or group that has little affinity for water. A hydrophobic molecule or portion of a molecule is one that has a tendency to cluster together with other hydrophobic groups in an aqueous environment because they are unable to disrupt the network of strong hydrogen bonds in the water around them. Examples of hydrophobic moieties include alkanes, aromatic groups, cholesterol, lipids, phospholipids, and fatty acids.

The term "aliphatic group", as used herein, refers to acyclic or cyclic, non-aromatic compounds. Examples of aliphatic groups include, but are not limited to, linear or branched alkyl chains, fatty acid chains (e.g., oleic acid), and long chain alkyl thiols (e.g., hexanethiol).

The term "solid support", as used herein, refers to a support that is conventionally used in organic chemistry, for example in oligo and peptide synthesis. The term "solid support", as used herein, also refers to a support that has been used in biochemistry and biology, for example, for biopolymer immobilization and purification. Examples of a solid support includes polystyrene supports, polyamide supports, polyethylene glycol supports, polyacrylic supports, composite supports and polymers thereof, such as polyacrylic/beta-alanine copolymer supports, polyacrylamide/polystyrene copolymer supports, polyacrylamide/polyethylene glycol copolymer supports, polyethyleneglyco/polystyrene copolymer supports, controlled pore glass, agarose, dextran gel, and polysaccharide based polymers. In some cases, the term "solid support" also refers to a particle that has been used in biological assays, for example, or a polymeric microsphere. Examples of such support include a latex microsphere, a polymeric particle consisting of polystyrene or copolymers of styrene, poly(methyl methacrylate), polyvinyltoluene, polu(2-hydroxyethyl methacrylate) and the copolymer, poly(ethylene glycol dimethacrylate/2-hydroxyethylmetacrlate), and poly(lactic-co-polycolic acid). "Solid support" can also include inorganic constructs, metals and semiconductors, super paramagnetic composites, biodegradable constructs, and synthetic dendrimers and dendrons, such as a quantum dot, a dye-coded particle, and a magnetic-coded particle.

The term "MW", as used herein refers to molecular weight.

The term "small molecule", as used herein refers to a low molecular weight organic compound that is below 800 Da. Examples of the small molecules such as biotin, fluorescent labeling compound, sugar, sugar alcohol, metabolites, drugs, pesticides, amino acids, nucleotide, chemilluminent compound, crosslinking reagent.

The term "single MW" or "monodisperse", as used herein refers to one or a collection of compounds having the same size and molecular weight. Natural polymers, such as proteins, peptides, and DNA, are typically monodisperse. SA macromolecules are synthesized and purified from pure chiral starting materials as single MW compounds via standard organic synthesis techniques. SA macromolecules may contain mixtures of compounds that have the same MW but are the stereo or regional isomers of each other. These isomers are generated during synthesis and can be minimized by choosing the right conditions or purification method.

The term "polydisperse" or "polydispersity", as used herein refer to a collection of polymer compounds that have different sizes, shapes, or molecular weights. For example, a polymer usually has a distribution of molecular mass over a certain range. The polydispersity index (PDI), or heterogeneity index, measures the distribution of molecular mass in a given polymer. The index is calculated based on the following formula: $PDI=M_w/M_n$, wherein $M_w$ is the weight average molecular weight and $M_n$ is the number average molecular weight. Depending on the synthetic method used, most of the synthetic polymers except peptides and oligos are polydisperse. Peptides and oligos are synthesized based on standard organic synthesis techniques using pure starting materials and are generally purified to obtain monodispersity.

DETAILED DESCRIPTION OF THE INVENTION

A critical need exists for chemicals with multiple cross-linking groups for the conjugation and modification of biomolecules in the biotechnology and pharmaceutical fields.

For example, fluorescent-labeled antibody conjugates are frequently used in immunoassays, fluorescence microscopy, and other applications. In general, the more fluorescent dye labeled on the antibody, the higher the assay sensitivity. However, due to the hydrophobicity of the fluorescent dyes, only a limited amount of fluorescent dyes can be loaded onto an antibody using classical linkers without aggregation and precipitation. A hydrophilic crosslinking reagent is preferred. SA-based linear crosslinkers have been shown to increase the loading for some small molecules. However, linear SA crosslinker can only load one fluorophore per antibody labeling site. However, high loading is possible using multiple antibody reaction sites, which may create an antibody conjugate with reduced binding affinity. Preferably, branched SA molecules with multiple crosslinking groups should be designed that allow high loading without utilizing too many antibody labeling sites.

In another example, lanthanide chelates are frequently used for dissociation enhanced lanthanide fluoroimmunoassay, and recently for mass cytometry. However, the general labeling method with classical linkers affords 3-5 Eu chelates per antibody. Labeling of antibodies with over 20 Eu3+/IgG may cause aggregation and an elevated background. Branched high loading crosslinking is preferred.

In drug delivery, there is a great need for branched high loading SA molecules for target-specific delivery. For example, antibody drug conjugate (ADC) involves linking a very hydrophobic drug to a water-soluble antibody (Ducry L., editor. (2013) Antibody-drug conjugates, Methods in Molecular Biology, Volume No. 1045. Springer Protocols ISBN: 978-1-62703-540-8). The hydrophobicity of the drugs not only makes it difficult to load them onto the antibody, but also affects the antibody binding activities after antibody loading. The average number of drugs per antibody is currently 4 for an optimized therapeutic index using classical linkers. Due to the limited loading capacity of ADCs, highly potent drugs, such as MMAE (Doronina S. O. et al. Nat Biotechnol 2003, 21, 778-84) and mertansine (Wang L. et al. Protein Sci 2005, 14, 2436-2446) can only be used to achieve efficacy. If more drugs can be loaded onto the antibody, FDA-approved chemotherapy drugs can be used to achieve effective cell killing rather than the high potency drugs, greatly increasing the safety of the drug.

Hyperbranched molecules, such as dendrimers, have been found to have the characteristics of an ideal drug delivery vehicle and been widely investigated as potential carriers of drugs, genes, and vaccines (Patri A. K. et al. Curr Opin Chem Biol 2002, 6, 466-471; Qiuand L. Y. and Bae Y. H. Pharm Res 2006, 23, 1-30; Al-Jamal K. T. et al. J Pharm Sci 2005, 94, 102-113). The synthesis of a dendrimer was first reported in 1985 (Tomolia D. A. et al. Polym J (Tokyo), 1985, 17, 117-132; Newkome G. R. et al. J Org Chem 1985, 50, 2003-2004). The details of dendrimer synthesis have been reviewed extensively (Bai S. et al. Crit Rev Ther Drug Carrier Syst 2006, 23, 437-495).

The present invention provides dendrimer-like SA molecules, their applications in conjugate preparation, and methods for synthesizing these dedrimer-like SA molecules.

In one aspect, the invention generally relates to a bifurcated SA monomer having a chemical structure of Formula I:

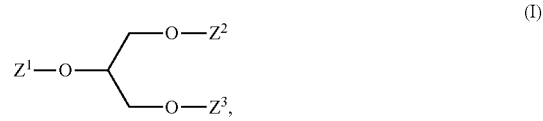

wherein
each of $Z^1$, $Z^2$, and $Z^3$ is independently selected from the group consisting of $R^{11}$ and

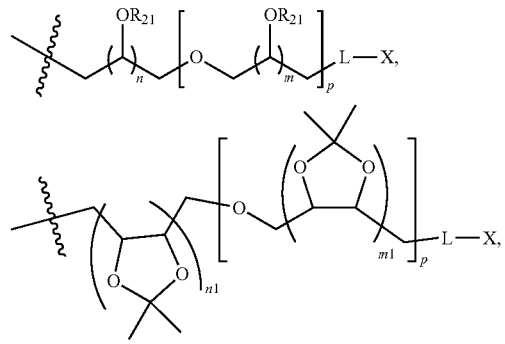

and at least one of $Z^1$, $Z^2$, and $Z^3$ is not $R^{11}$;
each $R^{11}$ is independently selected from the group consisting hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methylthiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to about 8;
m is an integer selected from 1 to about 8;
p is an integer selected from 0 to about 50;
n1 is an integer selected from 1 to about 4;
m1 is an integer selected from 1 to about 4;

each L is independently selected from the group consisting of $R^2$ and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(=$G^2$)-$G^1$-, —S—S—, —S—$(CH_2)_2$—$S(O)_2$—, —$S(O)_2$—$(CH_2)_2$—S—, —$S(O)_2$—$N(R^3)$—, —$N(R^3)$—$S(O)_2$—, —C(O)—NH—NH—$CH_2$—, —C(O)—NH—N=CH—, —CH=N—NH—C(O)—, —$CH_2$—NH—NH—C(O)—, —$N(R^3)$—$S(O)_2$—$N(R^3)$—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

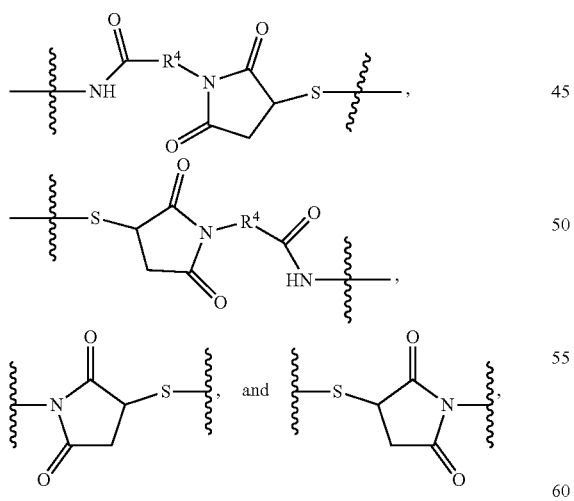

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;

each $R^2$ is independently selected from a bond, $C_1$-$C_{12}$ alkyl, —$(CH_2CH_2O)_{1-10}$—, —$(CH_2CH_2O)_{1-10}$—$CH_2$—, —$CH_2$—$(CHOH)_{1-6}$—, —$CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —$(OCH_2CH_2)_{1-3}$, optionally substituted alicyclyl, and optionally substituted heteroalicyclyl, each $R^4$ is independently selected from $C_1$-$C_{16}$ alkyl, each X is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —$S(=O)_2$-J, —NH—C(=O)—$R^9$—S—C(=O)—$R^5$, —$NH_2$, —$NHR^5$, —$N(R^5)$ $R^5$, —$NHR^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=$N^+$=$N^-$, —O—$NH_2$, —O—NH-Fmoc, —O—NH-Boc, —O—N-$(Boc)_2$, —O—N(-phthalimidyl), —NH—C(=O)—$R^9$—O—NH-Boc, —NH—C(=O)—$R^9$—O—N-$(Boc)_2$, —NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, —NH—C(=$NH_2^+$)—$CH_2CH_2CH_2$—SH,

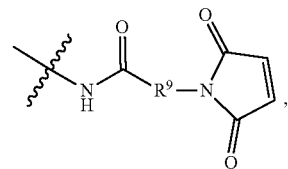

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$N^+H_2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;

each $R^5$ is independently selected from hydrogen, $C_1$-$C_8$ alkyl, alicyclyl, heteroalicyclyl, benzyl or aryl, wherein any ring in $R^5$ is optionally substituted;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^9$ is independently selected from $C_1$-$C_{16}$ alkyl; and each J is independently selected from Cl, Br, and I.

Optionally, each of $Z^1$, $Z^2$, and $Z^3$ may be a protected OH group or a sugar alcohol linked group having a structure of

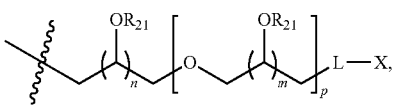

wherein n is an integer selected from 2 to about 8, m is an integer selected from 1 to about 8, and p is an integer selected from 0 to about 8.

Preferably, both n and m are 2. Optionally, both n and m are 4.

Preferably, n1 is 1. More preferably, both n1 and m1 are 1.

In certain embodiments, one of $Z^1$, $Z^2$, and $Z^3$ is derived from threitol and has a structure of

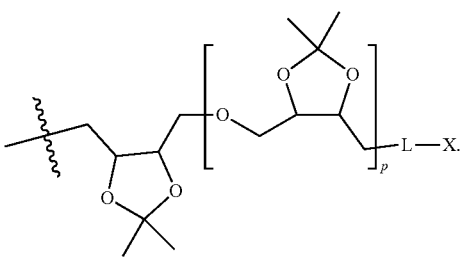

In some preferred embodiments, each of $Z^1$, $Z^2$, and $Z^3$ is derived from threitol and has a structure of

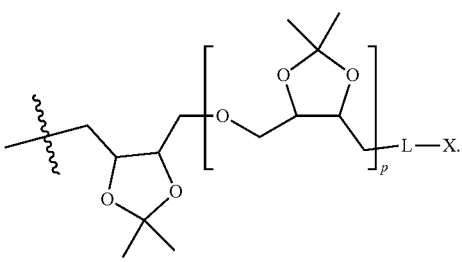

Optionally, p may be 0.

$R^{11}$ is a hydrogen or an OH protecting group. In one aspect, $R^{11}$ may be $C_1$-$C_8$ alkyl silyl. Preferably, $R^{11}$ is a tert-butyldimethylsilyl (TBDMS) protecting group. In another aspect, $R^{11}$ may be a benzyl group. In another aspect, $R^{11}$ may be an acetyl, tetrahydropyranyl, trityl, or a benzyl.

$R^{21}$ is an OH protecting group. In one aspect, $R^{21}$ may be acetyl, benzoyl, benzyl, tetrahydropyranyl, trityl, or $C_1$-$C_8$ alkyl silyl. Preferably, $R^{21}$ is an acetonide group of vicinal alcohol when there is more than one secondary OH group in a sugar alcohol.

In one aspect, L is a linker or linking group formed by reacting one of the primary hydroxyl groups of the SA or a modified SA with another crosslinker reagent. Preferably, the crosslinking reagent is a commercially available reagent, such as ethylene type or PEGylated reagents.

In another aspect, L is a bond.

In certain embodiments, $R^2$ or $R^{22}$ is a peptide linker that can be selectively degraded in vivo by proteases. Examples of such peptide linkers include, but not limited to Gly-Phe-Leu-Gly, Ala-Leu-Ala-Leu, Phe-Arg, Ala-Ala-Asn, Val-Cit.

In certain embodiments, a self immolative spacer may be included in $R^2$ or $R^{22}$. Such slef immolative spacer includes, but not limited to p-aminobenzylcarbonyl group.

In certain embodiments, $R^2$ or $R^{22}$ is a peptide linker with a self immolative spacer such as p-aminobenzylcarbonyl group.

X is a functional group. In certain embodiments, X is an OH. In preferred embodiments, X is a protected OH.

In certain embodiments, functional group X is an amine reactive group. The primary coupling reaction for amine is through acylation or alkylation. The preferred amine active groups include, for example, carboxylic acid, ketenes, isothiocyanate, isocyanate, acyl azides, acyl halides, N-hydroxysuccinimide (NHS) ester, sulfonyl chloride, carbonyl groups such as aldehydes, ketones, and glyoxals, epoxides or oxiranes, carbonate groups, aryl halides such as fluorobenzene derivatives, alkyl halides, imidoester or imidate functional groups, anhydrides, fluorophenyl ester, and hydroxymethyl phosphine derivatives. In a particular example, X is an arginine-reactive group. The guanidinyl group on the arginine side chain can be specifically targeted using 1,2-dicarbonyl reagents, such as the diketone group of glyoxal.

In certain embodiments X is a thiol reactive group. The primary coupling reaction for thiol is through alkylation or disulfide exchange. The preferred thiol reactive groups include, for example, thiol, haloacetyl and alkyl halides, maleimide, aziridines, acryloyl derivatives, arylating agents such as benzene derivatives that possess either halogen or sulfonate groups on the ring, thiol-disulfide exchange reagents such as pyridyl dithiol and thiolnitrobenzoic acid, vinylsulfone, cysteine derivatives, thioesters, and cisplatin derivatives.

In certain embodiments X is a carboxylic acid reactive group. The preferred carboxylic acid reactive groups include, for example, OH, amines, thiols, diazomethane and diazoacetate derivatives, and acylimidazole leaving groups.

In certain embodiments X is an OH reactive group. The preferred hydroxyl reactive groups include, for example, epoxides or oxiranes, alkyl halogens, carboxylic acid and its active esters, isocyanate, isothiocyanate, phosphonium intermediates, tosylate or mesylate, sulfonyl chlorides, anhydrides, acyl azides, tetrahydropyranyl, tetrahydrofuranyl, tetrahydro thiofuranyl, ethyl vinyl, trityl halides, fluorobenzene derivatives, silyl-halides, and ketenes.

In some preferred embodiments X is an aminooxy group capable of reacting with aldehyde or ketone groups to form the oxime bond. In another embodiment X is a hydrazine capable of reacting with aldehyde or ketone groups to form the hydrazine linkage. In another embodiment X is a semi or thiosemicarbazide capable of reacting with aldehyde or ketone groups to form the semi or thiosemicarbazone linkage. In another embodiment X can be an amine functional group. Amine groups can react with aldehydes through Schiff base formation, and the formed carbon amine double bond can be further reduced to a stable secondary or tertiary amine bond. Amine groups can also react with an active hydrogen-containing compound in the presence of formaldehyde (Mannich reaction).

In some embodiments X is able to react with certain reactive (or replaceable) hydrogens that exist in certain biomolecules. For example, X may be a diazonium group that reacts with active hydrogen sites on aromatic rings to produce covalent diazo bonds.

In some preferred embodiments X is a photoreactive group that can be induced to couple with molecules of interest via exposure to UV light. The preferred photoreactive groups include, for example, diazirine groups. More preferable than a diazirine group is 3-trifluoromethyl-3-aryaldiazirine. Other preferred photoreactive groups are aryl azides, halogenated aryl azides, benzophenones, anthraquinones, diazos such as diazotrifluoropropionates and diazopyruvate, and psoralen derivatives.

In some preferred embodiments X is a diene, dienophile group, or alkene that is capable of linking molecules through the Diels-Alder reaction. Preferably, X may be an azido functional group or alkyne that is capable of linking molecules through [3+2] cycloaddition. In another embodiment X may be an alkene with an allylic hydrogen (the ene) or a multiple bond (the enophile). In another embodiment X may be a 1,3-dipole or a dipolarophile (substitute alkenes).

In some preferred embodiments X is a protected thiol (e.g., trityl or t-butyl thiol protected).

In some preferred embodiments X is a protected amine (e.g., trityl, phthalimide, DMT, or MMT protected).

In some preferred embodiments X is independently selected from OH, —NH—C(=O)—CH$_2$-J, —SH, —S—S-t-butyl, —SR$^5$, —S—S—R$^8$, —NH—C(=O)—R$^9$—S—S—R$^8$, —NH—C(=O)—CH$_2$—SH, —NH—C(=O)—R$^9$—S—C(=O)—R$^5$, —NH$_2$, —NHR$^5$, —N(R$^5$) R$^5$, —NH-Fmoc, —NH-Boc, N-(phthalimidyl), —C(=O) H, —C(=O)—R$^5$, NH—C(=O)—R$^9$—C(=O)—R$^5$, —C(=O)OH, NH—C(=O)—R$^9$—(=O)OH, —O—NH$_2$, —O—NH-Fmoc, —O—NH-Boc, —O—N-(Boc)$_2$, —O—N(-phthalimidyl), —NH—C(=O)—R$^9$—O—NH-Boc, —NH—C(=O)—R$^9$—O—N-(Boc)$_2$, NH—C(=O)—R$^9$—O—N(-phthalimidyl), —NH—C(=NH$_2$$^+$)—CH$_2$CH$_2$CH$_2$—SH,

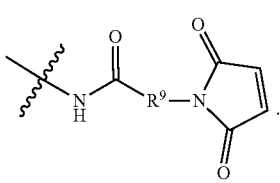

In other preferred embodiments, X of $Z^1$ is —NH$_2$ or —ONH$_2$.

In other preferred embodiments, X of $Z^2$ and $Z^3$ are the same and is independently selected from —NH—C(=O)—CH$_2$-J, —SH, —S—S-t-butyl, —S—S—R$^8$, —NH—C(=O)—R$^9$—S—S—R$^8$, —NH—C(=O)—CH$_2$—SH, —NH—C(=O)—R$^9$—S—C(=O)—R$^5$, —NH$_2$, —NH-Fmoc, —NH-Boc, N-(phthalimidyl), NH—C(=O)—R$^9$—C(=O)—R$^5$, NH—C(=O)—R$^9$—(=O)OH, —O—NH$_2$, —O—NH-Fmoc, —O—NH-Boc, —O—N-(Boc)$_2$, —O—N(-phthalimidyl), —NH—C(=O)—R$^9$—O—NH-Boc, —NH—C(=O)—R$^9$—O—N-(Boc)$_2$, NH—C(=O)—R$^9$—O—N(-phthalimidyl), —NH—C(=NH$_2$$^+$)—CH$_2$CH$_2$CH$_2$—SH,

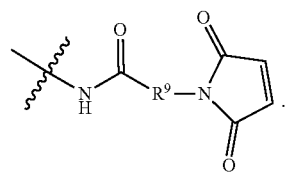

In another aspect, the invention generally relates to a solid phase linked compound comprising one bifurcated SA monomer unit, wherein the bifurcated SA monomer has the chemical structure Formula I:

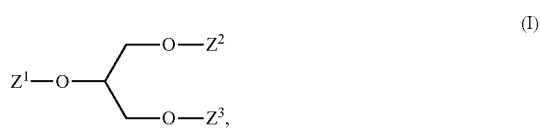

wherein the bifurcated SA monomer is bound to the solid phase through a linking group, W, formed by a reaction between the X group of the $Z^1$ unit and the functional group on the solid phase, wherein the solid phase is a commercial polystyrene resin that functioned with any of the following functional group: 4-benzyloxybenzyl alcohol, trityl alcohol, 2-chlorotrityl chloride, trityl chloride, 4-methyltrityl chloride, 4-methoxytrityl chloride, 4-(4-hydroxymethyl-3-methoxyphenoxy) butyryl MBHA, 4-(2'4'-dimethoxyphenylhydroxymethyl) phenoxy, 4-(4-hydroxymethyl-3-methoxyphenoxy) butyryl BHA, 4-hydroxymethylbenzoyl MBHA, 4-(4-hydroxymethyl-3-methoxyphenoxy) butyryl MBHA, HMBA AM, TentaGel S PHB, Tentagel S HMBA, 4-hydroxymethylphenoxyacetyl AM, alcohol, ketone, amine, aminomethyl, carbonate, carboxylic acid, thiol, photocleavable;

each of $Z^1$, $Z^2$, and $Z^3$ is independently selected from the group consisting of $R^{11}$ and

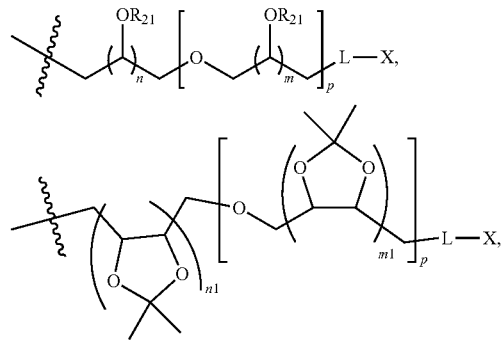

and at least one of $Z^1$, $Z^2$, and $Z^3$ is not $R^{11}$;

each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to about 8;
m is an integer selected from 1 to about 8;
p is an integer selected from 0 to about 50;
n1 is an integer selected from 1 to about 4;
m1 is an integer selected from 1 to about 4;

each L and W is independently selected from the group consisting of $R^2$ and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(-$G^2$)-$G^1$-, —S—S—, —S—$(CH_2)_2$—S(O)$_2$—, —S(O)$_2$—$(CH_2)_2$—S—, —S(O)$_2$—N($R^3$)—, —N($R^3$)—S(O)$_2$—, —C(O)—NH—NH—$CH_2$—, —C(O)—NH—N=CH—, —CH=N—NH—C(O)—, —$CH_2$—NH—NH—C(O)—, —N($R^3$)—S(O)$_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

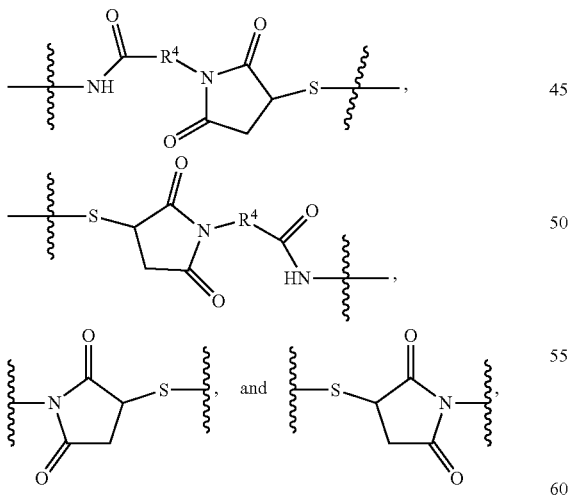

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;

each $R^2$ is independently selected from a bond, $C_1$-$C_{12}$ alkyl, $(CH_2CH_2O)_{1-10}$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —$(OCH_2CH_2)_{1-3}$, optionally substituted alicyclyl, and optionally substituted heteroalicyclyl, each $R^4$ is independently selected from $C_1$-$C_{16}$ alkyl;

each X is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —S(=O)$_2$-J, —NH—C(=O)—$R^9$—S—C(=O)—$R^5$, —$NH_2$, —$NHR^5$, —N($R^5$) $R^5$, —$NHR^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=$N^+$=$N^-$, —O—$NH_2$, —O—NH-Fmoc, —O—NH-Boc, —O—N-(Boc)$_2$, —O—N(-phthalimidyl), —NH—C(=O)—$R^9$—O—NH-Boc, —NH—C(=O)—$R^9$—O—N-(Boc)$_2$, —NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, —NH—C(=$NH_2^+$)—$CH_2CH_2CH_2$—SH,

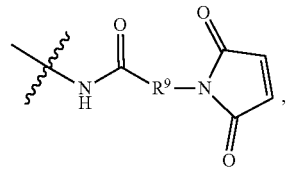

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$N^+H_2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;

wherein
each $R^5$ is independently selected from hydrogen, $C_1$-$C_8$ alkyl, alicyclyl, heteroalicyclyl, benzyl, or aryl, wherein any ring in $R^5$ is optionally substituted;

each $R^6$ is independently selected from benzoyl, acetyl, benzyl, $C_1$-$C_8$ alkyl silyl, tetrahydropyranyl, tetrahydrofuranyl, and tetrahydrothiofuranyl;

each $R^7$ is independently selected from trityl, MMT, and DMT;

each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^9$ is independently selected from $C_1$-$C_{16}$ alkyl; and each J is independently selected from Cl, Br and I.

Preferably, the solid phase is selected from 2-chlorotrityl chloride resin, trityl chloride resin, 4-methylotrityl chloride resin, and 4-methoxytrityl chloride resin.

Optionally, each of $Z^1$, $Z^2$, and $Z^3$ is a sugar alcohol linked group having a structure of

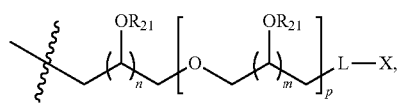

wherein $R^{21}$ is independently selected from the group consisting of acetyl, benzoyl, benzyl, tetrahydropyranyl, trityl, $C_1$-$C_8$ alkyl silyl, and an acetonide group of vicinal alcohol when there is more than one secondary OH group in a sugar alcohol.

Preferably, p is an integer selected from 0 to 4. More preferably, p is 0.

In some preferred embodiments L is a bond.

Preferably, both n and m are 2. Optionally, both n and m are 4.

In certain embodiment, each of $Z^1$, $Z^2$, and $Z^3$ is a sugar alcohol linked group having a structure of

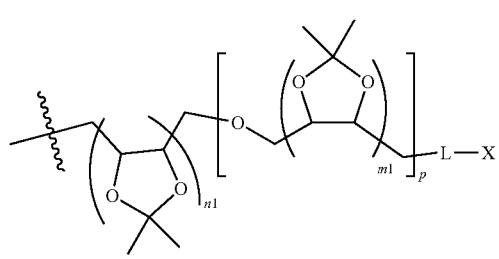

wherein n1 is an integer selected from 1 to about 4, m1 is an integer selected from 1 to about 4, and p is an integer selected from 0 to about 8.

Preferably, n1 is 1. More preferably, both n1 and m1 are 1.

Optionally, p may be 0.

In some preferred embodiment, W is formed by a reaction between the X group of the $Z^1$ unit and the functional group on the solid phase. The functional group on the solid phase is selected from —NH—, —O—NH—, —O—, —S—, —C(=O)—O—, and —C(=O)—NH$_2$—. More preferably, W is —NH—, —ONH, —O—.

In some preferred embodiment, X of $Z^2$ and $Z^3$ is the same and is selected from —OH, —NH—C(=O)—CH$_2$-J, —OR$^5$, —OR$^6$, —OR$^7$, —SH, —S—S-t-butyl, —SR$^5$, —S—S—R$^8$, —NH—C(=O)—R$^9$—S—S—R$^8$, —NH—C(=O)—CH$_2$—SH, —NH—C(=O)—R$^9$—S—C(=O)—R$^5$, —NH$_2$, —NH-Fmoc, —NH-Boc, N-(phthalimidyl), NH—C(=O)—R$^9$—O—R$^5$, NH—C(=O)—R$^9$—(=O)OH, —N=N$^+$=N$^-$, —O—NH$_2$, —O—NH-Fmoc, —O—NH-Boc, —O—N-(Boc)$_2$, —O—N(-phthalimidyl), —NH—C(=O)—R$^9$—O—NH-Boc, —NH—C(=O)—R$^9$—O—N-(Boc)$_2$, NH—C(=O)—R$^9$—O—N(-phthalimidyl), —NH—C(=NH$_2^+$)—CH$_2$CH$_2$CH$_2$—SH,

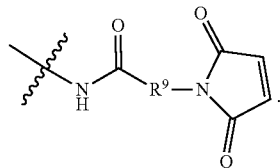

In another aspect, the invention generally relates to a dendrimer-like SA molecule comprising two or more bifurcated SA monomer units $B_1$, wherein each $B_1$ has the chemical structure Formula I:

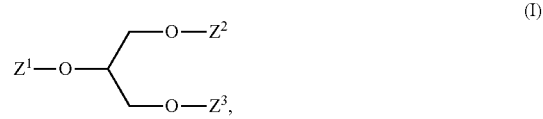

(I)

and each $B_1$ unit is bound to one or more other monomeric units through a linking group, W, formed by a reaction between the X group of the $Z^1$ unit and the X group of the $Z^2$ or $Z^3$ unit, wherein each of $Z^1$, $Z^2$, and $Z^3$ is independently selected from the group consisting of $R^{11}$ and

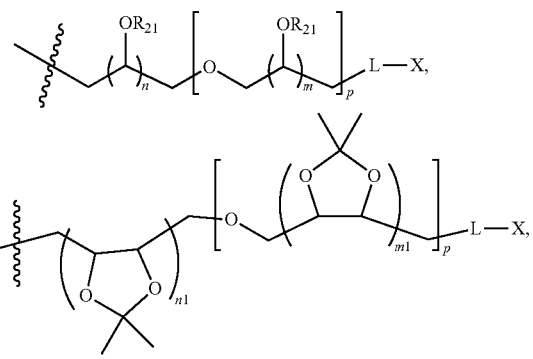

and at least one of $Z^1$, $Z^2$, and $Z^3$ is not $R^{11}$;

each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, sily ether, $C_1$-$C_8$ alkyl silyl, methyl ethers, and ethoxyethyl ethers;

$R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, sily ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to about 8;
m is an integer selected from 1 to about 8;
p is an integer selected from 0 to about 50;
n1 is an integer selected from 1 to about 4;
m1 is an integer selected from 1 to about 4;
each L and W is independently selected from the group consisting of a bond, $R^2$, and a structure of $-V_1-R^2-V_2-$, wherein $V_1$, and $V_2$ are independently selected from the group consisting of a Diels-Alder adduct, a 1,3-dipolar adduct, $-C(R^4)(=N)-O-$, $-O-C(R^4)(=N)-$, $-S-CH_2-C(=O)-NH-$, $-NH-C(=O)-CH_2-S-$, $-C(=G^2)-G^1-$, $-G^1-C(=G^2)-$, $-G^3-$, $-G^1-C(=G^2)-G^1-$, $-S-S-$, $-S-(CH_2)_2-S(O)_2-$, $-S(O)_2-(CH_2)_2-S-$, $-S(O)_2-N(R^3)-$, $-N(R^3)-S(O)_2-$, $-C(O)-NH-NH-CH_2-$, $-C(O)_2-$, $-NH-N=CH-$, $-CH=N-NH-C(O)-$, $-CH_2-NH-NH-C(O)-$, $-N(R^3)-S(O)_2-N(R^3)-$, $-C(O)-NH-CH(CH_2SH)-$, $-N=CH-$, $-NH-CH_2-$, $-NH-C(O)-CH_2-C(O)-NH-$, $-CH=N-G^4-$, $-CH_2-NH-G^4-$, $-G^4-NH-CH_2-$, $-G^4-N=CH-$, $-C(=NH_2^+)-NH-$, $-NH-C(=NH_2^+)-$, $-O-P(=O)(O^-)-NH-$, $-NH-P(=O)(O^-)-O-$, $-CH_2-CH(NH_2)-CH_2-S-$, $-S-CH_2-CH(NH_2)-CH_2-$, $-O-P(=O)(O^-)-O-$, $-O-P(=O)(S^-)-O-$, $-O-P(=S)(S^-)-O-$,

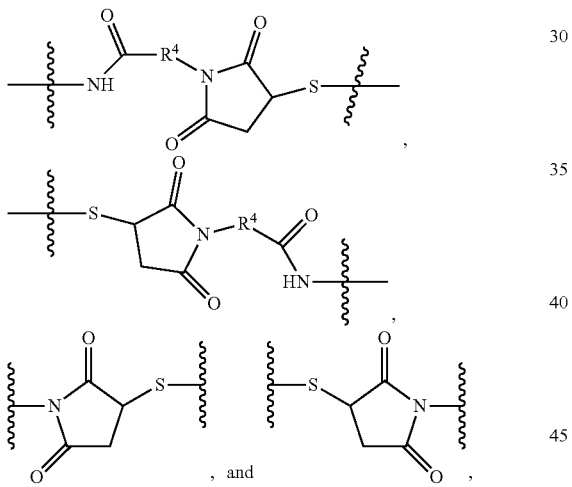

, and

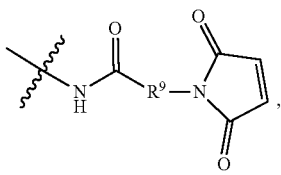

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, $-(CH_2CH_2O)_{1-10}-$, $-(CH_2CH_2O)_{1-10}-CH_2-$, $-(CH_2CH_2O)_{1-10}-CH_2-$, $-CH_2-(CHOH)_{1-6}-$, $-(CHOH)_{1-6}-CH_2-$, $-(CHOH)_{1-6}-$, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, $-(OCH_2CH_2)_{1-3}$, optionally substituted alicyclyl, and optionally substituted heteroalicyclyl, each $R^4$ is independently selected from $C_1$-$C_{16}$ alkyl;
each X is independently selected from $-OH$, $-J$, $-R^5J$, $-C(=O)-J$, $-C(=O)-CH_2-J$, $-NH-C(=O)-CH_2-J$, $-OR^5$, $-OR^6$, $-OR^7$, $-O$-mesyl, $-O$-tosyl, $-NH-C(=O)-CH_2-O$-mesyl, $-NH-C(=O)-CH_2-O$-tosyl, $-SH$, $-S-S$-t-butyl, $-SR^7$, $-SR^5$, $-S-S-R^8$, $-NH-C(=O)-R^9-S-S-R^8$, $-NH-C(=O)-CH_2-SH$, $-S(=O)_2-J$, $-NH-C(=O)-R^9-S-C(=O)-R^5$, $-NH_2$, $-NHR^5$, $-N(R^5)R^5$, $-NHR^7$, $-NH$-Fmoc, $-NH$-Boc, N-(phthalimidyl), $-C(=O)H$, $-C(=O)-R^5$, $-NH-C(=O)-R^9-C(=O)-R^5$, $-C(=O)OH$, $-NH-C(=O)-R^9-C(=O)OH$, $-N=C=S$, $-N=C=O$, $-C\equiv C-R^5$, $-N=N^+=N^-$, $-O-NH_2$, $-O-NH$-Fmoc, $-O-NH$-Boc, $-O-N(Boc)_2$, $-O-N$(-phthalimidyl), $-NH-C(=O)-R^9-O-NH$-Boc, $-NH-C(=O)-R^9-O-N(Boc)_2$, $-NH-C(=O)-R^9-O-N$(-phthalimidyl), $-NH-NH_2$, $-C(=O)-NH-NH_2$, $-NH-C(=O)-NH-NH_2$, $-NH-C(=S)-NH-NH_2$, -toluenesulfonylhydrazide, $-R^5-NH-C(=NH_2^+)-NH_2$, $-NH-C(=NH_2^+)-CH_2CH_2CH_2-SH$,

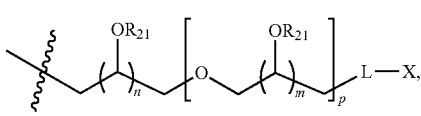

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, $-C(=N^+H_2)-O-R^5$, a hydroxymethyl phosphine derivative, an ethyl vinyl, a maleimide, a vinylsulfone, an allyl sulfone, a thioester, a cisplatin derivative, an aziridine, an acryloyl group;
each $R^5$ is independently selected from hydrogen, $C_1$-$C_8$ alkyl, alicyclyl, heteroalicyclyl, benzyl or aryl, wherein any ring in $R^5$ is optionally substituted;
each $R^6$ is independently selected from benzoyl, acetyl, benzyl, $C_1$-$C_8$ alkyl silyl, tetrahydropyranyl, tetrahydrofuranyl, and tetrahydrothiofuranyl;
each $R^7$ is independently selected from trityl, MMT, and DMT;
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each $R^9$ is independently selected from $C_1$-$C_{16}$ alkyl; and
each J is independently selected from Cl, Br, and I.
Optionally, each of $Z^1$, $Z^2$, and $Z^3$ is a sugar alcohol linked group having a structure of wherein n is an integer selected from 2 to about 8, m is an integer selected from 1 to about 8, and p is an integer selected from 0 to about 8, $R_{21}$ is hydrogen.

In some preferred embodiments L is a bond.

In some preferred embodiments W formed by a reaction between the X group of the $Z^1$ unit and the X group of the $Z^2$ or $Z^3$ unit and is selected from —NH—C(=O)—$R^2$—C($R^4$)(=N)—O—, —O—C($R^4$)(=N)—$R^2$—C(=O)—NH, —NH—C(=O)—$R^2$—C(=O)—NH—, —NH—C(=O)—$R^2$—S—CH$_2$—C(=O)—NH—, —NH—C(=O)—CH$_2$—S—$R^2$—C(=O)—NH—, —S—CH$_2$—C(=O)—NH—, —NH—C(=O)—CH$_2$—S—.

In some preferred embodiments W formed by a reaction between the X group of the $Z^1$ unit and the X group of the $Z^2$ or $Z^3$ unit and is selected from —NH—C(=O)—$R^2$—C($R^4$)(=N)—O—, —O—C($R^4$)(=N)—$R^2$—C(=O)—NH, —NH—C(=O)—$R^2$—C(=O)—NH—, —NH—C(=O)—$R^2$—S—CH$_2$—C(=O)—NH—, —NH—C(=O)—CH$_2$—S—$R^2$—C(=O)—NH—, —S—CH$_2$—C(=O)—NH—, —NH—C(=O)—CH$_2$—S—.

Preferably, $R^4$ is —CH$_3$ and $R^2$ is —CH$_2$CH$_2$—

Optionally, n is 2 and m is 2.

Preferably, p is an integral selected from 0 to 4. More preferably, p is 0.

In some preferred embodiment, the dendrimer is formed by 3, 7, 15, or 31 bifurcated SA monomer. More preferably, the dendrimer is formed by 3 bifurcated SA monomers.

In some preferred embodiment, X is selected from the group consisting of —ONH$_2$, —NH—C(=O)—$R^9$—S—C(=O)—$R^5$, —NH$_2$, NH—C(=O)—$R^9$—(=O)OH, —NH—C(=O)—CH$_2$-J, —SH, —S—S-t-butyl, —S—S—$R^8$, —NH—C(=O)—$R^9$—S—S—$R^8$, —NH—C(=O)—CH$_2$—SH, —NH—C(=O)—$R^9$—S—C(=O)—$R^5$,

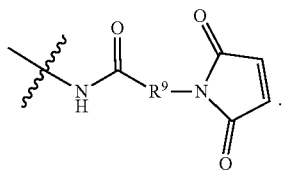

.

In another aspect, the invention generally relates to a conjugate formed by a reaction of ($M_1$) with the X group of $Z^1$ of a bifurcated monomer unit $B_1$ or a dendrimer-like SA molecule B comprising two or more bifurcated monomer units $B_1$, wherein the conjugate has a chemical structure Formula (III) or (IV):

$$M_1\text{-}(L_2\text{-}B_1)_r \quad \text{(III) or}$$

$$M_1\text{-}(L_2\text{-}B)_r \quad \text{(IV),}$$

wherein each $M_1$ is independently selected from the group consisting of a solid support, a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;

r is an integer selected from 1 to about 50;

each $L_2$ is a linking group that formed by a reaction of $M_1$ with the X group of $Z^1$ and is independently selected from the group consisting of $R^{22}$ and a structure of —$V_{11}$—$R^{22}$—$V_{22}$—, wherein $V_{11}$ and $V_{22}$ are independently selected from the group consisting of a Diels-Alder adduct, a 1,3-dipolar adduct, —C($R^4$)(=N)—O—, —O—C($R^4$)(=N)—, —S—CH$_2$—C(=O)—NH—, —NH—C(=O)—CH$_2$—S—, —C(-$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—, —CH=N-$G^4$-, —CH$_2$—NH-$G^4$-, -$G^4$-NH—CH$_2$—, -$G^4$-N=CH—, —C(=NH$_2{}^+$)—NH—, —NH—C(=NH$_2{}^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

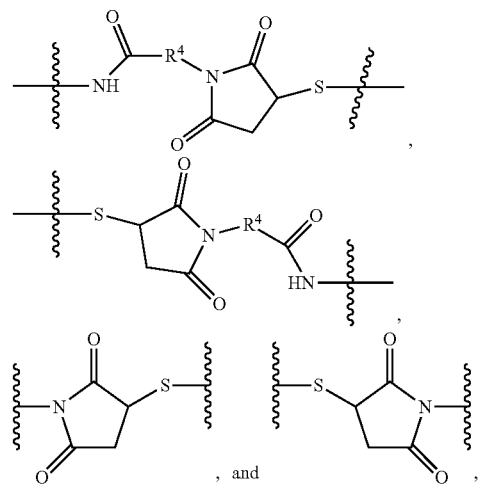

, and , wherein each $G^1$ is independently selected from NR$^3$, O, and S;

each $G^2$ is independently O or S;

each $G^3$ is independently selected from S, O, NR$^3$, and SO$_2$;

each $G^4$ is independently O or NR$^3$;

each $R^{22}$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, —CH$_2$—(CHOH)$_{1-6}$—, —(CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl;

each $R^4$ is independently selected from $C_1$-$C_{16}$ alkyl; and each B comprising two or more bifurcated SA monomer units $B_1$, wherein each $B_1$ has the chemical structure Formula I:

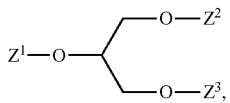 (I)

and each $B_1$ unit is bound to one or more other monomeric units through a linking group, W, formed by a reaction between the X group of the $Z^1$ unit and the X group of the $Z^2$ or $Z^3$ unit;
wherein
each of $Z^1$, $Z^2$, and $Z^3$ is independently

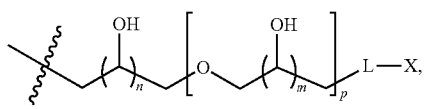

wherein
n is an integer selected from 2 to about 8;
m is an integer selected from 1 to about 8;
p is an integer selected from 0 to about 4;
each L and W is independently selected from the group consisting of a bond, $R^2$, and a structure of $-V_1-R^2-V_2-$, wherein $V_1$ and $V_2$ are independently selected from the group consisting of a Diels-Alder adduct, a 1,3-dipolar adduct, $-C(R^4)(=N)-O-$, $-O-C(R^4)(=N)-$, $-S-CH_2-C(=O)-NH-$, $-NH-C(=O)-CH_2-S-$, $-C(=G^2)-G^1-$, $-G^1-C(=G^2)-$, $-G^3-$, $-G^1-C(=G^2)-G^1-$, $-S-S-$, $-S-(CH_2)_2-S(O)_2-$, $-S(O)_2-(CH_2)_2-S-$, $-S(O)_2-N(R^3)-$, $-N(R^3)-S(O)_2-$, $-C(O)-NH-NH-CH_2-$, $-C(O)-NH-N=CH-$, $-CH=N-NH-C(O)-$, $-CH_2-NH-NH-C(O)-$, $-N(R^3)-S(O)_2-N(R^3)-$, $-C(O)-NH-CH(CH_2SH)-$, $-N=CH-$, $-NH-CH_2-$, $-NH-C(O)-CH_2-C(O)-NH-$, $-CH=N-G^4-$, $-CH_2-NH-G^4-$, $-G^4-NH-CH_2-$, $-G^4-N=CH-$, $-C(=NH_2^+)-NH-$, $-NH-C(=NH_2^+)-$, $-O-P(=O)(O^-)-NH-$, $-NH-P(=O)(O^-)-O-$, $-CH_2-CH(NH_2)-CH_2-S-$, $-S-CH_2-CH(NH_2)-CH_2-$, $-O-P(=O)(O^-)-O-$, $-O-P(=O)(S^-)-O-$, $-O-P(=S)(S^-)-O-$,

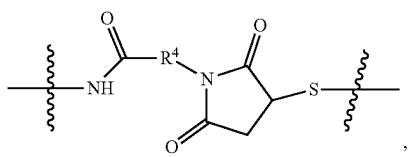

,

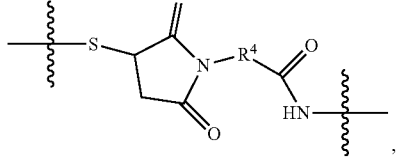

,

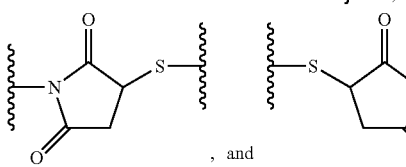 , and wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, $-(CH_2CH_2O)_{1-10}-$, $-(CH_2CH_2O)_{1-10}-CH_2-$, $-(CH_2CH_2O)_{1-10}-CH_2-$, $-CH_2-(CHOH)_{1-6}-$, $-(CHOH)_{1-6}-CH_2-$, $-(CHOH)_{1-6}-$, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, $-(OCH_2CH_2)_{1-3}$, optionally substituted alicyclyl, and optionally substituted heteroalicyclyl,
each $R^4$ is independently selected from $C_1$-$C_{16}$ alkyl,
each X is independently selected from $-OH$, -J, $-R^5J$, $-C(=O)-J$, $-C(=O)-CH_2-J$, $-NH-C(=O)-CH_2-J$, $-OR^5$, $-OR^6$, $-OR^7$, $-O$-mesyl, $-O$-tosyl, $-NH-C(=O)-CH_2-O$-mesyl, $-NH-C(=O)-CH_2-O$-tosyl, $-SH$, $-S-S$-t-butyl, $-SR^7$, $-SR^5$, $-S-S-R^8$, $-NH-C(=O)-R^9-S-S-R^8$, $-NH-C(=O)-CH_2-SH$, $-S(=O)_2-J$, $-NH-C(=O)-R^9-S-C(=O)-R^5$, $-NH_2$, $-NHR^5$, $-N(R^5)$ $R^5$, $-NHR^7$, $-NH$-Fmoc, $-NH$-Boc, N-(phthalimidyl), $-C(=O)$ H, $-C(=O)-R^5$, $NH-C(=O)-R^9-C(=O)-R^5$, $-C(=O)OH$, $NH-C(=O)-R^9-C(=O)OH$, $-N=C=S$, $-N=C=O$, $-C\equiv C-R^5$, $-N=N^+=N^-$, $-O-NH_2$, $-O-NH$-Fmoc, $-O-NH$-Boc, $-O-N-(Boc)_2$, $-O-N(-phthalimidyl)$, $-NH-C(=O)-R^9-O-NH$-Boc, $-NH-C(=O)-R^9-O-N-(Boc)_2$, $NH-C(=O)-R^9-O-N(-phthalimidyl)$, $-NH-NH_2$, $-C(=O)-NH-NH_2$, $-NH-C(=O)-NH-NH_2$, $-NH-C(=S)-NH-NH_2$, -toluenesulfonylhydrazide, $-R^5-NH-C(=NH_2^+)-NH_2$, $-NH-C(=NH_2^+)-CH_2CH_2CH_2-SH$,

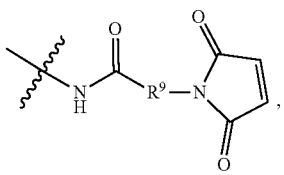

, a diazirine, an optionally substituted trifluoromethylphenyldiazirine, an azide, an ester, a carbonate group, an ethyl vinyl, a maleimide, a vinylsulfone, an allyl sulfone, a thioester, an aziridine,
each $R^5$ is independently selected from hydrogen, $C_1$-$C_8$ alkyl, alicyclyl, heteroalicyclyl, benzyl, or aryl, wherein any ring in $R^5$ is optionally substituted;
each $R^6$ is independently selected from benzoyl, acetyl, benzyl, $C_1$-$C_8$ alkyl silyl, tetrahydropyranyl, tetrahydrofuranyl, and tetrahydrothiofuranyl;
each $R^7$ is independently selected from trityl, MMT, and DMT;
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;

each $R^9$ is independently selected from $C_1$-$C_{16}$ alkyl; and;

each J is independently selected from Cl, Br, and I.

Optionally, L is a bond.

Preferably, n is 2. More preferably, m is also 2.

In some preferred embodiments, p is 0.

In another preferred embodiments, p is 1.

Optionally, B comprises one bifurcated monomer units $B_1$. In another preferred embodiment, B comprises three bifurcated monomer units $B_1$.

In some preferred embodiments, X of $Z^2$ and $Z^3$ is the same and is selected from —NH—C(=O)—CH$_2$-J, —NH—C(=O)—$R^9$—S—S—$R^8$, —NH—C(=O)—$R^9$—S—C(=O)—$R^5$, —NH$_2$, —NH—C(=O)—$R^9$—C(=O)—$R^5$, NH—C(=O)—$R^9$—(=O)OH, —O—NH$_2$,

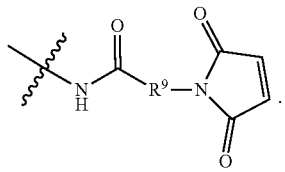

In another aspect, the invention generally relates to a conjugate having a chemical structure Formula (V) or (VI):

B-(L$_1$-M$_2$)$_q$      (V) or

B$_1$-(L$_1$-M$_2$)$_q$      (VI), wherein the conjugate is formed by a reaction of one or several molecules (M$_2$) with one or several X groups of any of the $Z^2$ and $Z^3$ of a bifurcated SA monomer $B_1$ or a dendrimer-like SA molecule B comprising two or more bifurcated SA monomer units $B_1$, wherein each M$_2$ is independently a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;

q is an integer selected from 1 to about 50;

each L$_1$ is independently selected from the group consisting of $R^{22}$ and a structure of —V$_{11}$—$R^{22}$—V$_{11}$—, wherein V$_{11}$ and V$_{22}$ are independently selected from the group consisting of a Diels-Alder adduct, a 1,3-dipolar adduct, —C(R$^4$)(=N)—O—, —O—C(R$^4$)(=N)—, —S—CH$_2$—C(=O)—NH—, —NH—C(=O)—CH$_2$—S—, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH—N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O)—$^-$O—, —O—P(=O)(S$^-$)—O—, —O—P(=S)(S$^-$)—O—,

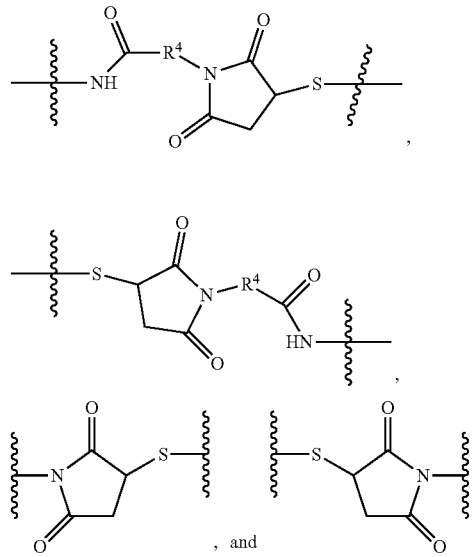

, and

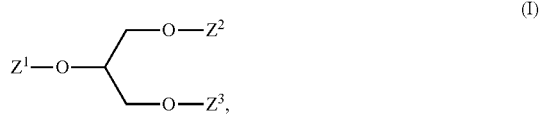

, wherein each G$^1$ is independently selected from NR$^3$, O, and S;

each G$^2$ is independently O or S;

each G$^3$ is independently selected from S, O, NR$^3$, and SO$_2$;

each G$^4$ is independently O or NR$^3$;

each $R^{22}$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, —CH$_2$—(CHOH)$_{1-6}$—, —CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl;

each $R^4$ is independently selected from $C_1$-$C_{16}$ alkyl; and each B comprising two or more bifurcated SA monomer units $B_1$, wherein each $B_1$ has the chemical structure Formula I:

and each $B_1$ unit is bound to one or more other monomeric units through a linking group, W, formed by a reaction between the X group of the $Z^1$ unit and the X group of the $Z^2$ or $Z^3$ unit;

wherein
each of $Z^1$, $Z^2$, and $Z^3$ is independently

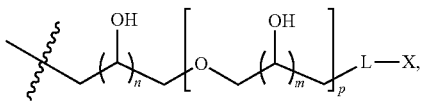

wherein
n is an integer selected from 2 to about 8;
m is an integer selected from 1 to about 8;
p is an integer selected from 0 to about 4;
each L and W is independently selected from the group consisting of a bond, $R^2$, and a structure of $-V_1-R^2-V_2-$, wherein $V_1$, and $V_2$ are independently selected from the group consisting of a Diels-Alder adduct, a 1,3-dipolar adduct, $-C(R^4)(=N)-O-$, $-O-C(R^4)(=N)-$, $-S-CH_2-C(=O)-NH-$, $-NH-C(=O)-CH_2-S-$, $-C(=G^2)-G^1-$, $-G^1-C(=G^2)-$, $-G^3-$, $-G^1-C(=G^2)-G^1-$, $-S-S-$, $-S-(CH_2)_2-S(O)_2-$, $-S(O)_2-(CH_2)_2-S-$, $-S(O)_2-N(R^3)-$, $-N(R^3)-S(O)_2-$, $-C(O)-NH-NH-CH_2-$, $-C(O)-NH-N=CH-$, $-CH=N-NH-C(O)-$, $-CH_2-NH-NH-C(O)-$, $-N(R^3)-S(O)_2-N(R^3)-$, $-C(O)-NH-CH(CH_2SH)-$, $-N=CH-$, $-NH-CH_2-$, $-NH-C(O)-CH_2-C(O)-NH-$, $-CH=N-G^4-$, $-CH_2-NH-G^4-$, $-G^4-NH-CH_2-$, $-G^4-N=CH-$, $-C(=NH_2^+)-NH-$, $-NH-C(=NH_2^+)-$, $-O-P(=O)(O^-)-NH-$, $-NH-P(=O)(O^-)-O-$, $-CH_2-CH(NH_2)-CH_2-S-$, $-S-CH_2-CH(NH_2)-CH_2-$, $-O-P(=O)(O^-)-O-$, $-O-P(=O)(S^-)-O-$, $-O-P(=S)(S^-)-O-$,

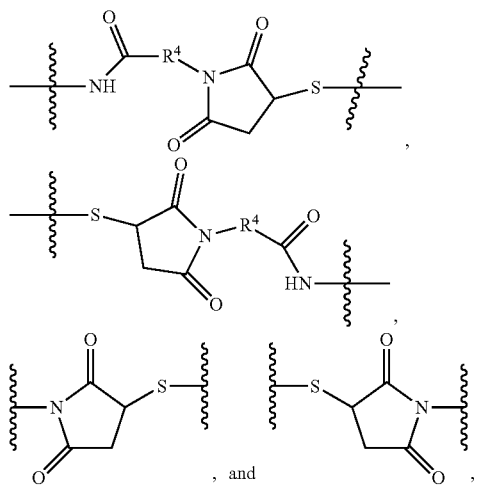

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, $-(CH_2CH_2O)_{1-10}-$, $-(CH_2CH_2O)_{1-10}-CH_2-$, $-(CH_2CH_2O)_{1-10}-CH_2-$, $-CH_2-(CHOH)_{1-6}-$, $-(CHOH)_{1-6}-CH_2-$, $-(CHOH)_{1-6}-$, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, $-(OCH_2CH_2)_{1-3}$, optionally substituted alicyclyl, and optionally substituted heteroalicyclyl,
each $R^4$ is independently selected from $C_1$-$C_{16}$ alkyl; and
each X is independently selected from $-OH$, $-J$, $-R^5J$, $-C(=O)-J$, $-C(=O)-CH_2-J$, $-NH-C(=O)-CH_2-J$, $-OR^5$, $-OR^6$, $-OR^7$, $-O$-mesyl, $-O$-tosyl, $-NH-C(=O)-CH_2-O$-mesyl, $-NH-C(=O)-CH_2-O$-tosyl, $-SH$, $-S-S$-t-butyl, $-SR^7$, $-SR^5$, $-S-S-R^8$, $-NH-C(=O)-R^9-S-S-R^8$, $-NH-C(=O)-CH_2-SH$, $-S(=O)_2-J$, $-NH-C(=O)-R^9-S-C(=O)-R^5$, $-NH_2$, $-NHR^5$, $-N(R^5)$ $R^5$, $-NHR^7$, $-NH$-Fmoc, $-NH$-Boc, N-(phthalimidyl), $-C(=O)$ H, $-C(=O)-R^5$, $NH-C(=O)-R^9-C(=O)-R^5$, $-C(=O)OH$, $NH-C(=O)-R^9-C(=O)OH$, $-N=C=S$, $-N=C=O$, $-C\equiv C-R^5$, $-N=N^+=N^-$, $-O-NH_2$, $-O-NH$-Fmoc, $-O-NH$-Boc, $-O-N$-$(Boc)_2$, $-O-N(-$phthalimidyl$)$, $-NH-C(=O)-R^9-O-NH$-Boc, $-NH-C(=O)-R^9-O-N$-$(Boc)_2$, $-NH-C(=O)-R^9-O-N(-$phthalimidyl$)$, $-NH-NH_2$, $-C(=O)-NH-NH_2$, $-NH-C(=O)-NH-NH_2$, $-NH-C(=S)-NH-NH_2$, -toluenesulfonylhydrazide, $-R^5-NH-C(=NH_2^+)-NH_2$, $-NH-C(=NH_2^+)-CH_2CH_2CH_2-SH$,

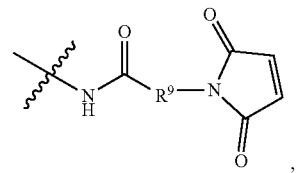

a diazirine, an optionally substituted trifluoromethylphenyldiazirine, an azide, an ester, a carbonate group, an ethyl vinyl, a maleimide, a vinylsulfone, an allyl sulfone, a thioester, an aziridine,
each $R^5$ is independently selected from hydrogen, $C_1$-$C_8$ alkyl, alicyclyl, heteroalicyclyl, benzyl, or aryl, wherein any ring in $R^5$ is optionally substituted;
each $R^6$ is independently selected from benzoyl, acetyl, benzyl, $C_1$-$C_8$ alkyl silyl, tetrahydropyranyl, tetrahydrofuranyl, and tetrahydrothiofuranyl;
each $R^7$ is independently selected from trityl, MMT, and DMT;
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each $R^9$ is independently selected from $C_1$-$C_{16}$ alkyl; and
each J is independently selected from Cl, Br, and I.
Optionally, L is a bond.
Preferably, n is 2. More preferably, m is also 2.
In some preferred embodiments, p is 0.
In another preferred embodiments, p is 1.
Optionally, B comprises one bifurcated monomer units $B_1$.

In another preferred embodiment, B comprises three bifurcated monomer units $B_1$.

In some preferred embodiments, X of $Z^2$ and $Z^3$ is the same and is selected from $-NH-C(=O)-CH_2-J$, $-NH-C(=O)-R^9-S-S-R^8$, $-NH-C(=O)-R^9-S-C(=O)-R^5$, $-NH_2$, $-NH-C(=O)-R^9-C(=O)-R^5$, $NH-C(=O)-R^9-(=O)OH$, $-O-NH_2$,

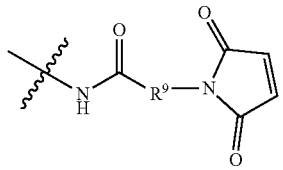

In another aspect, the invention generally relates to a conjugate having a chemical structure Formula (VII) or (VIII):

$M_1$-($L_1$-$B_1$-($L_1$-$M_2$)$q$)$r$         (VII), or $M_1$-($L_1$-B-($L_1$-$M_2$)$q$)$r$         (VIII)

wherein the conjugate is formed by a reaction of a molecule ($M_1$) with the X group of $Z^1$ of a bifurcated SA monomer unit $B_1$ or a dendrimer-like SA molecule B comprising two or more bifurcated SA monomer units $B_1$ and a reaction of one or several molecules ($M_2$) with one or several X groups of any of the $Z^2$ and $Z^3$ of a bifurcated SA monomer unit $B_1$ or a dendrimer-like SA molecule B comprising two or more bifurcated SA monomer units $B_1$, q is an integer selected from 1 to about 50;
r is an integer selected from 1 to about 50;
each $M_1$ is independently selected from the group consisting of a solid support, a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;
each $M_2$ is independently selected from the group consisting of a protein, an enzyme, an antibody, an antibody fragment, a polypeptide, an oligonucleotide, an oligonucleotide analog, a polysaccharide, a metabolite, a fluorescent compound, a chemiluminescent compound, a mass tag, a chromophore, biotin, a toxin, a drug, a chemotherapeutic agent, a cytotoxic agent, an immunosuppressive agent, a diagnostic agent, a radioligand, a chelating agent, and a small molecule;
each $L_1$ is independently selected from the group consisting of $R^{22}$ and a structure of $-V_{11}-R^{22}-V_{22}-$, wherein $V_{11}$ and $V_{22}$ are independently selected from the group consisting of a Diels-Alder adduct, a 1,3-dipolar adduct, $-C(R^4)(=N)-O-$, $-O-C(R^4)(=N)-$, $-S-CH_2-C(=O)-NH-$, $-NH-C(=O)-CH_2-S-$, $-C(=G^2)-G^1-$, $-G^1-C(=G^2)-$, $-G^3-$, $-G^1-C(=G^2)-G^1-$, $-S-S-$, $-S-(CH_2)_2-S(O)_2-$, $-S(O)_2-(CH_2)_2-S-$, $-S(O)_2-N(R^3)-$, $-N(R^3)-S(O)_2-$, $-C(O)-NH-NH-CH_2-$, $-C(O)-NH-N=CH-$, $-CH=N-NH-C(O)-$,
$-CH_2-NH-NH-C(O)-$, $-N(R^3)-S(O)_2-N(R^3)-$, $-C(O)-NH-CH(CH_2SH)-$, $-N=CH-$, $-NH-CH_2-$, $-NH-C(O)-CH_2-C(O)-NH-$, $-CH=N-G^4-$, $-CH_2-NH-G^4-$, $-G^4-NH-CH_2-$, $-G^4-N=CH-$, $-C(=NH_2)-NH-$, $-NH-C(=NH_2^+)-$, $-O-P(=O)(O^-)-NH-$, $-NH-P(=O)(O^-)-O-$, $-CH_2-CH(NH_2)-CH_2-S-$, $-S-CH_2-CH(NH_2)-CH_2-$, $-O-P(=O)(O^-)-O-$, $-O-P(=O)(S^-)-O-$, $-O-P(=S)(S^-)-O-$,

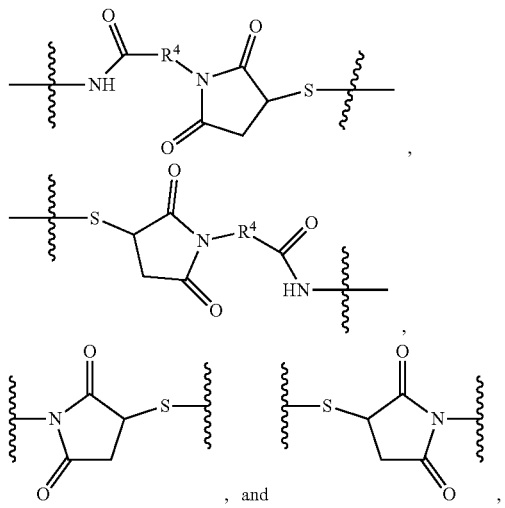

, and

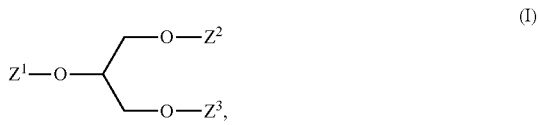

, wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^{22}$ is independently selected from a bond, $C_1$-$C_{12}$ alkyl, $-(CH_2CH_2O)_{1-10}-$, $-(CH_2CH_2O)_{1-10}-CH_2-$, $-CH_2-(CHOH)_{1-6}-$, $-CHOH)_{1-6}-CH_2-$, $-(CHOH)_{1-6}-$, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, $-(OCH_2CH_2)_{1-3}$, optionally substituted alicyclyl, and optionally substituted heteroalicyclyl;
each $R^4$ is independently selected from $C_1$-$C_{16}$ alkyl; and
each B comprising two or more bifurcated SA monomer units $B_1$, wherein each $B_1$ has the chemical structure Formula I:

(I)

$Z^1-O-\begin{matrix}O-Z^2\\O-Z^3\end{matrix}$, and each $B_1$ unit is bound to one or more other monomeric units through a linking group, W, formed by a reaction between the X group of the $Z^1$ unit and the X group of the $Z^2$ or $Z^3$ unit;

wherein
each of $Z^1$, $Z^2$, and $Z^3$ is independently

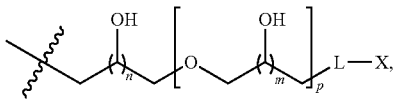

wherein
n is an integer selected from 2 to about 8;
m is an integer selected from 1 to about 8;
p is an integer selected from 0 to about 4;
each L and W is independently selected from the group consisting of a bond, $R^2$, and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—CH$_2$—C(=O)—NH—, —NH—C(=O)—CH$_2$—S—, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—, —CH=N-$G^4$-, —CH$_2$—NH-$G^4$-, -$G^4$-NH—CH$_2$—, -$G^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

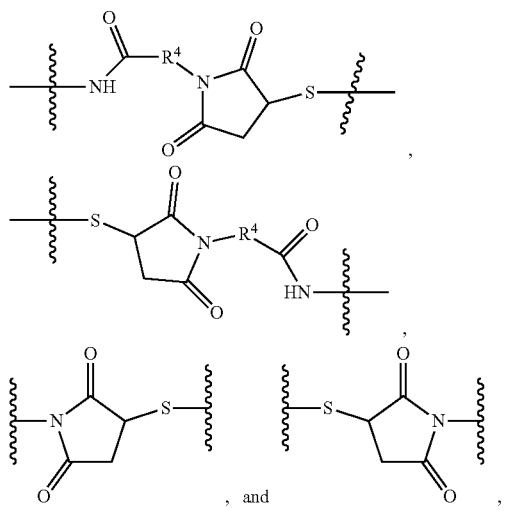

, and wherein
each $G^1$ is independently selected from N$R^3$, O, and S;
each $G^2$ is independently O or S;
each $G^3$ is independently selected from S, O, N$R^3$, and SO$_2$;
each $G^4$ is independently O or N$R^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, —(CH$_2$CH$_2$O)$_{1-10}$—CH$_2$—, —CH$_2$—(CHOH)$_{1-6}$—, —(CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl, and
each $R^4$ is independently selected from $C_1$-$C_{16}$ alkyl;
each X is independently selected from —OH, -J, —$R^5$J, —C(=O)-J, —C(=O)—CH$_2$-J, —NH—C(=O)—CH$_2$-J, —O$R^5$, —O$R^6$, —O$R^7$, —O-mesyl, —O-tosyl, —NH—C(=O)—CH$_2$—O-mesyl, —NH—C(=O)—CH$_2$—O-tosyl, —SH, —S—S-t-butyl, —S$R^7$, —S$R^5$, —S—S—$R^8$, —NH—C(=O)—$R^9$—S—S—$R^8$, —NH—C(=O)—CH$_2$—SH, —S(=O)$_2$-J, —NH—C(=O)—$R^9$—S—C(=O)—$R^5$, —NH$_2$, —NH$R^5$, —N($R^5$) $R^5$, —NH$R^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=N$^+$=N$^-$, —O—NH$_2$, —O—NH-Fmoc, —O—NH-Boc, —O—N-(Boc)$_2$, —O—N(-phthalimidyl), —NH—C(=O)—$R^9$—O—NH-Boc, —NH—C(=O)—$R^9$—O—N-(Boc)$_2$, NH—C(=O)—$R^9$—O—N(-phthalimidyl), —NH—NH$_2$, —C(=O)—NH—NH$_2$, —NH—C(=O)—NH—NH$_2$, —NH—C(=S)—NH—NH$_2$, -toluenesulfonylhydrazide, —$R^5$—NH—C(=NH$_2^+$)—NH$_2$, —NH—C(=NH$_2^+$)—CH$_2$CH$_2$CH$_2$—SH,

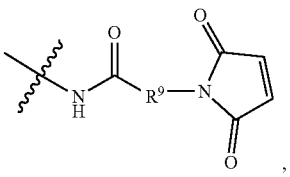

a diazirine, an optionally substituted trifluoromethylphenyldiazirine, an azide, an ester, a carbonate group, an ethyl vinyl, a maleimide, a vinylsulfone, an allyl sulfone, a thioester, an aziridine,
each $R^5$ is independently selected from hydrogen, $C_1$-$C_8$ alkyl, alicyclyl, heteroalicyclyl, benzyl, or aryl, wherein any ring in $R^5$ is optionally substituted;
each $R^6$ is independently selected from benzoyl, acetyl, benzyl, $C_1$-$C_8$ alkyl silyl, tetrahydropyranyl, tetrahydrofuranyl, and tetrahydrothiofuranyl;
each $R^7$ is independently selected from trityl, MMT, and DMT;
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each $R^9$ is independently selected from $C_1$-$C_{16}$ alkyl; and;
each J is independently selected from Cl, Br, and I.
Optionally, L is a bond.
Preferably, n is 2. More preferably, m is also 2.
In some preferred embodiments, p is 0.
In another preferred embodiments, p is 1.

Optionally, B comprises one bifurcated monomer units $B_1$.

In another preferred embodiment, B comprises three bifurcated monomer units $B_1$.

In another preferred embodiment, B comprises seven bifurcated monomer units $B_1$.

In one aspect, $M_1$ may be selected from the group consisting of polystyrene supports, polyamide supports, polyethylene glycol supports, polyacrylic supports, polyacrylic/beta-alanine copolymer supports, polyacrylamide/polystyrene copolymer supports, polyacrylamide/polyethylene glycol copolymer supports, polyethyleneglyco/polystyrene copolymer supports, controlled pore glass, agarose, dextran gel, polysaccharide based polymer, a polymeric microsphere, a latex microsphere, a polymeric particle consist of polystyrene, a polymeric particle consist of copolymers of styrene, poly(methyl methacrylate), polyvinyltoluene, poly(2-hydroxyethyl methacrylate), the copolymer of poly(2-hydroxyethyl methacrylate), poly(ethylene glycol dimethacrylate/2-hydroxyethylmetacrlate), poly(lactic-co-polycolic acid), inorganic constructs, metals, semiconductors, super paramagnetic composites, biodegradable constructs, synthetic dendrimers, dendrons, a quantum dot, a dye-coated particle, and a magnetic coated particle. Optionally, $M_1$ is an agarose bead. Alternatively, $M_1$ may be a magnetic coated particle.

$M_1$ or $M_2$ may comprise a radioactive isotope.

$M_1$ or $M_2$ may be selected from the group consisting of an oligonucleotide, oligonucleotide analog, or small interference RNA (siRNA). Examples of oligonucleotide analogs include peptide nucleic acids (PNAs), locked nucleic acids (LNAs), threose nucleic acid (TNA), and alpha PNAs.

In certain embodiments $M_1$ or $M_2$ is a biomolecule, a metabolite, a fluorescent compound, biotin, a toxin, a drug, a chemotherapeutic agent, a diagnostic agent, or other biologically active molecule.

In certain embodiments $M_1$ or $M_2$ may include one or more radioactive isotopes or isotopic elements.

In certain embodiments $M_2$ is a metabolite. Metabolites are the intermediates and products of metabolism. Examples of metabolites include alkaloids, glycosides, lipids, flavonoids, nonribosomal peptides, phenazines, phenols, polyketides, terpenes, and tetrapyrroles. Metabolites may also be fragments of drugs or drugs modified by living organisms through specialized enzymatic systems.

In some preferred embodiments $M_1$ and $M_2$ are therapeutic agents, such as a drug, toxin, cytokine, hormone, hormone antagonist, enzyme, enzyme inhibitor, inhibitory oligonucleotide (e.g., RNAi or siRNA), immunomodulator (e.g., cytokine, lymphokine, chemokine, growth factor, or tumor necrosis factor), radionuclide, anti-angiogenic agent, pro-apoptotic agent, antibody, radiolabeled antibody, or photoactive therapeutic agent.

In certain embodiments the therapeutic agent is a chemotherapeutic drug. Examples of chemotherapeutic drugs include adrenocortical suppressants, antimetabolites, alkylating agents, alkyl sulfonates, antibiotics, antimitotics, anthracyclines, anti-angiogenic agents, camptothecins, COX-2 inhibitors, CPT-11, doxorubicin, doxorubicin analogs, enzyme inhibitors, endostatin, epipodophyllotoxins, ethylenimine derivatives, folic acid analogs, gemcitabine, HDAC inhibitors, heat shock protein (HSP) 90 inhibitors, hormone antagonists, methotrexate, methyl hydrazine derivatives, mTOR inhibitors, nitrosoureas, nitrogen mustards, pyrimidine analogs, purine analogs, platinum coordination complexes, substituted ureas, SN-38, taxols, triazenes, taxanes, tyrosine kinase inhibitors, proteosome inhibitors, pro-apoptotic agents, and vinca alkaloids. Suitable chemotherapeutic agents are described in the literature (Remington's Pharmaceutical Sciences, 19th Ed. Mack Publishing Co. 1995; Goodman and Gilman's the Pharmacological Basis of Therapeutics, 7th Ed. McMillan Publishing Co. 1985).

In certain embodiments the therapeutic agent is a cytotoxic or immunosuppressive agent, such as an antitubulin agent, auristatin, DNA minor groove binder, DNA replication inhibitor, alkylating agent, anthracycline, antibiotic, antifolate, antimetabolite, chemotherapy sensitizer, cyclooxygenase inhibitor, duocarmycin, etoposide, fluorinated pyrimidine, ionophore, lexitropsin, lipoxygenase inhibitor, nitrosourea, platinol, pre-forming compound, purine antimetabolite, puromycin, radiation sensitizer, steroid, taxane, topoisomerase inhibitor, vinca alkaloid, and the like.

Individual cytotoxic agents include, for example, auristatin (e.g., MMAE, MMAF), azathioprine, bleomycin, bortezomib, busulfan, calicheamicin, capecitabine, carboplatin, carmustine, chlorambucil, cisplatin, cladribine, colaspase, cyclophosphamide, cytarabine, dacarbazine, dactinomycin, dauorubicin, docetaxel, doxorubicin, duocarmycin, epirubicin, etoposide, etoposide phosphate, fludarabine, fluorouracil, fotemustine, ganiclovir, gemcitabine, hydroxyurea, idarubicin, ifosfamide, irinotecan, lomustine, melphalan, mercaptopurine, methotrexate, mitomycin, mitozantrone, oxaliplatin, paclitaxel, premetrexed, procarbazine, raltitrexed, temozolomide, temiposide, thioguanine, thiotepa, topotecan, valganciclovir, vinblastine, vincristine, vinorebine, and maytansine (e.g., DM1, DM4). Drugs that have been conjugated to the antibody and are currently in clinical trials are auristatin, maytansine, calicheamicin, and duocarmycin (Alley S. C. et al. Curr Opin Chem Bio 2010, 14, 529-537).

In certain embodiments the cytotoxic agent is dolastatin (e.g., auristatin E, AFP, MMAF, MMAE) or derivatives thereof. In certain embodiments the cytotoxic agent is a conventional chemotherapeutic, such as doxorubicin, paclitaxel, melphalan, vinca alkaloids, methotrexate, mitomycin C, or etoposide. In addition, potent agents include CC-1065 analogs, calicheamicin, maytansine (or DM-1), analogs of dolastatin 10, rhizoxin, and palytoxin.

In certain embodiments the immunosuppressive agent may be, for example, arylcarboxylic derivatives, azathioprine, cyclosporine, cyclooxygenase inhibitors, cyclophosphamide, etanercept, gancyclovir, glucocorticoids or glucocorticoid analogs, leukotriene receptor antagonists, 5-lipoxygenase inhibitors, mycophenolate mofetil or methotrexate, nicotinic acid derivatives, oxicam derivatives, pyrazole-containing derivatives, rapamycin, or tacrolimus.

In some preferred embodiments the therapeutic agent is a toxin selected from the group consisting of ricin, abrin, alpha toxin, saporin, ribonuclease (RNase), DNase I, Staphylococcal enterotoxin A, pokeweed antiviral protein, gelonin, diphtheria toxin, *Pseudomonas* exotoxin, and *Pseudomonas* endotoxin.

In some preferred embodiments the therapeutic agent is an immunomodulator selected from the group consisting of cytokines, stem cell growth factors, lymphotoxins, hematopoietic factors, colony stimulating factor (CSF), interferons (IFNs), erythropoietin, thrombopoietin, and a combination thereof.

Each $M_1$ and $M_2$ may be any antibody or fragment that is capable of binding specifically to a target antigen associated with a disease state or condition. Antibody sequences or antibody-secreting hybridomas against almost any disease-associated antigen may be obtained from ATCC (American Type Culture Collection), NCBI, and USPTO databases. Useful polyclonal antibodies are heterogeneous populations of antibody molecules derived from the sera of immunized animals. Useful monoclonal antibodies are homogeneous populations of antibodies to a particular antigenic determinant of a target antigen. A polyclonal and monoclonal antibody to a target antigen may be prepared by using any technique known in the art.

Suitable antibodies include monoclonal antibodies, such as chimeric, humanized, or human antibodies, or an antigen-binding fragment thereof. In one embodiment the antibody fragment is, for example, AC10, BR96, 1F6 or 2F2, or growth inhibitory antibody.

Individual therapeutic antibodies include, for example, alemtuzumab (Campath; Leukosite, MA), Allomune (BioTransplant), bevacizumab (Avastin; Genetech, Inc., CA), CEAcide (Immunomedics, NJ), cetuximab (Erbitux; Imclone Systems Inc., NY), epratuzamab (Immunomedics, Inc., NJ and Amgen, CA), LymphoCide (Immunomedics, Inc., NJ), Oncolym (Techniclone, Inc., CA), OVARE (AltaRex Corporation, MA), Panorex (Glaxo Wellcome, NC), rituximab (Rituxan; Genetech), Smart MI95 (Protein Design Labs, Inc., CA), Smart ID10 (Protein Design Labs, Inc., CA), trastuzumab (Herceptin; Genetech), and Vitaxin (Med-Immune, Inc., MD).

In certain embodiments the antibodies include, for example, antibodies against the following antigens: tumor-associated antigens; antigens associated with pancreatic cancer, malignant disease, autoimmune disease, immune dysfunction disease, leukemia, or neurological disease; and antigens against transmembrane activator and CAML-interactor (TACI)(Yu et al. Nat Immunol 2000, 1, 252-256). Examples of antigens include: CA125, CA 15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, CEA, gp100, MART1, IL-2 receptor, CD4, CD5, CD8, CD14, CD15, CD19, CD20, CD21, CD22, CD23, CD25, CD33, CD37, CD38, CD40, CD40L, CD46, CD52, CD54, CD66a-d, CD67, CD74, CD79a, CD80, CD126, CD138, CD154, B7, MUC1, LALI, HM1.24, HLA-DR, tenascin, VEGF, PIGF, ED-B, fibronectin, oncogenes, oncogene products, necrosis antigens, T101, TAG, IL-6, MIF, TRAIL-R1 (DR8), TRAIL-R2 (DR5), human chorionic gonadotropin, mucin, P21, MPG, and Neu oncogene product.

The antibody can also be a multispecific antibody, such as a bispecific antibody. Methods for making bispecific antibodies are known in the art. In some embodiments the antibody fragment is an Fv, Fab, Fab', or F(ab')$_2$. Other useful antibodies are heavy chain and light chain dimers of antibodies, single chain antibodies, a minibody, a diabody, a triabody, a tetrabody, dsFv, sc-Fv-Fc, (sFv)$_2$, a fragment produced by a Fab expression library, an anti-idiotypic (anti-Id) antibody, or multispecific antibodies from antibody fragments.

In certain embodiments the antibody and proteins may comprise one or more radioactive isotopes useful for treating diseased tissue. Suitable therapeutic radionuclides include, but are not limited to, iodine-131, iodine-125, bismuth-212, bismuth-213, lutetium-177, yttrium-90, yttrium-88, technetium-99m, copper-62, copper-67, rhenium-188, rhenium-186, galium-66, galium-67, indium-111, indium-114m, indium-115, boron-10, astatine-211, phosphorus-32, phosphorus-33, scandium-47, silver-111, praseodymium-142, samarium-153, terbium-161, dysprosium-166, holmium-166, rhenium-186, rhenium-188, rhenium-189, lead-212, lead-211, radium-223, actinium-225, iron-59, selenium-75, arsenic-77, strontium-89, molybdenum-99, rhodium-105, palladium-109, praseodymium-143, promethium-149, erbium-169, iridium-194, gold-198, and gold-199.

Additional potential therapeutic radioisotopes include carbon-11, nitrogen-13, oxygen-15, bromine-75, bromine-76, gold-198, actinium-224, iodine-126, iodine-133, bromine-77, indium-113, ruthenium-95, ruthenium-97, ruthenium-103, ruthenium-105, mercury-107, mercury-203, tellurium-121m, tellurium-122m, tellurium-125m, tellurium-165, tellurium-167, tellurium-168, platinum-197, palladium-109, rhodium-105, praseodymium-142, praseodymium-143, terbium-161, holminum-166, gold-199, cobalt-57, cobalt-58, chromium-51, iron-59, selenium-75, thallium-201, actinium-225, ytterbium-169, and the like.

Therapeutic reagents may be attached to the antibody through partial reduction of the SH group or surface amines. Therapeutic reagents may also be attached to carbohydrate side chains if available.

In certain embodiments the therapeutic agents may include one or more copies of the same therapeutic agent or combinations of different therapeutic agents.

In certain embodiments each $M_1$ or $M_2$ is a diagnostic agent. Examples of diagnostic agents include fluorescent probes, chemiluminescent compounds, radio ligands, bifunctional chelating agents, lanthanide chelate, mass spectrometric tags, chromophores, and UV-active compounds.

In certain embodiments $M_1$ or $M_2$ is a fluorescent compound. Examples of fluorescent compounds include fluorescein, rhodamine, coumarin, green fluorescent protein, BODIPY, Texas Red, Cascade Blue, Lucifer yellow derivatives, phycobiliprotein cyanine dye, lanthanide chelate, and quantum dot. Various fluorescent compounds are commercially available (e.g., from Molecular Probes and Invitrogen).

The position at which $M_1$ or $M_2$ attaches to $B_1$ or B can be a single site or multiple sites. $M_1$ or $M_2$ can be attached to $B_1$ or B through an ester linkage or other crosslinking group.

In a preferred embodiment $M_1$ or $M_2$ is a bifunctional chelating agent. Examples of chelating agents include, but are not limited to, DOTA (1,4,7,10-tetraazacyclododecane-N,N',N'',N'''-tetraacetic acid), derivatives of DOTA, DTPA (diethylenetriamine pentaacetic anhydride), derivatives of DTPA, NOTA (1,4,7-trizazcyclononane-N,N',N''-triacetic acid), derivatives of NOTA, TETA (1,4,8,11-tetraazacyclotetradecane-N,N',N'',N'''-tetraacetic acid), derivatives of TETA, DTTA (N-(p-isothiocyanatobenzyl)-diethylenetriamine-N,N',N'',N'''-tetraacetic acid), derivatives of DTTA, deferoxamine, and deratives of deferoxiamine. Various bifunctional chelators are commercially available (e.g., from Macrocyclics, Inc.).

Preferably, $M_1$ or $M_2$ is a biotin.

In a more preferred embodiment $M_1$ or $M_2$ is a metal coordination complex formed between a metal ion with the bifunctional chelating agent. In some cases, the metal ion is radioactive. Preferably, the metal ion is non-radioactive. More preferably, the metal ion is a lanthanide. Most preferably, the metal is Europium or Terbium.

In a preferred embodiment $M_1$ or $M_2$ is a therapeutic protein or polypeptide. SA macromolecules may conjugate the protein or peptide at a single specific site or multiple sites. The therapeutic proteins may be cytokines, hormones, hemapoietic proteins, blood proteins, enzymes, or peptides.

Preferably, the amino acid sequence of the therapeutic protein contains at least 80% sequence homology to the wild-type therapeutic proteins selected from the group consisting of granulocyte macrophage colony stimulating factor, interferon, interferon alpha-2a, interferon alpha-2b, interleukin, interleukin-2, erythropoietin, growth hormone, human growth hormone, apomyoglobin, asparaginase, leptin, serum proteins, human chorionic gonadotropin, insulin, follicle stimulating hormone, luteinizing hormone, urate oxidase, adenosine deaminase, antibody fusion proteins, and factor VII. More preferably, the amino acid sequence of the therapeutic protein contains at least 90% sequence homology to the wild-type therapeutic proteins selected from the group consisting of granulocyte macrophage colony stimulating factor (GM-CSF), interferon, interferon alpha-2a (IFNα-2a), interferon alpha-2b (IFNα-2b), interleukin, interleukin-2, erythropoietin, growth hormone, human growth hormone, apomyoglobin, asparaginase, leptin, serum proteins, human chorionic gonadotropin, insulin, follicle stimulating hormone, luteinizing hormone, urate oxidase, adenosine deaminase, antibody fusion proteins, and factor VII.

In certain embodiments $M_1$ or $M_2$ is granulocyte colony-stimulating factor (G-CSF), its fragments, or modified derivatives. G-CSF is a 174-amino-acid glycosylated cytokine that stimulates the proliferation, survival, and differentiation of neutrophil granulocyte progenitor cells and mature neutrophils (Hill C. P. et al. Proc Natl Acad Sci 1993, 90, 5167-5171). G-CSF is rapidly eliminated from the blood. Modification of G-CSF with a single SA macromolecule may help stabilize the substance. PEGylated G-CSF has been marketed under the trade name Neulasta (Kinstler O. B. et al. Pharm Res 1996, 13, 996-1002).

In certain embodiments the therapeutic proteins are GM-CSF, IFNα-2a, IFNα-2b, IL-2 (Waldmann T. A. Nature Rev Immunol 2006, 6, 595-601), erythropoietin (EPO)(Macdougall I. C. Curr Hematol Rep 2005, 4, 436-440), growth hormone (GH)(Zundel M. and Peschke B. 2006, WO 2006/084888), human growth hormone (hGH)(Li C. H. Mol Cell Biochem 1982, 46, 31-41), or apomyoglobin (apoMb)(Evans S. V. et al. J Mol Biol 1990, 213, 885-897). Other examples of therapeutic proteins and peptides include asparaginase, interferons (e.g., IFN-α, -β, -γ), interleukins, leptin, serum proteins (e.g., factor VII, factor VIIa, factor VIII, factor IX, and factor X), human chorionic gonadotropin (HCG), insulin, follicle stimulating hormone (FSH), luteinizing hormone (LH), urate oxidase (uricase), adenosine deaminase (ADA), and antibody fusion proteins (e.g., tumor necrosis factor receptor (TNFR)/Fc domain fusion protein).

Other useful proteins include proteins that selectively localize in a particular tissue or region of the body. Examples of such proteins include transferrin, HS-glycoprotein, coagulation factors, serum proteins, O-glycoprotein, G-CSF, GM-CSF, M-CSF, EPO, and the like.

In some preferred embodiments $M_1$ or $M_2$ is a derivative of a therapeutic protein or peptide. For example, fragments of the proteins and chemically modified proteins (e.g., glycosylation, acylation, amino acid substitution). In some preferred embodiments $M_1$ or $M_2$ is a recombinant protein.

The present invention provides methods for synthesizing glycerol core sugar alcohol units as well as the methods for assembling the dendrimer-like sugar alcohol multimer. Both divergent methods and convergent methods can be used for assembling the dendrimer-like sugar alcohol multimer in solution. Preferably, the compound is assembled divergently by solid phase.

Depicted below is an embodiment of a general approach for synthesizing dendrimer-like sugar alcohol multimer using a divergent method by solid phase.

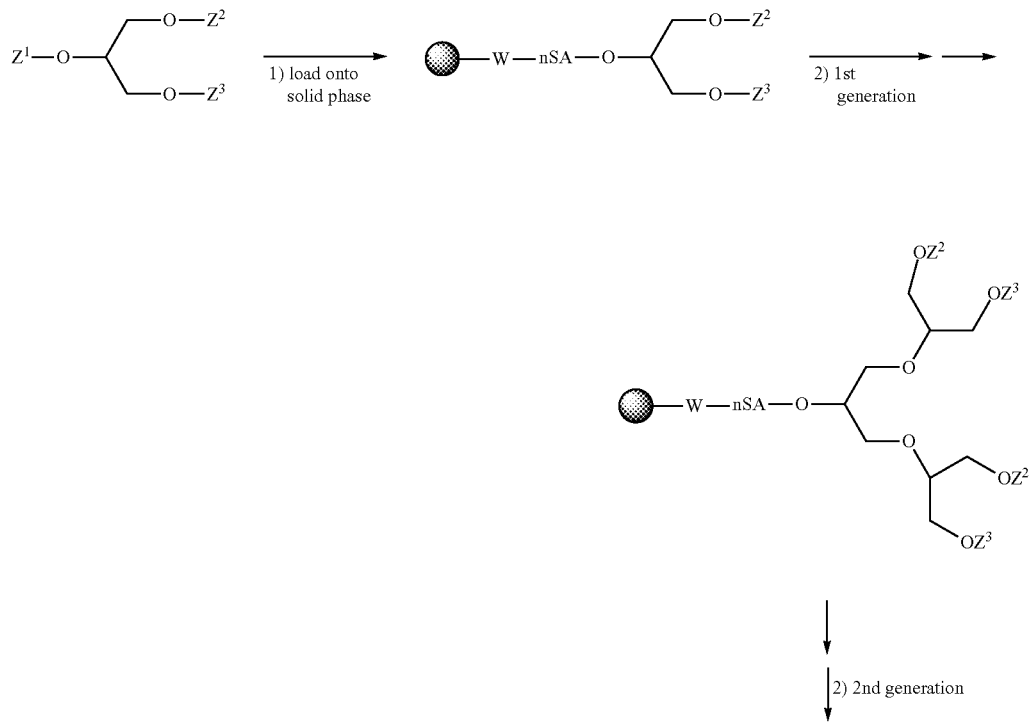

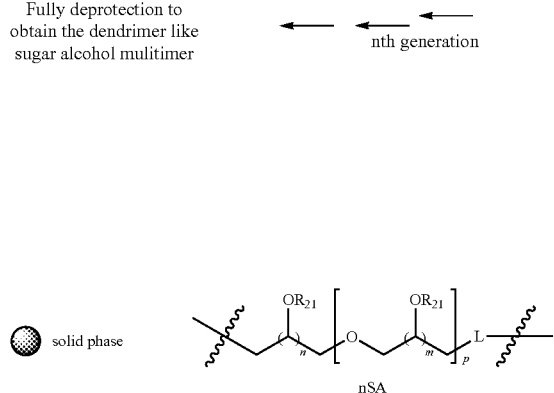

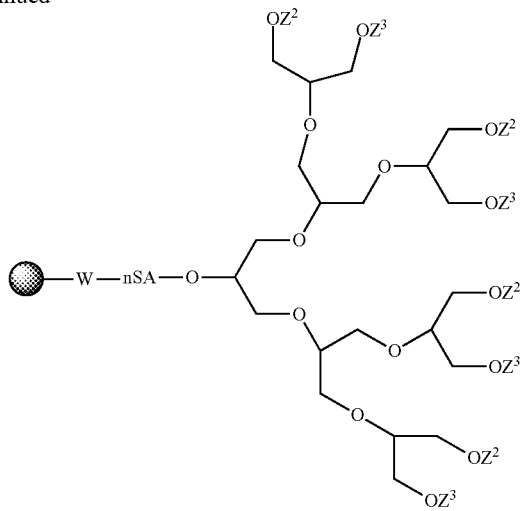

Fully deprotection to obtain the dendrimer like sugar alcohol mulitimer ← ← ← nth generation

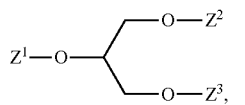 solid phase

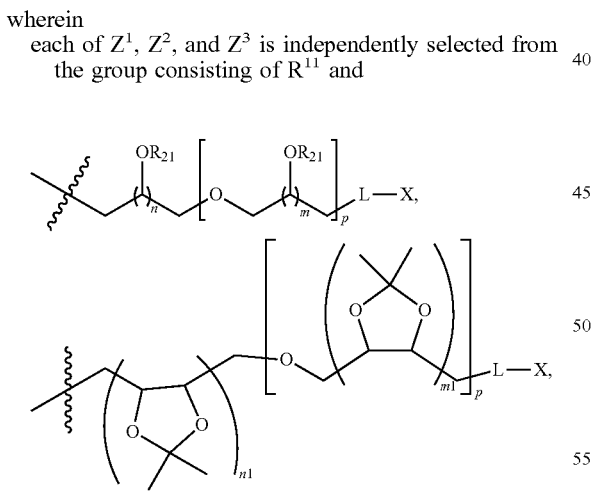

nSA

In one aspect, the invention a method for preparing a bifurcated SA monomer having a chemical structure of Formula I:

$$Z^1-O\diagup\begin{array}{c}O-Z^2\\O-Z^3,\end{array} \quad (I)$$

wherein
each of $Z^1$, $Z^2$, and $Z^3$ is independently selected from the group consisting of $R^{11}$ and and at least one of $Z^1$, $Z^2$, and $Z^3$ is not $R^{11}$;
each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;
n is an integer selected from 2 to about 8;
m is an integer selected from 1 to about 8;
p is an integer selected from 0 to about 50;
n1 is an integer selected from 1 to about 4;
m1 is an integer selected from 1 to about 4;
each L is independently selected from the group consisting of $R^2$ and a structure of $-V_1-R^2-V_2-$, wherein $V_1$ and $V_2$ are independently selected from the group consisting of a Diels-Alder adduct, a 1,3-dipolar adduct, $-C(R^4)(=N)-O-$, $-O-C(R^4)(=N)-$, $-S-CH_2-C(=O)-NH-$, $-NH-C(=O)-CH_2-S-$, $-C(=G^2)-G^1-$, $-G^1-C(=G^2)-$, $-G^3-$, $-G^1-C(=G^2)-G^1-$, $-S-S-$, $-S-(CH_2)_2-S(O)_2-$, $-S(O)_2-(CH_2)_2-S-$, $-S(O)_2-N(R^3)-$, $-N(R^3)-S(O)_2-$, $-C(O)-NH-NH-CH_2-$, $-C(O)-NH-N=CH-$, $-CH=N-NH-C(O)-$, $-CH_2-NH-NH-C(O)-$, $-N(R^3)-S(O)_2-N(R^3)-$, $-C(O)-NH-CH(CH_2SH)-$, $-N=CH-$, $-NH-CH_2-$, $-NH-C(O)-CH_2-C(O)-NH-$, $-CH=N-G^4-$, $-CH_2-NH-G^4-$, $-G^4-NH-CH_2-$, $-G^4-N=CH-$, $-C(=NH_2^+)-NH-$, $-NH-C(=NH_2^+)-$, $-O-P(=O)(O^-)-NH-$, $-NH-P(=O)(O^-)-O-$, $-CH_2-CH(NH_2)-CH_2-S-$, $-S-CH_2-CH(NH_2)-CH_2-$, $-O-P(=O)(O)-O-$, $-O-P(=O)(S^-)-O-$, $-O-P(=S)(S^-)-O-$,

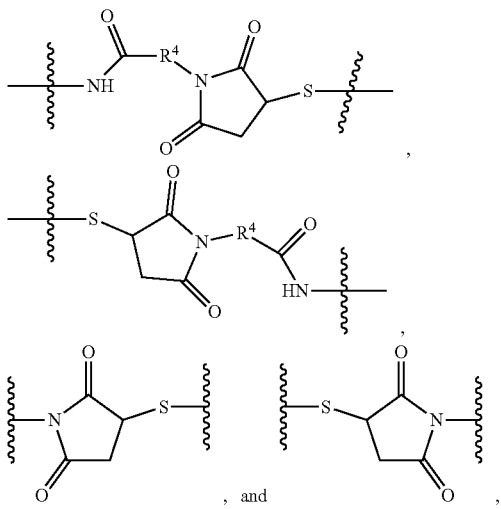

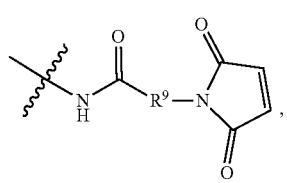

wherein
- each $G^1$ is independently selected from $NR^3$, O, and S;
- each $G^2$ is independently O or S;
- each $G^3$ is independently selected from S, O, $NR^3$, and $SO_2$;
- each $G^4$ is independently O or $NR^3$;
- each $R^2$ is independently selected from a bond, $C_1$-$C_{12}$ alkyl, —$(CH_2CH_2O)_{1-10}$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
- each $R^3$ is independently selected from hydrogen, $C_1$-$C_8$ alkyl, —$(OCH_2CH_2)_{1-3}$, optionally substituted alicyclyl, and optionally substituted heteroalicyclyl,
- each $R^4$ is independently selected from $C_1$-$C_{16}$ alkyl;
- each X is independently selected from —OH, -J, —$R^5J$, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —S(=O)$_2$-J, —NH—C(=O)—$R^9$—S—C(=O)—$R^5$, —$NH_2$, —$NHR^5$, —N($R^5$) $R^5$, —$NHR^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=$N^+$=$N^-$, —O—$NH_2$, —O—NH-Fmoc, —O—NH-Boc, —O—N-(Boc)$_2$, —O—N(-phthalimidyl), —NH—C(=O)—$R^9$—O—NH-Boc, —NH—C(=O)—$R^9$—O—N-(Boc)$_2$, NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, —NH—C(=$NH_2^+$)—$CH_2CH_2CH_2$—SH, a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$N^+H_2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;

- each $R^5$ is independently selected from hydrogen, $C_1$-$C_8$ alkyl, alicyclyl, heteroalicyclyl, benzyl, or aryl, wherein any ring in $R^5$ is optionally substituted;
- each $R^6$ is independently selected from benzoyl, acetyl, benzyl, $C_1$-$C_8$ alkyl silyl, tetrahydropyranyl, tetrahydrofuranyl, and tetrahydrothiofuranyl;
- each $R^7$ is independently selected from trityl, MMT, and DMT;
- each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
- each $R^9$ is independently selected from $C_1$-$C_{16}$ alkyl, and
- each J is independently selected from Cl, Br and I, wherein the method comprises:
(i) providing a glycerol;
(ii) combining the glycerol with reagents that can selectively protect the two terminal primary OH groups with $R^{23}$ to form an intermediate having a chemical structure of

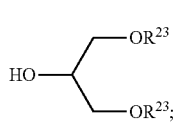

(II)

(iii) providing a first SA molecule with a free primary OH group and have a chemical structure of

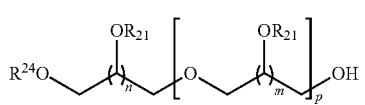

III or

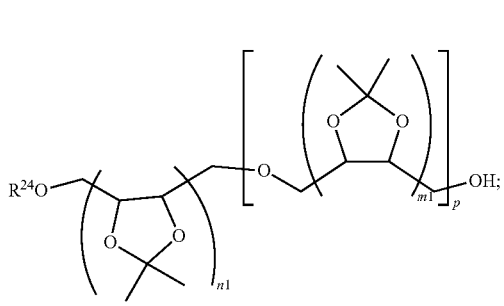

(iv) substituting the primary OH group of III or IV with good leaving group;
(v) combining the first SA molecule and glycerol under conditions that permit the condensation of these two units to form a bifurcated SA monomer;
(vi) removing one or both protecting groups ($R^{23}$) of the primary OH groups of glycerol of the bifurcated SA monomer;
(vii) providing a second SA molecule with a free primary OH group and have a chemical structure of

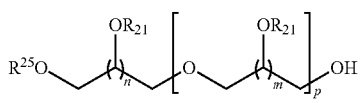

or

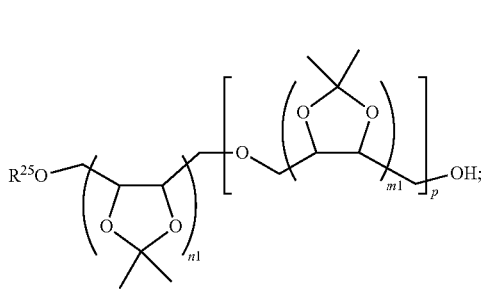

(viii) substituting the primary OH group of the second SA molecule with good leaving group;
(ix) combining the bifurcated SA monomer and one or two of the second SA molecules under conditions that permit the condensation of these two units to form a large bifurcated SA monomer;
(x) combining this bifurcated SA monomer with reagents that selectively deprotect $R^{24}$ or $R^{25}$ groups of the SA molecules; and
(xi) reacting further with reagents that allow introduction of linker (L) and different functional group X to form a bifurcated SA monomer having a chemical structure of formula

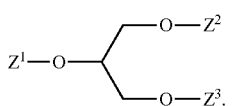

Optionally, each of $R_{21}$, $R^{23}$, $R^{24}$, and $R^{25}$ is independently selected from the group consisting of acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, C1 C8 alkyl silyl, methyl ethers, and ethoxyethyl ethers.

In another aspect, the invention provides a solid phase-based method for assembling a dendrimer-like SA molecule comprising two or more bifurcated SA monomer units, $B_1$, and each $B_1$ unit is bound to one or more other monomeric units through a linking group, W, formed by a reaction between the X group of the $Z^1$ unit and the X group of the $Z^2$ or $Z^3$ unit;

wherein
each $B_1$ has the chemical structure Formula I:

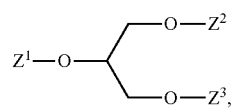

wherein
each of $Z^1$, $Z^2$, and $Z^3$ is independently selected from the group consisting of $R^{11}$ and

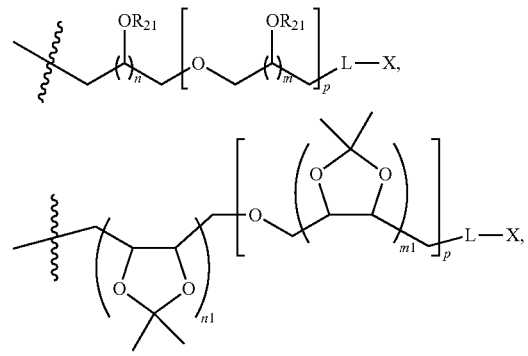

and at least one of $Z^1$, $Z^2$, and $Z^3$ is not $R^{11}$;
each $R^{11}$ is independently selected from hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;
$R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, acetonide of vicinal alcohol;
n is an integer selected from 2 to about 8;
m is an integer selected from 1 to about 8;

p is an integer selected from 0 to about 50;
n1 is an integer selected from 1 to about 4;
m1 is an integer selected from 1 to about 4;
each L and W is independently selected from the group consisting of a bond, $R^2$, and a structure of —$V_1$—$R^2$—$V_2$—, wherein $V_1$, and $V_2$ are independently selected from the group consisting of a Diels-Alder adduct, a 1,3-dipolar adduct, —C($R^4$)(=N)—O—, —O—C($R^4$)(=N)—, —S—$CH_2$—C(=O)—NH—, —NH—C(=O)—$CH_2$—S—, —C(=$G^2$)-$G^1$-, -$G^1$-C(=$G^2$)-, -$G^3$-, -$G^1$-C(=$G^2$)-$G^1$-, —S—S—, —S—$(CH_2)_2$—S$(O)_2$—, —S$(O)_2$—$(CH_2)_2$—S—, —S$(O)_2$—N($R^3$)—, —N($R^3$)—S$(O)_2$—, —C(O)—NH—NH—$CH_2$—, —C(O)—NH—N=CH—, —CH=N—NH—C(O)—, —$CH_2$—NH—NH—C(O)—, —N($R^3$)—S$(O)_2$—N($R^3$)—, —C(O)—NH—CH($CH_2$SH)—, —N=CH—, —NH—$CH_2$—, —NH—C(O)—$CH_2$—C(O)—NH—, —CH=N-$G^4$-, —$CH_2$—NH-$G^4$-, -$G^4$-NH—$CH_2$—, -$G^4$-N=CH—, —C(=$NH_2^+$)—NH—, —NH—C(=$NH_2^+$)—, —O—P(=O)($O^-$)—NH—, —NH—P(=O)($O^-$)—O—, —$CH_2$—CH($NH_2$)—$CH_2$—S—, —S—$CH_2$—CH($NH_2$)—$CH_2$—, —O—P(=O)($O^-$)—O—, —O—P(=O)($S^-$)—O—, —O—P(=S)($S^-$)—O—,

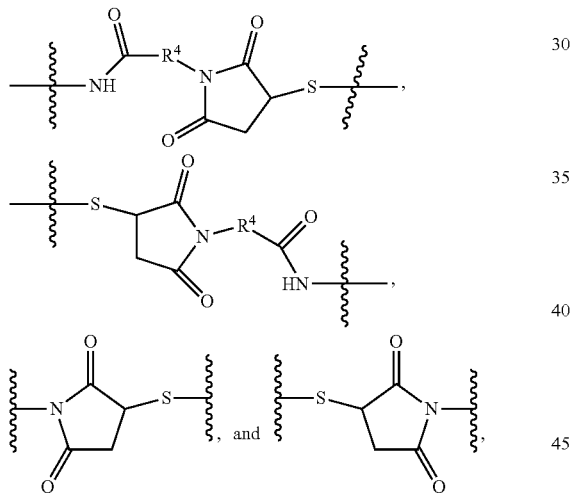

wherein
each $G^1$ is independently selected from $NR^3$, O, and S;
each $G^2$ is independently O or S;
each $G^3$ is independently selected from S, O, $NR^3$, and $SO_2$;
each $G^4$ is independently O or $NR^3$;
each $R^2$ is independently selected from a bond, $C_1$-$C_{12}$ alkyl, —$(CH_2CH_2O)_{1-10}$—, —$(CH_2CH_2O)_{1-10}$—$CH_2$—, —$(CH_2CH_2O)_{1-10}$—$CH_2$—, —$CH_2$—$(CHOH)_{1-6}$—, —$(CHOH)_{1-6}$—$CH_2$—, —$(CHOH)_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —$(OCH_2CH_2)_{1-3}$, optionally substituted alicyclyl, and optionally substituted heteroalicyclyl, and each $R^4$ is independently selected from $C_1$-$C_{16}$ alkyl;
each X is independently selected from —OH, -J, —$R^5$J, —C(=O)-J, —C(=O)—$CH_2$-J, —NH—C(=O)—$CH_2$-J, —$OR^5$, —$OR^6$, —$OR^7$, —O-mesyl, —O-tosyl, —NH—C(=O)—$CH_2$—O-mesyl, —NH—C(=O)—$CH_2$—O-tosyl, —SH, —S—S-t-butyl, —$SR^7$, —$SR^5$, —S—S—$R^8$, —NH—C(=O)—$R^9$—S—S—$R^8$, —NH—C(=O)—$CH_2$—SH, —S(=O)$_2$-J, —NH—C(=O)—$R^9$—S—C(=O)—$R^5$, —$NH_2$, —$NHR^5$, —N($R^5$) $R^5$, —$NHR^7$, —NH-Fmoc, —NH-Boc, N-(phthalimidyl), —C(=O) H, —C(=O)—$R^5$, NH—C(=O)—$R^9$—C(=O)—$R^5$, —C(=O)OH, NH—C(=O)—$R^9$—C(=O)OH, —N=C=S, —N=C=O, —C≡C—$R^5$, —N=$N^+$=$N^-$, —O—$NH_2$, —O—NH-Fmoc, —O—NH-Boc, —O—N-(Boc)$_2$, —O—N(-phthalimidyl), —NH—C(=O)—$R^9$—O—NH-Boc, —NH—C(=O)—$R^9$—O—N-(Boc)$_2$, NH—C(=O)—$R^9$—O—N(-phthalimidyl), —NH—$NH_2$, —C(=O)—NH—$NH_2$, —NH—C(=O)—NH—$NH_2$, —NH—C(=S)—NH—$NH_2$, -toluenesulfonylhydrazide, —$R^5$—NH—C(=$NH_2^+$)—$NH_2$, —NH—C(=$NH_2^+$)—$CH_2CH_2CH_2$—SH,

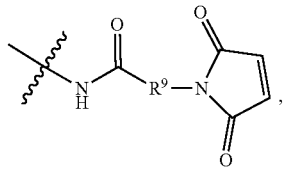

a benzophenone, an aryl diazonium, a diazoalkane, a diazoacetyl, an anthraquinone, a diazirine, an optionally substituted trifluoromethylphenyldiazirine, a diene, a dienophil, a 1,3-dipole, a dipolarophile, an alkene, a ketene, an olefin, an alkene with allylic hydrogen, a dicarbonyl group, an epoxide, an oxirane, an organosilane, a phosphonium group, an ester, an anhydride, a carbonate group, a glyoxal, —C(=$N^+H_2$)—O—$R^5$, a hydroxymethyl phosphine derivative, an ethyl vinyl, a maleimide, a vinylsulfone, an allyl sulfone, a thioester, a cisplatin derivative, an aziridine, an acryloyl group;
each $R^5$ is independently selected from hydrogen, $C_1$-$C_8$ alkyl, alicyclyl, heteroalicyclyl, benzyl or aryl, wherein any ring in $R^5$ is optionally substituted;
each $R^6$ is independently selected from benzoyl, acetyl, benzyl, $C_1$-$C_8$ alkyl silyl, tetrahydropyranyl, tetrahydrofuranyl, and tetrahydrothiofuranyl;
each $R^7$ is independently selected from trityl, MMT, and DMT;
each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each $R^9$ is independently selected from $C_1$-$C_{16}$ alkyl; and
each J is independently selected from Cl, Br, and I,
wherein the method comprises:
(i) providing a solid phase support, wherein solid phase is a commercial polystyrene resin that functioned with any of the following functional group: 4-benzyloxybenzyl alcohol, trityl alcohol, 2-chlorotrityl chloride, trityl chloride, 4-methylotrityl chloride, 4-methoxytrityl chloride, 4-(4-hydroxymethyl-3-methoxyphenoxy) butyryl MBHA, 4-(2'4'-dimethoxyphenylhydroxymethyl) phenoxy, 4-(4-hydroxymethyl-3-methoxyphenoxy) butyryl BHA, 4-hydroymethylbenzoyl MBHA, 4-(4-hydroxymethyl-3-methoxyphenoxy) butyryl MBHA, HMBA AM, TentaGel S PHB, Tentagel S HMBA, 4-hydroxymethylphenoxyacetyl AM, alcohol, ketone, amine, aminomethyl, carbonate, carboxylic acid, thiol, photocleavable;

(ii) providing a first bifurcated SA monomer having a chemical structure of (I)

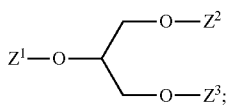

wherein X group of $Z^1$ is selected from the group consisting of —OH, —NH$_2$, —ONH$_2$, —COOH;

(iii) combining solid phase with the first bifurcated SA monomer unit under conditions that permit the attachment of the first bifurcated SA monomer unit onto resin;

(iv) conducting reactions on solid support to activate the X group of $Z^2$ or $Z^3$, or to introduce extra linker or linking group;

(v) providing a second bifurcated SA monomer unit having a chemical Juuviure vi

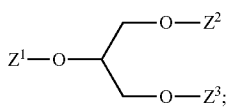

(I)

(vi) combining the solid phase with the second bifurcated SA monomer unit under conditions that permit the condensation of one or two of the second bifurcated SA monomer units with the first bifurcated SA monomer unit;

(vii) repeating steps iv to vi to generate higher order dendrimer; and (viii) once the desired dendrimer is achieved, cleaving the dendrimer from the solid support to release the dendrimer-like SA molecule.

In a preferred embodiment, the first bifurcated SA monomer is attached to the resin via an amine group.

In another preferred embodiment, the first bifurcated SA monomer is attached to the resin via an aminooxy group.

In another preferred embodiment, the first bifurcated SA monomer is attached to the resin via a OH group.

In some preferred embodiment, the solid phase is selected from 2-chlorotrityl chloride resin, trityl chloride resin, 4-methylotrityl chloride resin and 4-methoxytrityl chloride resin.

EXAMPLES

The following examples contain important additional information, exemplification, and guidance that can be adapted to the practice of this invention in its various embodiments and equivalents thereof. Practice of the invention will be more fully understood from the following examples, which are presented here for illustrative purposes only and should not be construed as limiting in anyway.

Instrumentation: $^1$H-NMR spectra were recorded at 500 MHz (Brukar) and are reported in parts per million (ppm) on the δ scale relative to residual CHC$_3$ (δ 7.25) and DMSO-d$_6$ (δ 2.49). All NMR experiments were performed at room temperature (RT) unless otherwise stated. HPLC was performed in an Agilent 1100 HPLC system with automatic sample injector and diode array detector. Analytical HPLC was performed on an XTerra™ C18 column (Waters, 2.5 µm, 3.0×30 mm). The HPLC method used (method A) was a linear gradient of AB solvent (5% B to 95% B in 10 minutes) at a flow rate of 0.6 mL/min. In the case of very hydrophobic compounds, a Nova-Pack C18 column (Waters, 5 µm, 3.9×150 mm) was used with a linear AB gradient (10% B to 95% B in 10 minutes, then held at 95% B for another 5 minutes) at a flow rate of 1.0 mL/min (method B). Solvent A was 0.1% aqueous TFA and solvent B was 0.1% TFA in acetonitrile. The UV detector was set at 210 nm and 254 nm. Most mass spectra were collected on a Quadrupole MDS Sciex Q-TRAP. In a typical experiment, crude or purified samples were dissolved or diluted in methanol containing 0.1% formic acid and infused directly into the electrospray inlet. For some large molecular weight compounds, mass spectra were collected on a 4700 Proteomic Analyzer with TOF/TOF optics (AB Sciex, Framingham). In a typical experiment, 5 µL of sample solution was mixed with 5 µL of 1 mg/mL dihydroxy benzoic acid solution in water, and then 1 µL of the mixture was spotted onto the MALDI plate and air dried. The sample either co-crystallized or formed a dried droplet with a matrix. Upon laser excitation, the matrix absorbs the laser energy and transfers the energy to the sample, facilitating its ionization and vaporization.

Solvents and Reagents: All moisture-sensitive reactions were performed in an inert, dry atmosphere of nitrogen. Reagent grade solvents were used for chromatography and extraction. N-hydroxyphthalimide was purchased from TCI America. 5% palladium on carbon, acetic anhydride, formic acid, anhydrous dichloromethane, anhydrous N,N-dimethylformamide (DMF), diethylazodicarboxylate (DEAD), diphenyl phosphoryl azide (DPPA), and triphenyl phosphine were purchased from Sigma-Aldrich. N-(9-fluorenylmethoxycarbonyloxy) succinimide ("Fmoc-OSu") was purchased from Chem-Impex International. Triethylamine was purchased from Mallinckrodt. Pyridine was purchased from EMD. ACS grade solvents were purchased from EMD, BDH, Macron, or Mallinckrodt. All other chemicals and reagents were purchased from Alfa Aesar and used as received.

Chromatography: Thin-layer chromatography (TLC) was performed using EMD TLC silica gel 60 F$_{254}$ (0.25 mm thickness). The plates were visualized by UV illumination, followed by charring with chemical solutions. Different charring solutions were used: 1) 3% phosphomolybdic acid (PMA) in ethanol (w/v); 2) ceric ammonium molybdate (CAM)(2.5% ammonium molybdate and 1% cerium sulfate in 10% aqueous sulfuric acid); 3) 5% ninhydrin in ethanol; and 4) 2% KMnO$_4$ in water. Flash chromatography was performed on an ISCO companion using pre-packed columns. The solvent compositions were on a volume/volume (v/v) basis.

A. Examples of Bifurcated SA Monomers

Example 1: Synthesis of Bifurcated SA Monomers: 1A1 and 1A2

The following shows an example of the synthesis of bifurcated SA monomers wherein X of the $Z^1$ is a —OBn and $Z^2$ and $Z^3$ is $R^{11}$ (TBDMS or hydrogen).

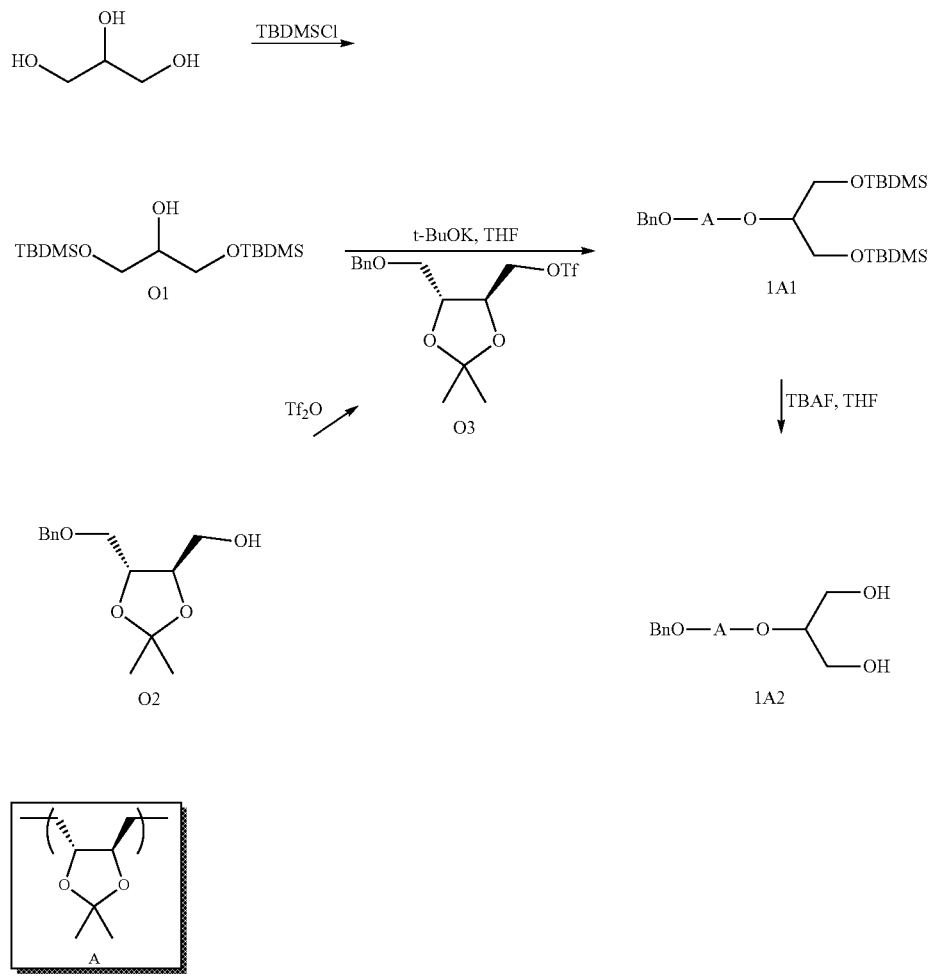

Synthesis of O1: Glycerol (2.0 g, 21.72 mmol) was added to a flask containing NaH (60% dispersion, 1.78 g, 44.54 mmol) in 20 mL dry THF at −10° C. After a half hour, tert-butyldimethylsilyl chloride (TBDMSCl)(6.7 g, 44.54 mmol) was added. The reaction was warmed to RT overnight and concentrated down. The oily residue was dissolved in dichloromethane (DCM) and washed 3 times with brine. The organic layer was then dried over anhydrous $Na_2SO_4$, filtered, concentrated, and purified by silica gel flash chromatography to obtain 4.43 g of desired product (64% yield). MS confirms the structure (ESI-MS obtained: M+Na=343).

Synthesis of O3: DCM (20 mL) and pyridine (0.85 mL) were added to a flask containing O2 (synthesized following previous protocol from U.S. Pat. No. 9,907,079B2)(1.9 g, 7.53 mmol). The reaction was cooled to below −80° C., and 9.4 mL of triflic anhydride was added. The reaction was left stirring for 45 minutes and then warmed to −15° C. and used directly for the next reaction (assuming quantitative yield).

Synthesis of 1A1: THF was added to a flask containing O1 (2.4 g, 7.49 mmol), followed by 1M potassium tert-butoxide in THF (7.485 mL). After stirring for 20 minutes, O3 was added. The reaction was left stirring at RT overnight. The reaction was concentrated, extracted with DCM, and washed with brine. The organic layer was then dried over anhydrous $Na_2SO_4$, filtered, concentrated, and purified by silica gel flash chromatography to obtain 3.95 g of desired product (95% yield). MS confirms the structure (ESI-MS obtained: M+Na=577).

Synthesis of 1A2: A1 (4.83 g, 8.7 mmol) was dissolved in THF and tetrabutylammonium fluoride (TBAF) monohydrate (5.59 g, 20 mmol) added slowly. After stirring overnight, the reaction mixture was concentrated and diluted with DCM. The organic layer was washed with water and then dried over anhydrous $Na_2SO_4$, filtered, concentrated, and purified by silica gel flash chromatography to obtain 1.95 g of desired product (68.7% yield). MS confirms the structure (ESI-MS obtained: M+Na=349).

Example 2: Synthesis of Benzyl-Protected Bifurcated SA Monomers (2A1-2A5)

The following shows an example of the synthesis of benzyl-protected bifurcated SA monomers wherein X of the $Z^1$ is a —OBn or —OH and X of $Z^2$ and $Z^3$ is selected from the groups consisting of —OTBDMS, —OH, —N=$N^+$=$N^-$, —N(-phthalimidyl), NH-Fmoc, and —$NH_2$.

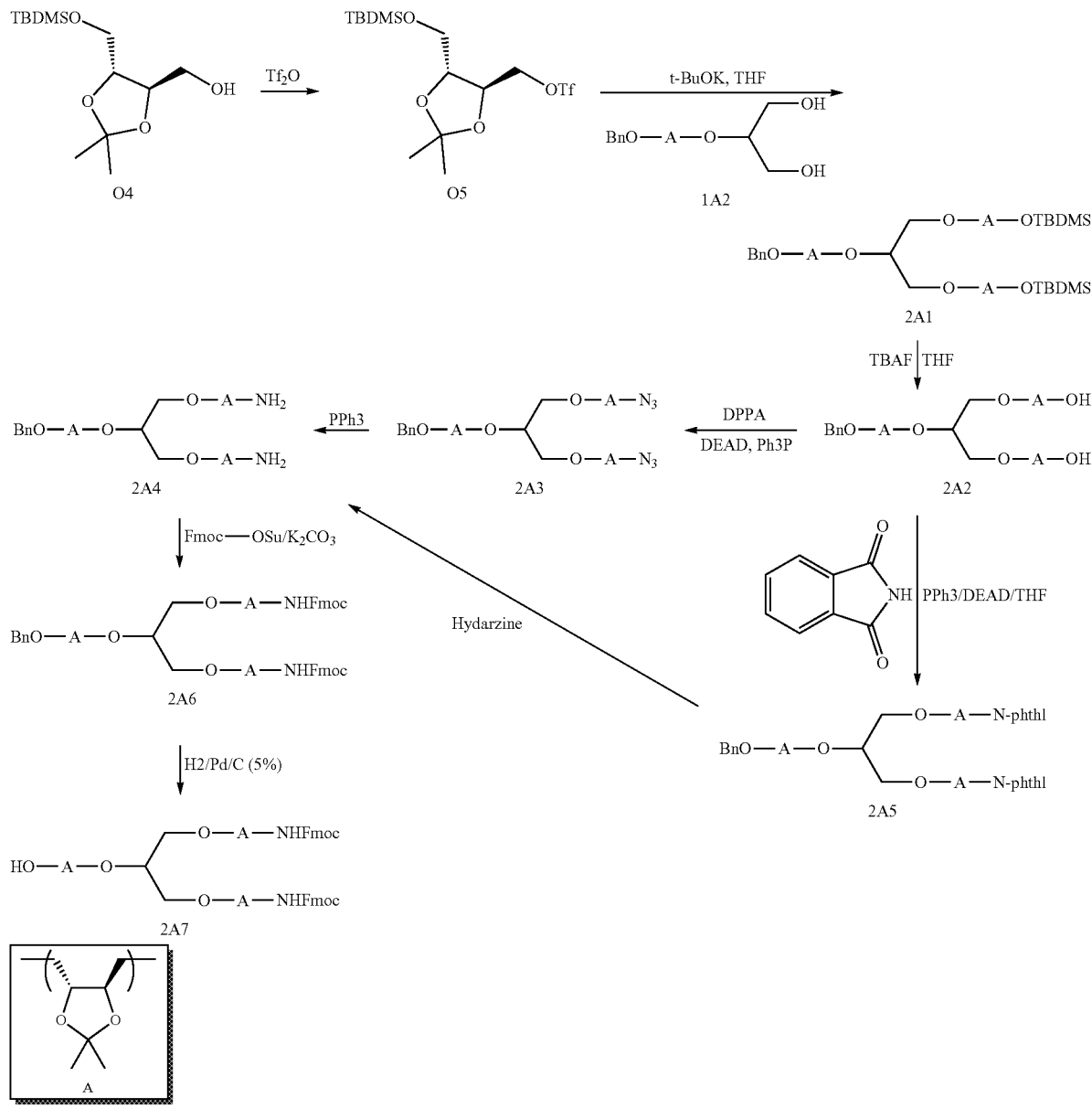

Scheme 2

Synthesis of O5: O5 was synthesized from O4 (prepared following previous protocol from U.S. Pat. No. 9,907,079B2) following the same procedure as O3 using triflic anhydride as the activating reagent. The reaction mixture was used directly for the next reaction (assuming quantitative yield).

Synthesis of 2A1: 2A1 was prepared by condensing O5 and 1A2 in the presence of tBuOK following the same procedure as 1A1. Starting with 47 mg of 1A2, silica gel flash chromatography purification afforded 45 mg of the product (37% yield). MS confirms the structure (MALDI-MS obtained: M+Na=866.7).

Synthesis of 2A2: The TBDMS protecting groups of 2A2 were removed by TBAF following the same procedure as 1A2. Silica gel flash chromatography afforded 0.286 g of the product (61% yield). MS confirms the structure (ESI-MS obtained: M+Na=637).

Synthesis of 2A3: THF was added to a flask containing 2A2 (0.20 g, 0.325 mmol) and triphenylphosphine (0.18 g, 0.781 mmol). The flask was cooled to below 0° C. 134 μL (0.781 mmol) of diethylazodicarboxylate (DEAD) was added, followed by diphenyl phosphoryl azide (DPPA) (0.147 mL, 0.781 mmol). The flask was warmed to RT and left stirring overnight. The reaction mixture was concentrated down, dissolved in DCM, and washed with saturated sodium bicarbonate. Organic fractions were combined, dried over sodium sulfate, filtered, concentrated, and purified by silica gel flash chromatography to afford 0.101 mg of the product (47% yield). MS confirms the structure (ESI-MS obtained: M+Na=687).

Synthesis of 2A4: Triphenylphosphine (0.319 g, 1.21 mmol) in water (0.164 mL, 9.11 mmol) was added to a flask containing 2A3 (101 mg, 0.152 mmol) in THF. After sitting overnight, the reaction mixture was concentrated down, and then diluted with DCM. The organic layer was washed with water, separated, and then dried over anhydrous sodium sulfate, filtered, concentrated, and the crude product used directly in the next step without further purification. MS confirms the structure (ESI-MS obtained: M+H=613).

Synthesis of 2A5: THF was added to a flask containing 2A2 (0.5 g, 0.813 mmol), triphenylphosphine (0.96 g, 3.66 mmol), and phthalimide (0.5385 g, 3.66 mmol). The flask was cooled to below 0° C. 766 μL (4.88 mmol) of DEAD was added. The flask was warmed to RT and left stirring overnight. The reaction mixture was concentrated down, dissolved in DCM, and washed with saturated sodium bicarbonate. Organic fractions were combined, dried over sodium sulfate, filtered, concentrated, and purified by silica gel flash chromatography to afford 0.724 g of the product (100% yield). MS confirms the structure (MALDI-MS obtained: M+Na=896.22).

Synthesis of 2A4 from 2A5: 2A5 (0.628 g, 0.72 mmol) was dissolved in MeOH (~7 mL), and then hydrazine monohydrate (351 μL, 7.2 mmol) was added. The reaction was stirred for 15 minutes. TLC shows the reaction was completed. The solvent was removed under vacuum and the obtained product used directly for the next reaction without any further purification (quantitative yield). MS confirms the structure (MALDI-MS obtained: M+H=614.2).

Synthesis of 2A6: Fmoc-OSu (0.534 g 1.584 mmol) and potassium carbonate (0.219 g, 2.584 mmol) were added to a flask containing 2A4 (0.441 g, 0.72 mmol) in 18 mL of a DMF/water (3:1) mixture. The reaction mixture was stirred at RT for 30 minutes. A large excess of water was added to precipitate the product. The product was used directly for the next reaction. MS confirms the structure (MALDI-MS obtained: M+K=1095.5).

Synthesis of 2A7: Ethyl acetate (0.3 mL) was added to a flask containing 2A6 (41 mg, 0.039 mmol). The reaction mixture was flushed with nitrogen and then palladium on carbon (5%, 8.1 mg) added. The mixture was stirred under a hydrogen atmosphere at RT for overnight. The reaction mixture was filtered, and the filtrate was dried under vacuum to afford 41 mg of the product (89% yield).

Example 3: Synthesis of Amine Bifurcated SA Monomers (3A1-3A3)

The following shows an example of bifurcated SA monomers wherein X of the $Z^1$ is selected from the group consisting of —OH, —N=N$^+$=N$^-$, —NH$_2$, and N(-phthalimidyl), and X of $Z^2$ and $Z^3$ is —OTBDMS.

Scheme 3

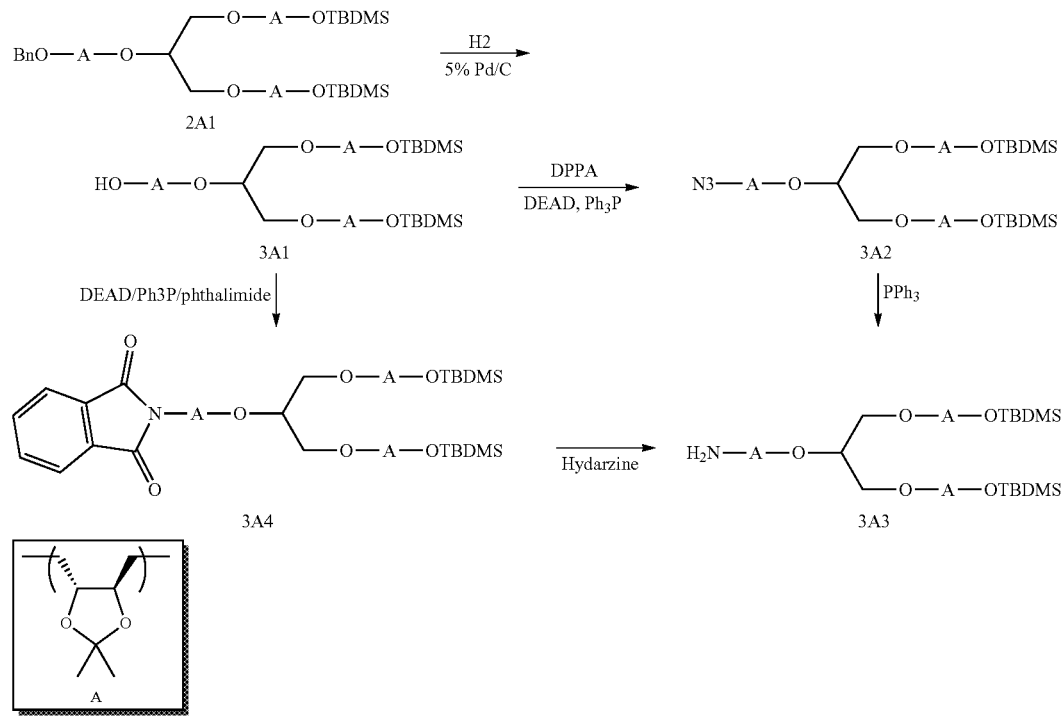

Synthesis of 3A1: Ethyl acetate (~4 mL) was added to a flask containing 2A1 (0.5 g, 0.593 mmol). The reaction mixture was flushed with nitrogen and then palladium on carbon (5%, 37 mg) added. The mixture was stirred under a hydrogen atmosphere at RT overnight. The reaction mixture was filtered, and the filtrate was dried under vacuum to afford 0.383 g of the product (82% yield). MS confirms the structure (ESI-MS obtained: M+H=752.9).

Synthesis of 3A2: The OH groups of 3A1 are converted directly to the azide groups using DPPA and DEAD following the same procedure as 2A3.

Synthesis of 3A3: The azide groups of 3A2 are reduced to the amino groups by triphenylphosphine following the same procedure as 2A4.

Synthesis of 3A4: 3A4 was prepared following the same procedure as 2A5. Starting with 116 mg of 3A1, silica gel flash chromatography afforded 131.9 mg of the product (97% yield). MS confirms the structure (ESI-MS obtained: M+H=883.04).

Synthesis of 3A3 from 3A4: 3A3 was prepared following the same deprotection protocol of 2A5 using hydrazine monohydrate as the deprotection reagent. Starting from 105 mg of 3A4, after deprotection and removing the solvent under vacuum, 58 mg of the product was obtained (74% yield). MS confirms the structure.

Example 4: Synthesis of Aminooxy Bifurcated SA Monomers (4A1, 4A2)

The following shows an example of bifurcated SA monomers wherein X of the $Z^1$ is —$ONH_2$ or —O—N(-phthalimidyl), and X of $Z^2$ and $Z^3$ is —OTBDMS.

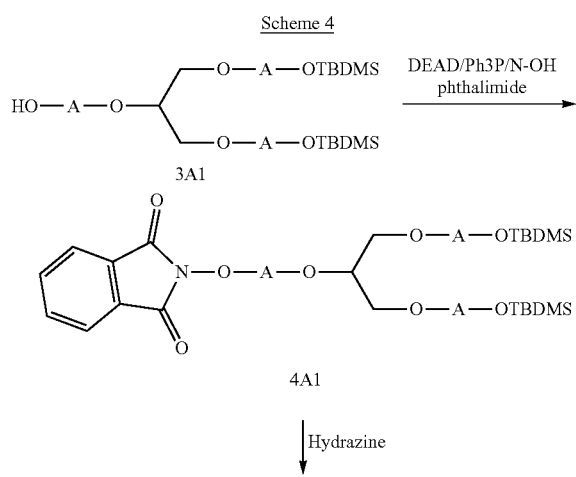

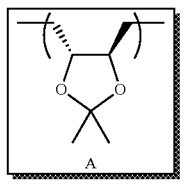

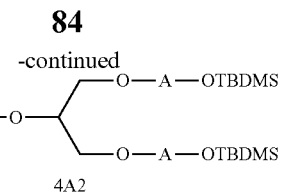

Synthesis of 4A1: 4A1 was prepared following the same procedure as 2A5 with the same equivalent of N-hydroxy phthalimide used instead of phthalimide. Starting with 0.125 g of 3A1, silica gel flash chromatography afforded 0.14 g of the product (94% yield). MS confirms the structure (ESI-MS obtained: M+H=899.06).

Synthesis of 4A2: The phthalimide groups of 4A1 were removed by hydrazine following the same procedure as 2A5. The solvent was removed under vacuum to afford 82.8 mg of the product (84% yield).

Example 5: Synthesis of Acetyl-Protected Bifurcated SA Monomers (5A1-5A4)

The following shows an example of bifurcated SA monomers wherein X of the $Z^1$ is selected from a group consisting of —OBn, —OH, and —OTBDMS, wherein $Z^2$ and $Z^3$ is $R^{11}$ (acetyl or hydrogen).

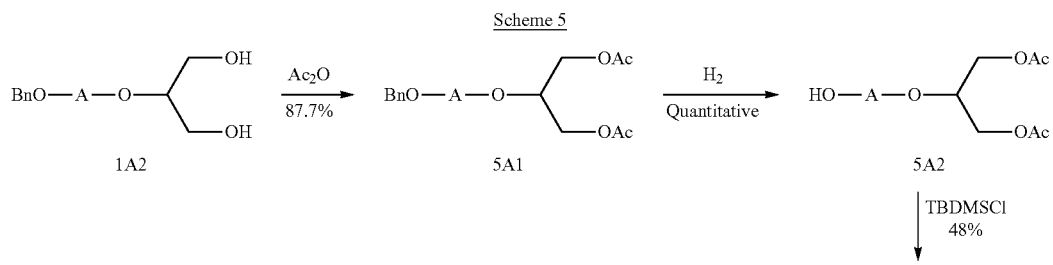

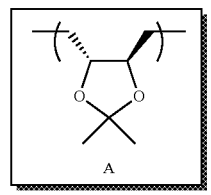

Synthesis of 5A1: DIPEA (3.2 mL) and DMAP (22 mg, 11.03 mmol) were added to a solution of 1A2 (1.20 g, 3.68 mmol) in 20 mL of DCM. After stirring at RT for a few minutes, 1.04 mL of acetic anhydride was added. After left stirring overnight, the reaction mixture was concentrated and purified by silica gel flash chromatography to afford 1.31 g of the product (86.7% yield).

Synthesis of 5A2: 5A1 (1.32 g, 3.22 mmol) was dissolved in 20 mL of ethyl acetate. The reaction flask was flushed with nitrogen and 70 mg of 5% Pd/C added. After stirring at RT for more than 48 h under a hydrogen atmosphere, the reaction mixture was filtered and the filtrate concentrated under vacuum to afford 1.074 g of the product (104% yield).

Synthesis of 5A3: Imidazole (32 mg, 0.468 mmol) and TBDMSCl (61 mg, 0.406 mmol) were added to a solution of 5A2 (0.1 g, 0.312 mmol) in 1.0 mL DMF. The reaction mixture was stirred at RT overnight and then diluted with ethyl acetate and washed with water. The organic layer was then dried over anhydrous $Na_2SO_4$, filtered, concentrated, and purified by silica gel flash chromatography to obtain 0.135 g of desired product (quantitative yield).

Synthesis of 5A4: Potassium carbonate (172 mg) was added to a solution of 5A3 (0.135 g, 0.312 mmol) in 5 mL of MeOH/water (1:1). The reaction mixture was left stirring at RT overnight and then diluted with ethyl acetate and washed with water. The organic layer was dried over anhydrous $Na_2SO_4$, filtered, concentrated, and purified by silica gel flash chromatography to obtain 52 mg of desired product (48% yield). MS confirms the structure (MALDI-MS obtained: M+Na=373).

Example 6: Synthesis of Other Amine Bifurcated SA Monomers (6A1-6A5)

The following shows an example of bifurcated SA monomers wherein X of the $Z^1$ is OH, OTBDMS, or N-(phthalimidyl), wherein $Z^2$ and $Z^3$ is either $R^{11}$ (TBDMS or H) or a SA monomer wherein X of the $Z^2$ and $Z^3$ is $N_3$ or $NH_2$.

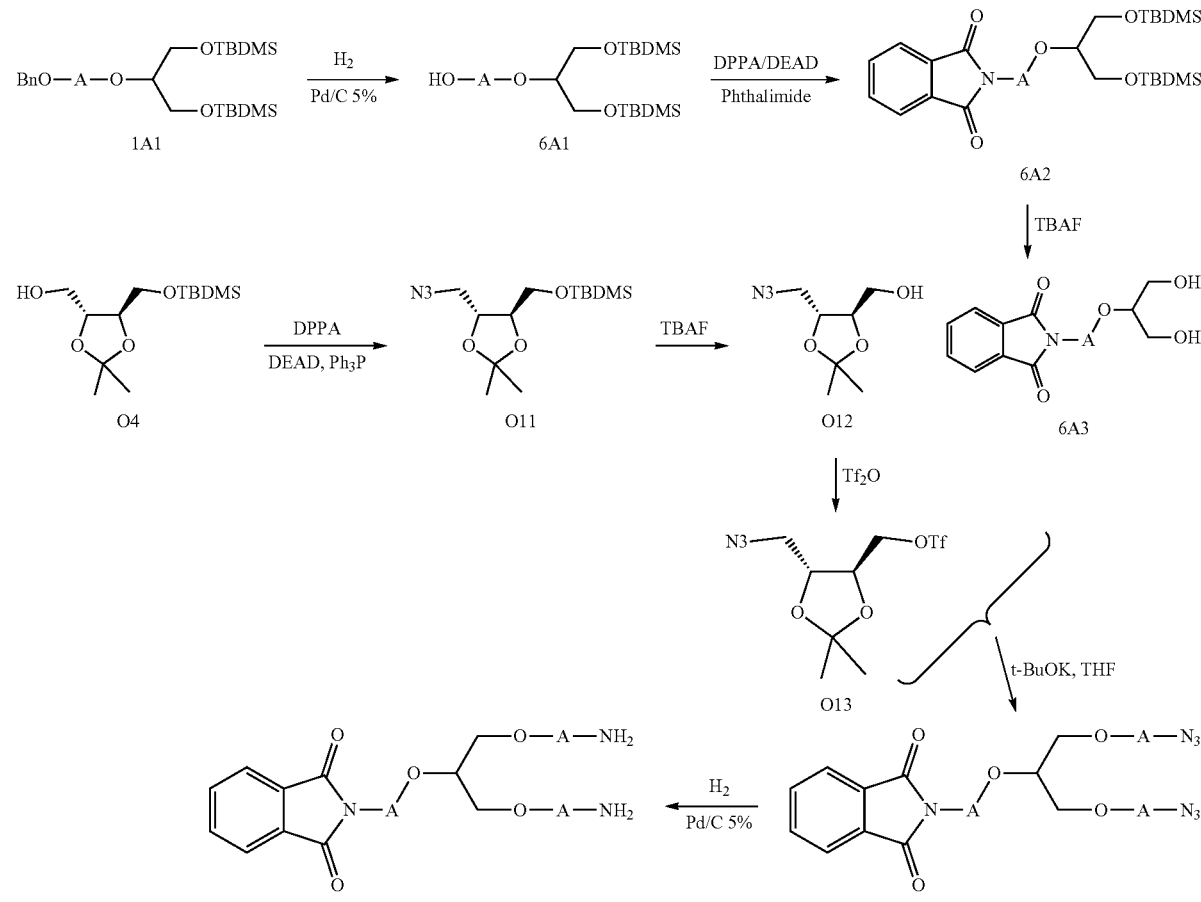

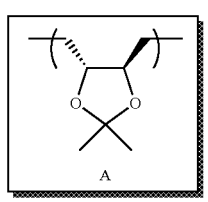

Synthesis of O11: The OH groups of O4 were converted directly to the azide groups using DPPA and DEAD following the same procedure as 2A3. Starting with 3 grams of O4, silica gel flash chromatographic purification afforded 4.63 g of the desired product (quantitative yield).

Synthesis of O12: The TBDMS protecting group of O11 was removed by TBAF following the same procedure as 1A2. Starting with 4.63 g of O11, silica gel flash chromatographic purification afforded 1.7 g of the desired product (59.2% yield). MS confirms the structure (ESI-MS obtained: M+Na=210).

Synthesis of O13: O13 was synthesized from O12 following the same procedure as O3 using triflic anhydride as the activating reagent. The reaction mixture was used directly for the next reaction (assuming quantitative yield).

Synthesis of 6A1: The benzyl protecting group of 1A1 (2.7 g) was removed by hydrogenation following the same procedure as 3A1. The reaction mixture was filtered. The filtrate was concentrated under vacuum to afford 2.36 g of the desired product (quantitative).

Synthesis of 6A2: 6A2 was prepared following the same procedure as 2A5. Starting from 0.1 g of 6A1, silica gel flash chromatographic purification afforded 0.06 g of the desired product (47% yield). MS confirms the structure (ESI-MS obtained: M+Na=616.2).

Synthesis of 6A3: The TBDMS protecting groups of 6A2 were removed by TBAF following the same procedure as 1A2. Starting from 60 mg of 6A2, silica gel flash chromatographic purification afforded 37 mg of the product (51% yield). MS confirms the structure (ESI-MS obtained: M+Na=388.07).

Synthesis of 6A4: 6A4 was prepared following the same procedure as 1A1 by condensing O13 (64 mg) with 6A3 (37 mg). 4 mg of final product was obtained after silica gel flash chromatographic purification (6% yield).

Synthesis of 6A5: Ethyl acetate (~2 mL) was added to a flask containing 6A4 (4 mg, 0.006 mmol). The reaction mixture was flushed under nitrogen and then 5 mg of palladium on carbon (5%) added. The mixture was stirred under a hydrogen atmosphere at RT overnight. The reaction mixture was filtered. The filtrate was dried under vacuum to afford the product in quantitative yield.

Example 7: Synthesis of Bifurcated SA Monomers with 4 or More Sugar Alcohols (7A1-7A5)

The following shows an example of bifurcated SA monomers wherein the p of $Z^1$, $Z^2$, $Z^3$ is not 1.

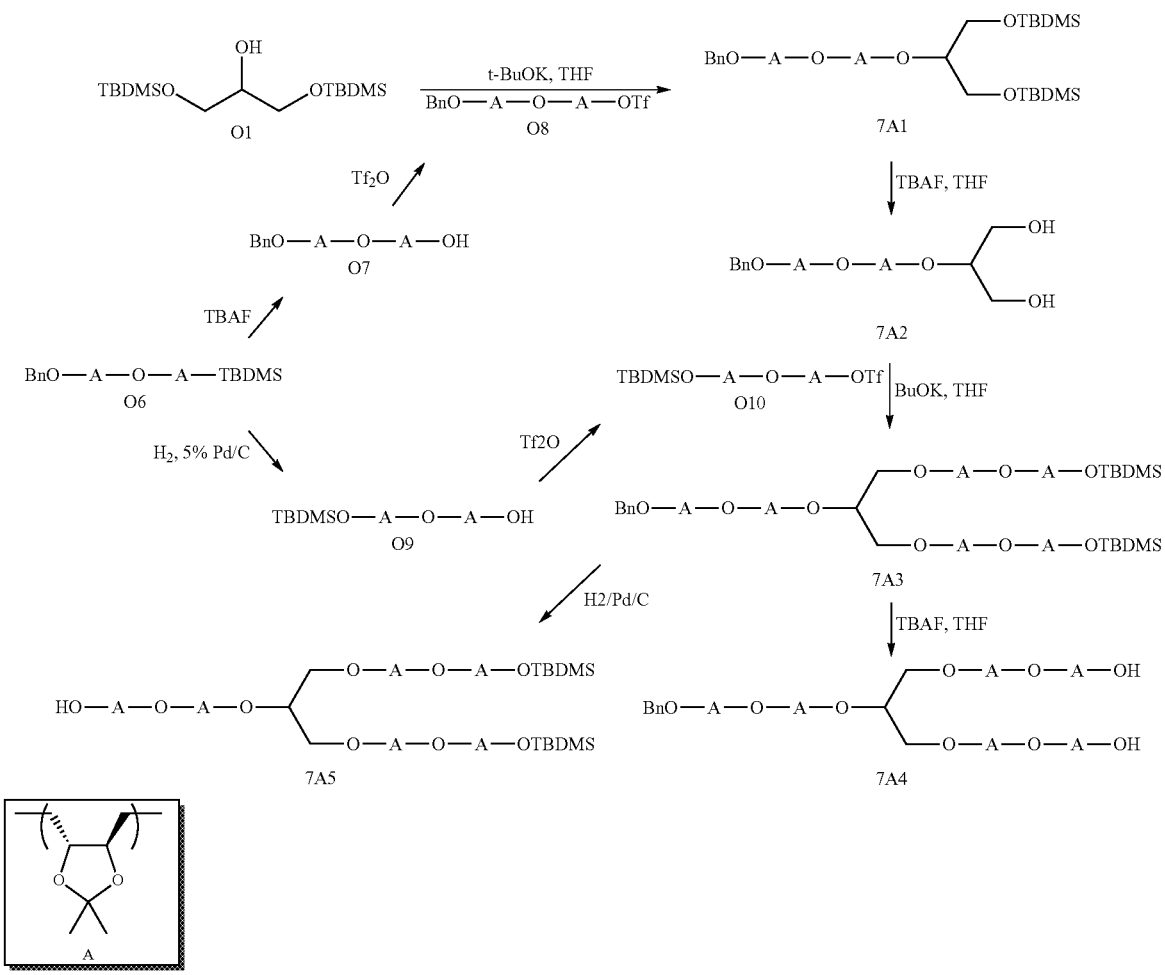

Scheme 7

Synthesis of O6: O6 was prepared following the same procedure as 1A1. Starting from 13.15 g of O4 and 12.76 g of O3, silica gel flash chromatographic purification afforded 5.3 g of the desired product (22% yield). MS confirms the structure.

Synthesis of O7: O7 was prepared following the same procedure as 1A2. Starting from 0.8 g of O6, silica gel flash chromatographic purification afforded 0.468 g of the desired product (75.5% yield). MS confirms the structure.

Synthesis of O8: O8 was prepared following the same procedure as O3 using triflic anhydride as an activating reagent. The product was used directly for the next reaction without any further purification (assume quantitative yield).

Synthesis of O9: O9 was prepared following the same procedure as 3A1. After the reaction, the reaction mixture was filtered. The filtrate was concentrated to afford the product in quantitative yield.

Synthesis of O10: O10 was prepared following the same procedure as O3 using triflic anhydride as an activating reagent. The product was used directly for the next reaction without any further purification (assume quantitative yield).

Synthesis of 7A1: 7A1 is prepared following the same procedure as 1A1 by condensing O1 with O8.

Synthesis of 7A2: 7A2 is prepared following the same procedure as 1A2 using TBAF as the deprotection reagent.

Synthesis of 7A3: 7A3 is prepared following the same procedure as 1A1 by condensing 7A2 with two O10 molecules.

Synthesis of 7A4: The TBDMS protecting groups of 7A3 are removed by TBAF following the same procedure as 1A2.

Synthesis of 7A5: The benzyl protecting group of 7A3 is removed by hydrogenation following the same procedure as 3A1.

Example 8: Synthesis of Bifurcated SA Monomers Using Mannitol (8A1-8A5)

The following shows an example of bifurcated SA monomers wherein each of $Z^1$, $Z^2$, and $Z^3$ is independently either $R^{11}$ or

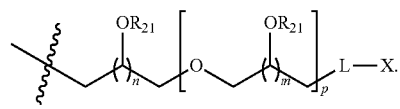

Scheme 8

-continued

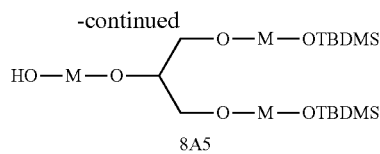

8A5

Synthesis of M1: M1 was synthesized previously (compound I2-b in our previous U.S. Pat. No. 9,907,079B$_2$).

Synthesis of M2: M2 is synthesized following a similar protocol as compound I3-b in our previous patent (U.S. Pat. No. 9,907,079B$_2$). Briefly, M1 (4.9 g, 8.7 mmol) is suspended in methanol (18 mL) by sonication for 5 minutes. A solution of 5% (w/v) iodine in methanol (17 mL) is added and the reaction left stirring at RT overnight. The reaction is quenched by the addition of 3% aqueous sodium thiosulfate in small portions until no brown color remains (~15 mL total). The suspension is concentrated in vacuo to remove most of the MeOH, diluted by the addition of 15 mL water, and then extracted three times with 30 mL of dichloromethane. The combined organic layers are washed with 20 mL of brine, dried over sodium sulfate, and purified by silica gel column chromatography to obtain the desired product (expected yield: 30-60%). MS is used to confirm the structure.

Synthesis of M3: M3 is synthesized following a similar protocol as synthesizing O2 (U.S. Pat. No. 9,907,079B$_2$). M2 (2.161 g, 61.69 mmol) is added to a flask containing NaH (60% dispersion in oil, 2.72 g, 68.0 mmol) and 250 mL of DMF at −80° C. 7.70 mL (64.77 mmol) benzyl bromide is then added drop-wise. The flask is warmed to RT and stirred overnight. The reaction mixture is diluted with DCM, cooled to 0° C., and then quenched drop-wise with water. The aqueous phase is separated and extracted with DCM. The organic fractions are combined and washed 3 times with brine. The organic phase is then dried over anhydrous Na$_2$SO$_4$, filtered, concentrated, and purified by silica gel flash chromatography to afford the desired product (expected yield: 60-80%). MS is used to confirm the structure.

Synthesis of M4: M4 is synthesized following a similar protocol as synthesizing O4 (U.S. Pat. No. 9,907,079B$_2$). M2 (2.17 g, 61.8 mmol) is added to a flask containing NaH (60% dispersion, 2.72 g, 67.98 mmol) in 102.76 mL of THF below-10° C. After 30 minutes, TBDMSCl (9.76 g, 64.73 mmol) is added. The reaction is warmed to RT and left stirring overnight. The reaction is concentrated and dissolved in DCM. After washing 3 times with brine, the organic layers are dried over anhydrous Na$_2$SO$_4$, filtered, concentrated, and then purified by silica gel flash chromatography to afford the desired product (expected yield: 60-80%). MS confirms the structure.

Synthesis of M5: M5 is prepared following the same procedure as O3 using triflic anhydride as an activating reagent. The product is used directly for the next reaction without any further purification (assume quantitative yield).

Synthesis of M6: M6 is prepared following the same procedure as O3 using triflic anhydride as an activating reagent. The product is used directly for the next reaction without any further purification (assume quantitative yield).

Synthesis of 8A1: 8A1 is prepared following the same procedure as 1A1 by condensing O1 with M5.

Synthesis of 8A2: 8A2 is prepared following the same procedure as 1A2 using TBAF as the deprotection reagent.

Synthesis of 8A3: 8A3 is prepared following the same procedure as 1A1 by condensing 8A2 with two M6 molecules.

Synthesis of 8A4: The TBDMS protecting groups of 8A3 are removed by TBAF following the same procedure as 1A2.

Synthesis of 8A5: The benzyl protecting group of 8A3 is removed by hydrogenation following the same procedure as 3A1.

B. Examples of Solid Phase-Linked Bifurcated SA Monomers and Fully Deprotected Bifurcated SA Monomers Example 9: Attaching an Amine Bifurcated SA Monomer to Solid Phase The following shows examples of solid phase-linked bifurcated SA monomers wherein W is-NH— and X of the Z$^2$ and Z$^3$ is selected from —OTBDMS, —OH, —N-(phthlimidyl), or —NH$_2$. The following also shows examples of bifurcated SA monomers cleaved from the solid phase.

Scheme 9

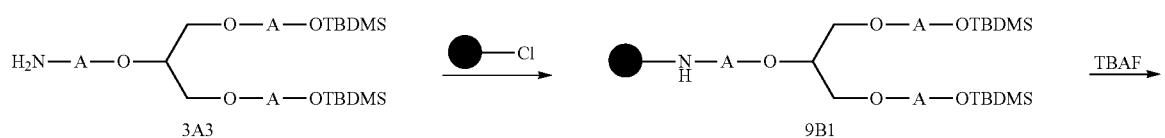

-continued

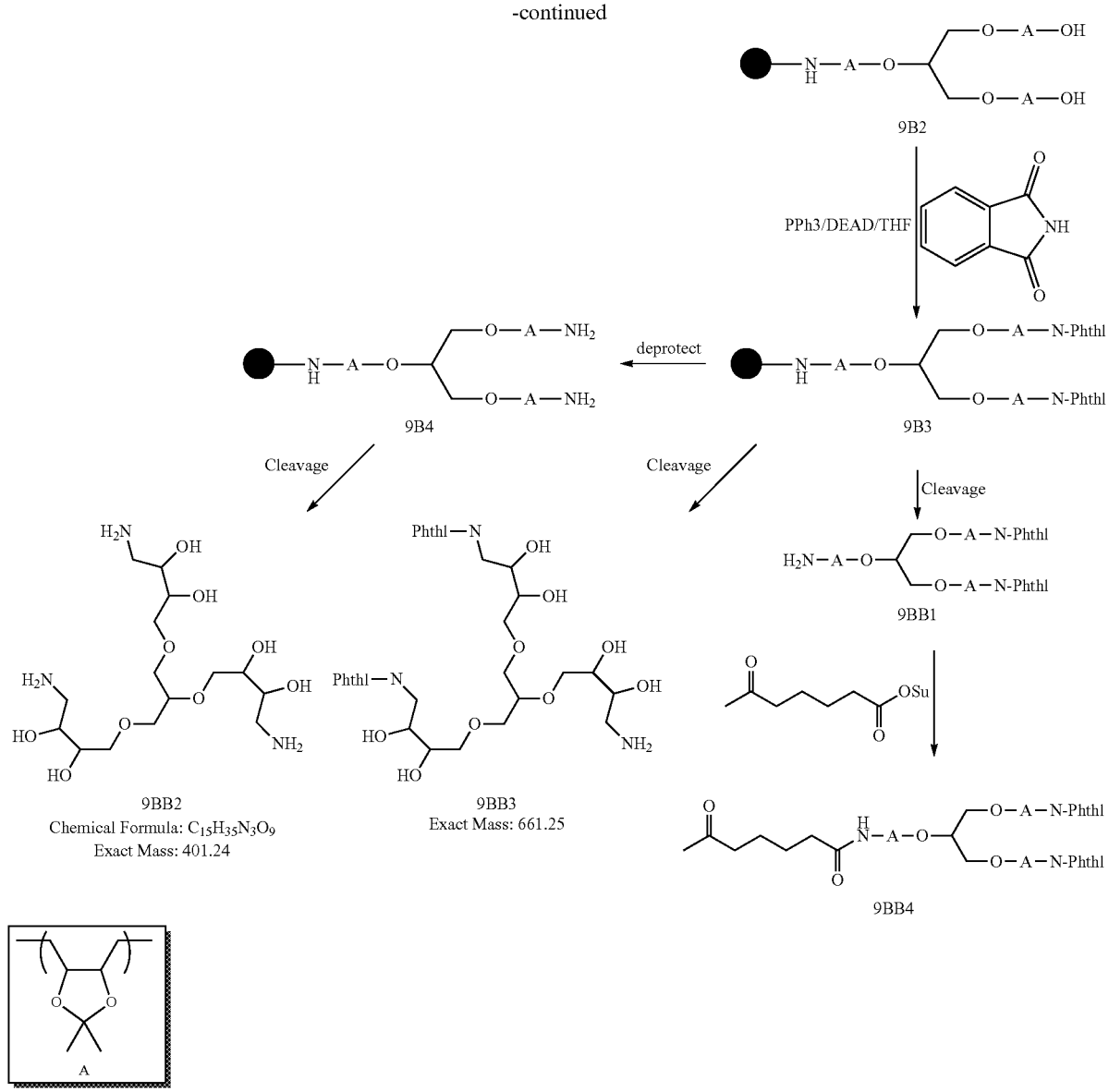

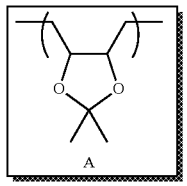

Synthesis of 9B1: DCM (5 mL) and DIPEA (74 µL) were added to a 15 mL centrifuge tube containing 3A3 (0.1043 g, 0.133 mmol). After mixing for a few minutes, the solution was added to a flask containing 0.689 g of 2-chlorotrityl chloride resin. The mixture was stirred at RT for 2 h and the solvent filtered. The resin was washed 3 times with 10 mL of DCM/MeOH/DIPEA (17:2:1), 3 times with 10 mL of DCM, and 2 times with 10 mL of DCM to obtain the desired product. The product was used directly in the next reaction (assuming quantitative yield).

Synthesis of 9B2: 1M TBAF solution in THF (2.66 mL) was added to a solid phase peptide synthesis flask with frit containing 9B1 (0.7 g, 0.133 mmol). The solution and resin were mixed by bubbling $N_2$ for 2 h. The solvent was removed and the resin washed 6 times with 10 mL DCM to obtain the desired product. The product was used directly in the next reaction (assuming quantitative yield).

Synthesis of 9B3: Triphenylphosphine (1.047 g, 3.99 mmol) and phthalimide (0.587 g, 3.99 mmol) were added to a flask containing 9B2 (containing 0.133 mmol of the SA molecule). After flushing the flask with $N_2$, 17.5 mL of THF was added and the solution cooled below 4° C. DEAD (0.96 g, 5.32 mmol) was added. The reaction was warmed to RT and left on a shaker overnight. The resin was washed 6 times with 10 mL DCM and dried under vacuum to afford the desired product (0.8438 g, 106% yield).

Synthesis of 9BB1 (partially deprotected): A small amount of resin was cleaved with 1% TFA in DCM and neutralized immediately with 1% TEA in DCM. LC-MS analysis of the cleaved material confirms the structure (ESI-MS obtained: M+H=783.2).

Synthesis of 9BB3 (fully deprotected): A small amount of resin was cleaved with 1% TFA in DCM. LC-MS analysis of the cleaved material confirms the structure (ESI-MS obtained: M+H=662.35).

Synthesis of 9B4:10 mL of 1M hydrazine in DMF/THF (3:1) was added to a solid phase peptide synthesis flask with frit containing 9B3 (0.41 g containing 0.065 mmol of SA monomer). The solution and resin were mixed by bubbling $N_2$ overnight. The resin was washed 6 times with 10 mL DCM and dried under vacuum to afford the desired product (0.4147 g).

Synthesis of 9BB2 (fully deprotected): A small amount of resin was cleaved with 1% TFA in DCM. LC-MS analysis of the cleaved material confirms the structure (ESI-MS: M+H=402.5).

Synthesis of 9BB4:5-Acetylvaleric NHS ester (7.23 mg, 0.03 mmol) and 15.6 µL of DIPEA is added to a 1.5 mL centrifuge tube containing a solution of 9BB1 (15.7 mg, 0.02 mmol) in 0.2 mL of DMF. After mixing for 2 h, water is added to directly precipitate the product. The product is washed 3 times with water to remove hydrolyzed 5-acetylvaleric acid.

Example 10. Attaching an Aminooxy Bifurcated Monomer to Solid Phase

The following shows examples of solid phase-linked bifurcated SA monomers wherein W is —ONH— and X of the $Z^2$ and $Z^3$ is selected from —OTBDMS, —OH, —N-(phthlimidyl), or —$NH_2$. The following also shows examples of bifurcated SA monomers cleaved from the solid phase.

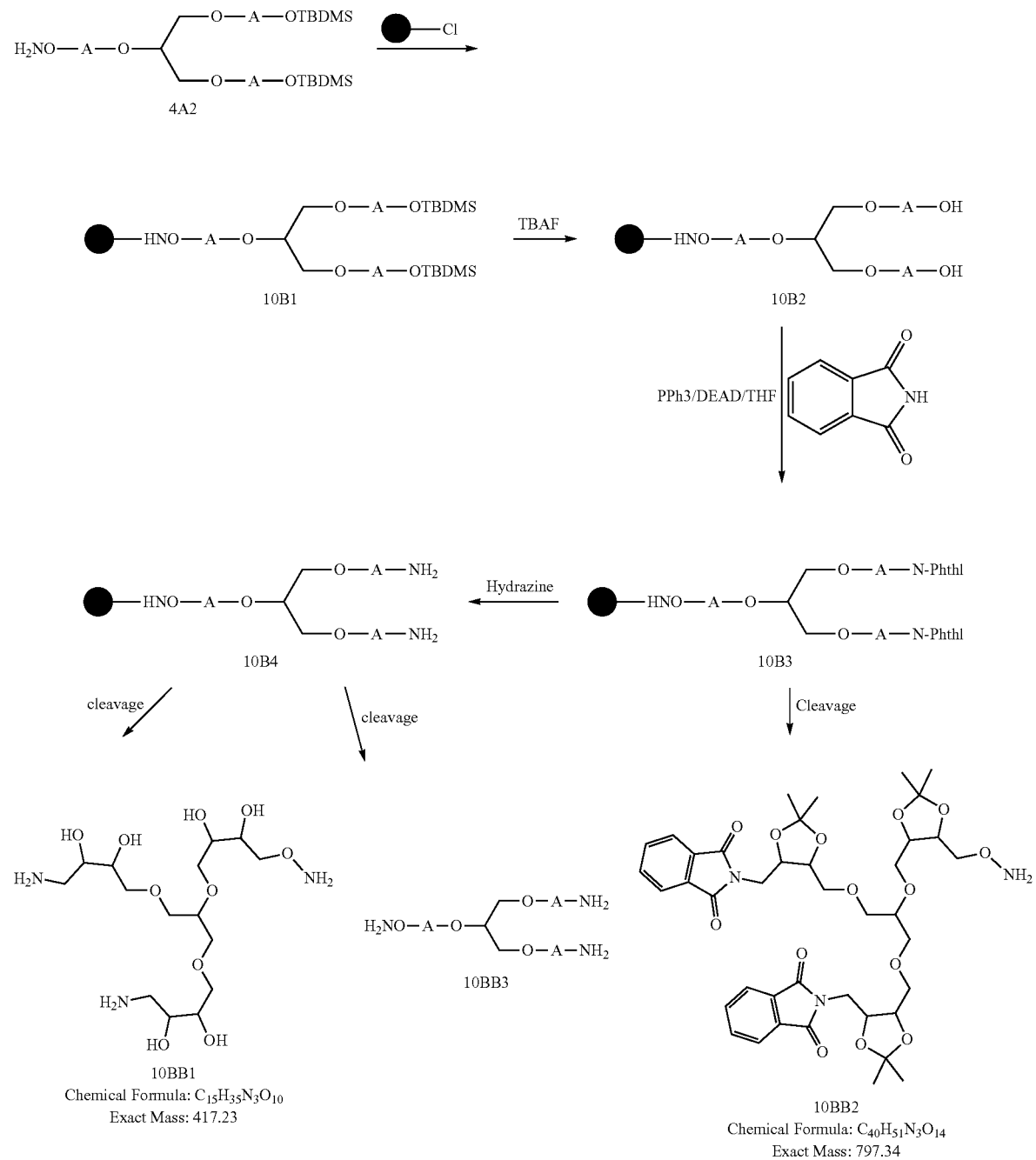

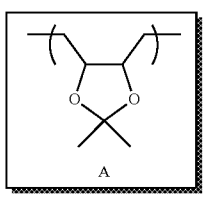

Synthesis of 10B1: 10B1 was synthesized following the same procedure as 9B1 using 0.539 g of 2-chlorotrityl chloride resin and 83 mg of 4A2. The product was used directly in the next reaction (assuming quantitative yield).

Synthesis of 10B2: The TBDMS protecting groups of 10B2 were removed by TBAF following the same procedure as 9B2. The product was used directly in the next reaction (assuming quantitative yield).

Synthesis of 10B3: 10B3 was synthesized following the same procedure as 9B3 using triphenylphosphine, phthalimide, and DEAD. The resin was dried under vacuum to afford 0.69 g of desired product (110% yield).

Synthesis of 10BB2 (partially deprotected): A small amount of resin was cleaved with 1% TFA (20 μL per mg of resin) and neutralized immediately with the same volume of 1% TEA in DCM (20 μL per mg of resin). LC-MS analysis of the cleaved material confirms the structure (ESI-MS: M-18 (H2O)=780.95).

Synthesis of 10BB3 (partially deprotected): 10BB3 is synthesized using the same protocol as 10BB2. Solvent was removed under vacuum to afford the product.

Synthesis of 10B4: The phthlimidyl protecting groups of 10B3 were removed by hydrazine following the same procedure as 9B4.

Synthesis of 10BB1: A small amount of resin was cleaved with 1% TFA in DCM to afford the desired product.

Example 11. Attaching a Hydroxy Bifurcated Monomer to Solid Phase

The following shows an example of a solid phase-linked bifurcated SA monomer wherein W is —O—.

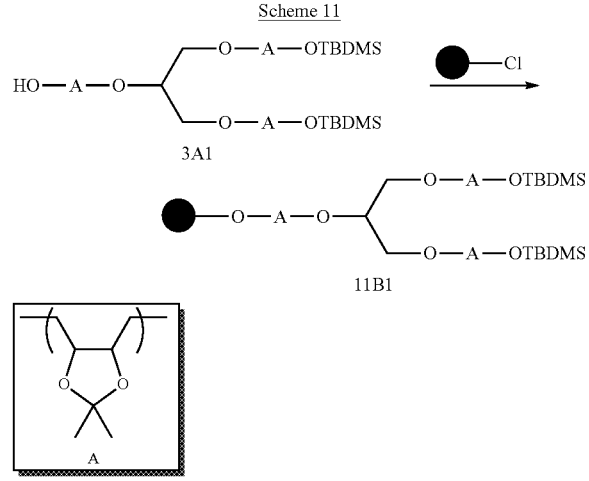

Scheme 11

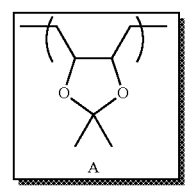

Synthesis f 11B1: 11B1 is synthesized following the same procedure as 9B1 using 0.54 g of 2-chlorotrityl chloride resin and 90 mg of 3A1. The product is used directly in the next reaction (assuming quantitative yield).

Example 12: Synthesizing Heterobifunctional Bifurcated SA Monomers with Keto Groups The following shows examples of SA bifurcated SA monomer wherein X of the $Z^1$ is selected from a group consisting or —NH—C(=O)—$CH_2$-J, maleimide (N-maleimidopropyl), —NH—C(=O)—$CH_2$—S—C(=O)—$CH_3$, —NH—C(=O)—$(CH_2)_2$—S—S-pyridyl, and —NH—C(=$NH_2^+$)—$CH_2CH_2CH_2$—SH; and X of the $Z^2$ and $Z^3$ is —NH—C(=O)—$R^9$—C(=O)—$CH_3$ wherein $R^9$ is $(CH_2)_4$— or —$(CH_2)_2$—.

Scheme 12

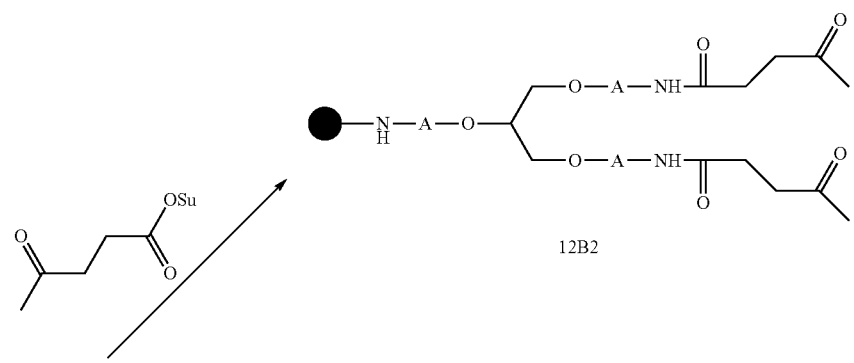

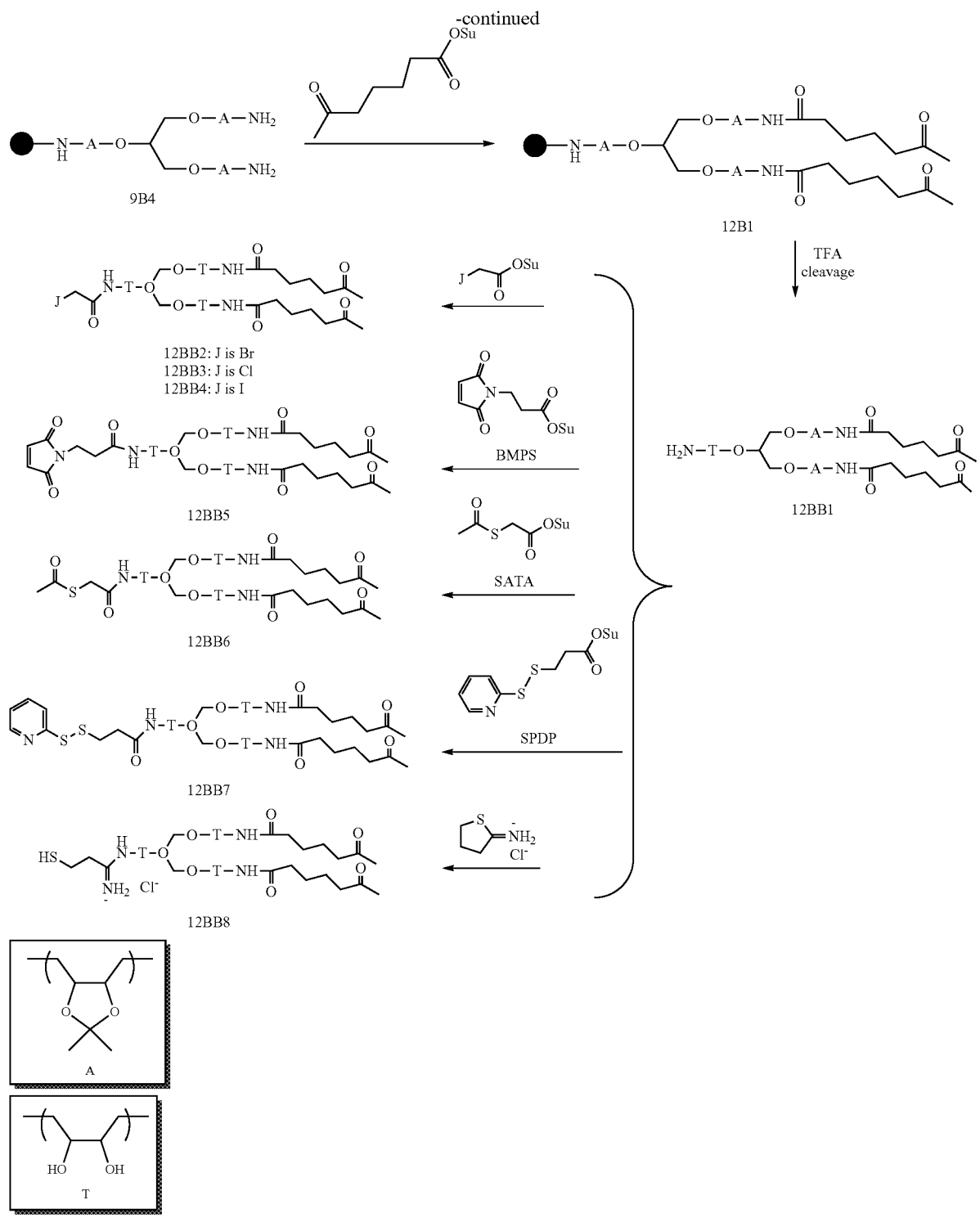

Synthesis of 12B1: 5-Acetylvaleric NHS ester (54 mg, 0.22 mmol) was added to a tube containing 1.12 mL of 0.4M DIPEA solution in DMF. After mixing for a few minutes, the mixture was added to a tube containing 101.1 mg of 9B4. The solution and resin were mixed at RT overnight. The resin was washed with DMF and DCM to afford the desired product. A small amount of resin was taken out for the ninhydrin test and showed a negative result. A small amount of resin was cleaved with 1% TFA in DCM. MS confirms the structure. ESI-MS: M+H=655.1 (fully deprotected), M+H=775.7 (acetonide protected).

Synthesis of 12B2: Levulinic acid NHS ester (69.5 mg, 0.33 mmol) was added to a tube containing 1.625 mL of 0.4M DIPEA solution in DMF. After mixing for a few minutes, the mixture was added to a tube containing 98.7 mg of 9B4. The solution and resin were mixed at RT overnight. The resin was washed with DMF and DCM to afford the desired product. A small amount of resin was taken out for the ninhydrin test and showed a negative result. A small amount of resin was cleaved with 1% TFA in DCM. MS confirms the structure. ESI-MS: M+H=598.9 (fully deprotected), M+H=719.5 (acetonide protected).

Synthesis of 12BB2, 12BB3, 12BB4, 12BB5, 12BB6, and 12BB7: 12BB2-7 are synthesized following the standard solution phase NHS ester coupling method. Briefly, amine starting material 12BB1 (1 equiv.), NHS ester (1.5 equiv.), and DIPEA (3 equiv.) were dissolved in DMF. The final concentration of amine (12BB1) in DMF is 0.2M. The reaction mixture is stirred at RT for a few hours to overnight. HPLC is used to monitor the completion of the reaction. The final product is purified by HPLC and the structure confirmed by MS. Starting materials for the NHS esters are as follows: bromoacetic acid NHS ester for 12BB2, chloroacetic acid NHS ester for 12BB3, iodoacetic acid NHS ester for 12BB4, N-maleimidopropyl-oxysuccinimide ester (BMPS) for 12BB5, N-succinimidyl S-acetylthioacetate (SATA) for 12BB6, succinimidyl 3-(2-pyridyldithio) propionate (SPDP) for 12BB7, and 2-imminothiolane for 12BB8.

Synthesis of 12BB8: 12BB8 is synthesized following the standard solution phase NHS ester coupling method as 12BB2-7. 2-Imminothiolane is used as the starting material instead of a standard NHS ester.

Example 13: Synthesis of Heterobifunctional Bifurcated SA Monomers with Amine Functional Groups The following shows examples of bifurcated SA monomer wherein X of the $Z^1$ is —$NH_2$ and X of the $Z^2$ and $Z^3$ is selected from a group consisting of —NH—C(=O)—$R^9$—C(=O)OH wherein $R^9$ is —$(CH_2)_2$—, —NH—C(=O)—$CH_2$-J, and maleimide (N-maleimidopropyl).

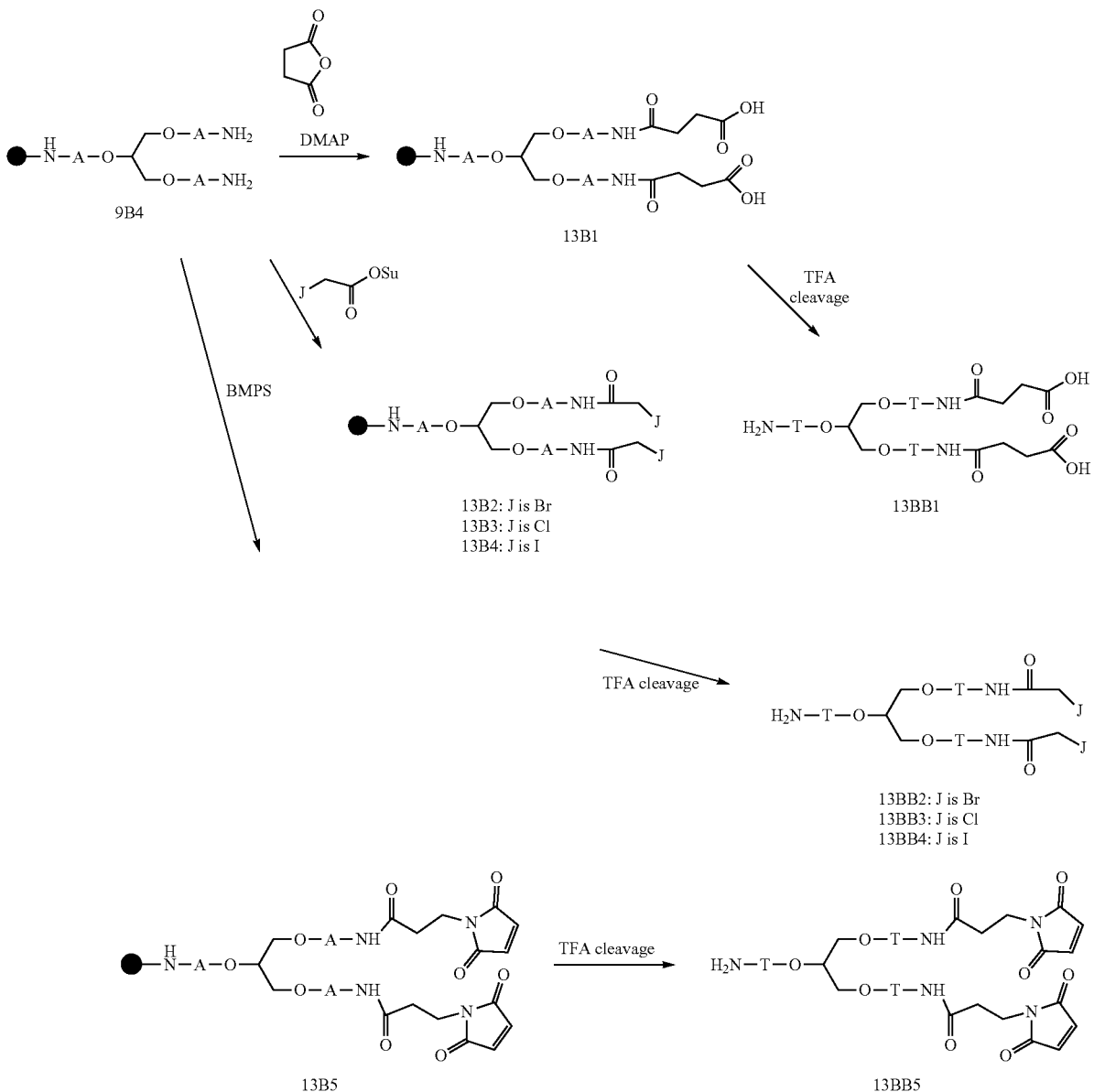

Scheme 13

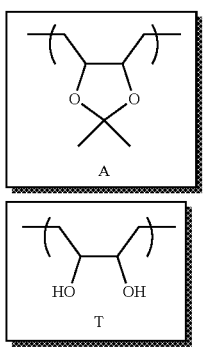

Synthesis of 13B1: 13B1 is synthesized following the same protocol used for linear SA molecule on solid phase. 1 mL of 0.4M succinic anhydride solution in NMP, 1 mL of 0.6M triethyl amine solution in NMP, and 1 mL of 0.2M DMAP solution in NMP is added to a tube containing 108.3 mg of 9B4. The solution and resin were mixed at 45° C. for 3 h first, then at RT overnight. The resin is washed with DMF and DCM to afford the desired product. A small amount of resin can be taken out for the ninhydrin test.

Synthesis of 13BB1: 13BB1 is obtained by cleavage of the resin in 1% TFA (50 µL per mg of resin) in DCM for a few hours or overnight. HPLC and MS are used to monitor the completion of the deprotection reaction. Once complete, the solution is removed under vacuum to afford the desired product.

Synthesis of 13B2, 13B3, 13B4, and 13B5: 13B2-5 are synthesized following the standard NHS coupling protocol on solid support for 12B1. Briefly, 0.22 mmol of NHS ester (bromoacetyl NHS ester is added to a tube containing 1.12 mL of 0.4M DIPEA solution in DMF. After mixing for a few minutes, the mixture is added to a tube containing 0.1 g of 9B4. The solution and resin are mixed at RT overnight. The resin is washed with DMF and DCM to afford the desired product. A small amount of resin can be taken out for the ninhydrin test.

Synthesis of 13BB2, 13BB3, 13BB4, and 13BB5: 13BB2-5 are released from the resin following the same protocol as 13BB1. Solvent is removed under vacuum to afford the desired product.

Example 14: Synthesis of Heterobifunctional Bifurcated SA Monomers Carrying Thiol and Amine Functional Groups The following shows examples of bifurcated SA monomer wherein X of the $Z^1$ is —$NH_2$ and X of the $Z^2$ and $Z^3$ is selected from a group consisting of —NH—C(=$NH_2^+$)—($CH_2$)$_3$—SH, —NH—C(=O)—$CH_2$—S—C(=O)—$CH_3$, —NH—C(=O)—$R^9$—SH, —NH—C(=O)—($CH_2$)$_2$—S—S-pyridyl, —NH—C(=O)—$CH_2CH_2$—SH.

Scheme 14

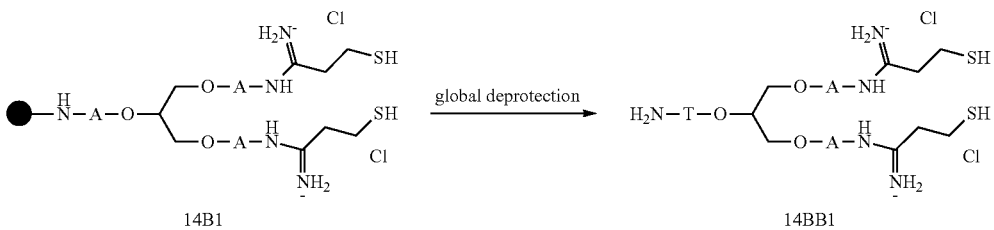

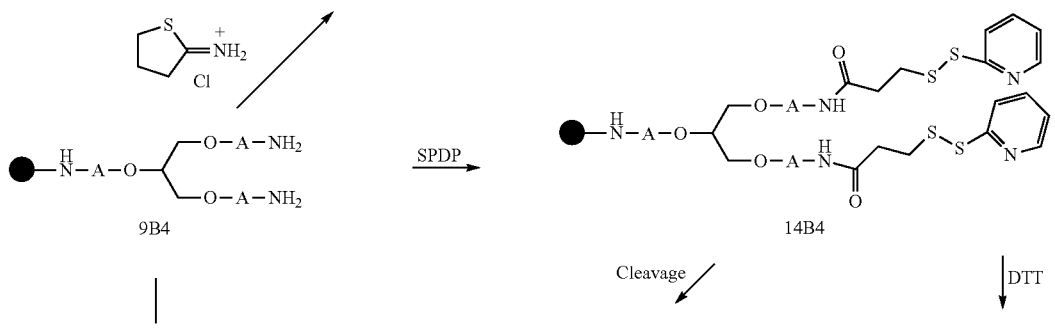

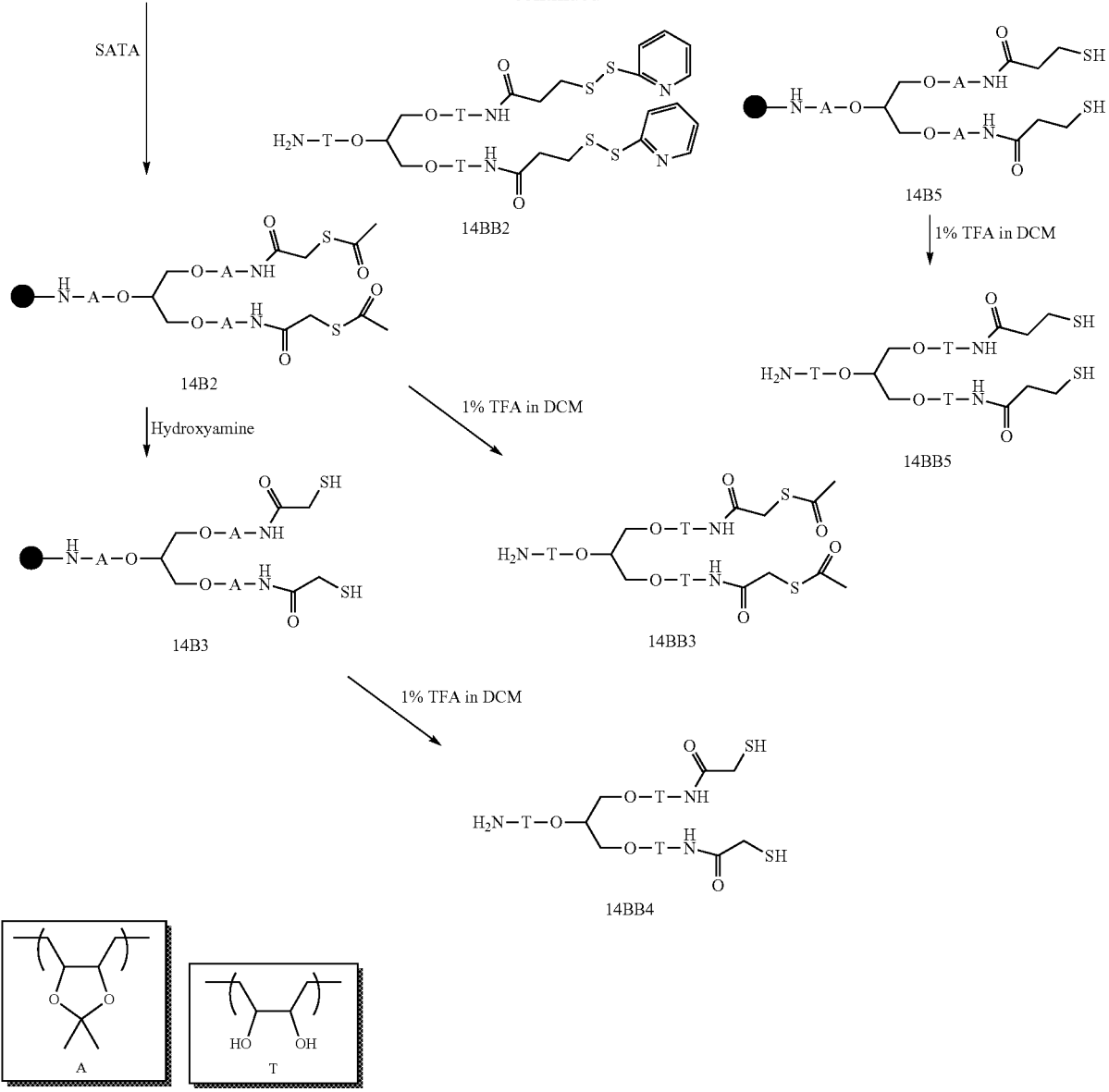

Synthesis of 14B1: 14B1 is synthesized following the standard NHS coupling protocol on solid support for 12B1. 2-Imminothiolane is used as the starting material instead of a standard NHS ester. The resin is washed with DMF and DCM to afford the desired product. A small amount of resin can be taken out for the ninhydrin test.

Synthesis of 14B2 and 14B4: 14B2 and 14B5 are synthesized following the standard NHS coupling protocol on solid support for 12B1. The resin is washed with DMF and DCM to afford the desired product. A small amount of resin can be taken out for the ninhydrin test.

Synthesis of 14B3: 1 mL of 0.5M hydroxylamine solution in DMF is added to a tube containing 0.1 g 12B2 (~0.016 mmol). The solution and resin are mixed at RT for 15 minutes. The resin is washed with DMF and DCM to afford the desired product. The thiol content can be assayed using Ellman's reagent (5,5'-dithiobis-(2-nitrobenzoic acid); DTNB).

Synthesis of 14B5: 1 mL of 0.5M DTT solution in DMF is added to a tube containing 0.1 g 12B4 (~0.016 mmol). The solution and resin were mixed at RT for 15 minutes. The resin is washed with DMF and DCM to afford the desired product. The thiol content can be assayed using Ellman's reagent (DTNB).

Synthesis of 14BB1, 14BB2, 14BB3, 14BB4, and 14BB5: 14BB1-5 are released from the resin following the same protocol as 13BB1. Solvent is removed under vacuum to afford the desired product.

Example 15: Synthesis of Heterobifunctional Bifurcated SA Monomers Carrying One Side Acid and Another Side Keto Group The following shows examples of bifurcated SA monomer wherein X of the $Z^1$ is —NH—C(=O)—$R^9$—C(=O)OH, wherein $R^9$ is —$(CH_2)_2$— and X of the $Z^2$ and $Z^3$ is selected from a group consisting of —NH—C(=O)—$CH_2$-J and maleimide (N-maleimidopropyl).

Scheme 15

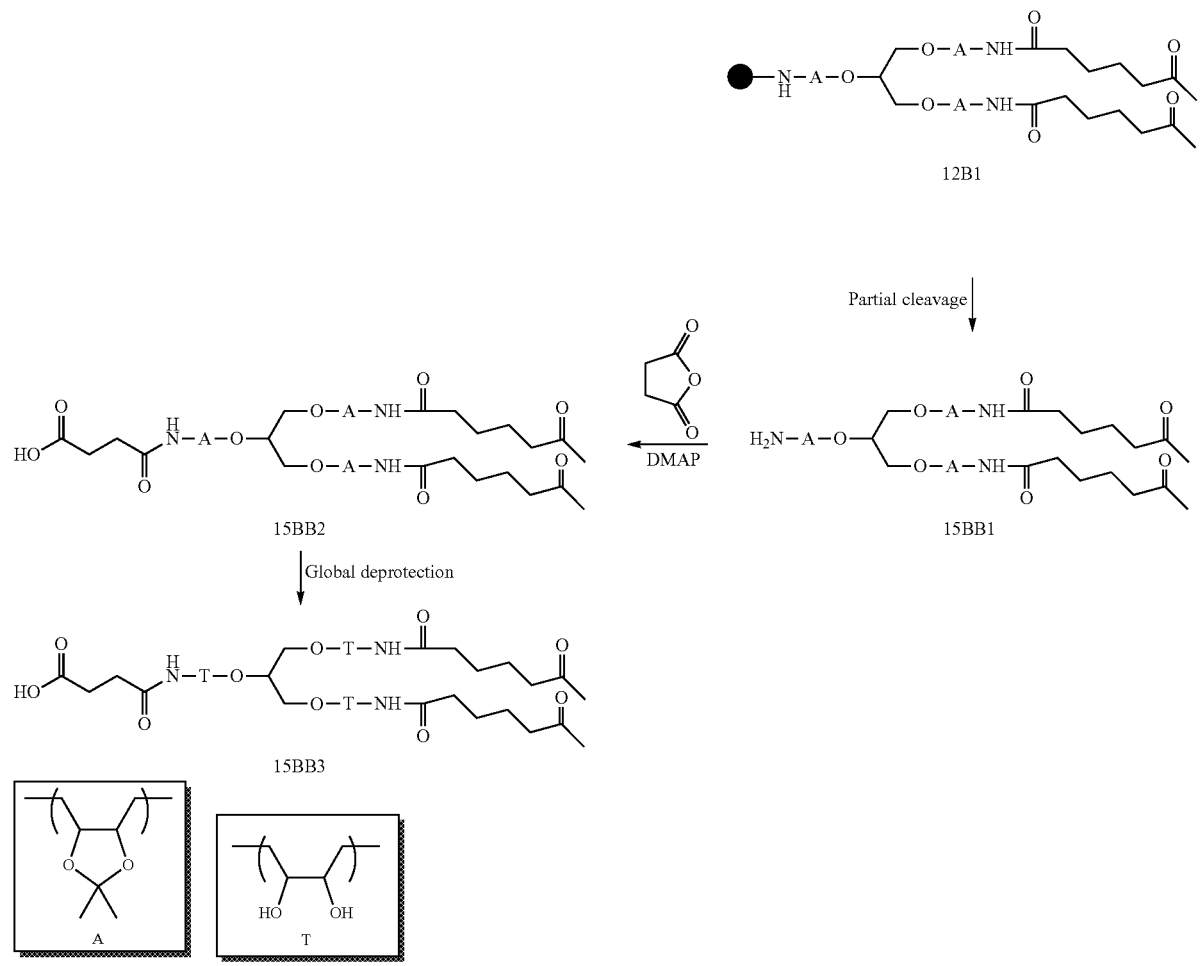

Synthesis of 15BB1: 15BB1 is released from the resin by following the same protocol as 10BB2. Briefly, approximately 2 mL of 1% TFA in DCM is added to 100 mg of resin. After 10 minutes, the resin is filtered and the filtrate neutralized immediately with 2 mL of 1% TEA in DCM. The solvent is removed under vacuum to afford the desired product.

Synthesis of 15BB2: 15BB2 is synthesized following a similar protocol as 13B1. Briefly, succinic anhydride (4 equiv.) and DMAP (0.5 equiv.) are added to a tube containing 10 mg of 15BB1 in DMF (final concentration of 15BB1 is 0.1M). The reaction mixture is stirred at 45° C. for 3 h and then at RT overnight. HPLC is used to monitor the reaction. Once the reaction is completed, the reaction mixture is purified by HPLC.

Synthesis of 15BB3:5 mg of 15BB2 is dissolved in 1-5 mL of 0.1% TFA in DCM and left at RT until all of the acetonide groups fall off in HPLC analysis. The solvent is removed under vacuum to afford the desired product.

Example 16: Synthesizing Heterobifunctional Bifurcated SA Monomers with an Aminooxy Group The following shows examples of bifurcated SA monomer wherein X of the $Z^1$ is —$ONH_2$ and X of the $Z^2$ and $Z^3$ is selected from a group consisting of —NH—C(=O)—$(CH_2)_2$C(=O)OH, —NH—C(=O)—$(CH_2)_4$—C(=O)—$CH_3$, —NH—C(=O)—$CH_2$-J, and maleimide (N-maleimidopropyl).

Scheme 16

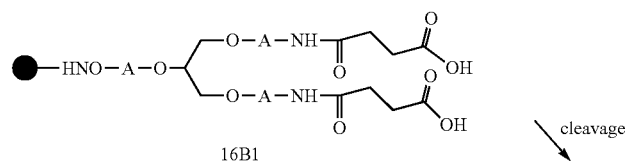

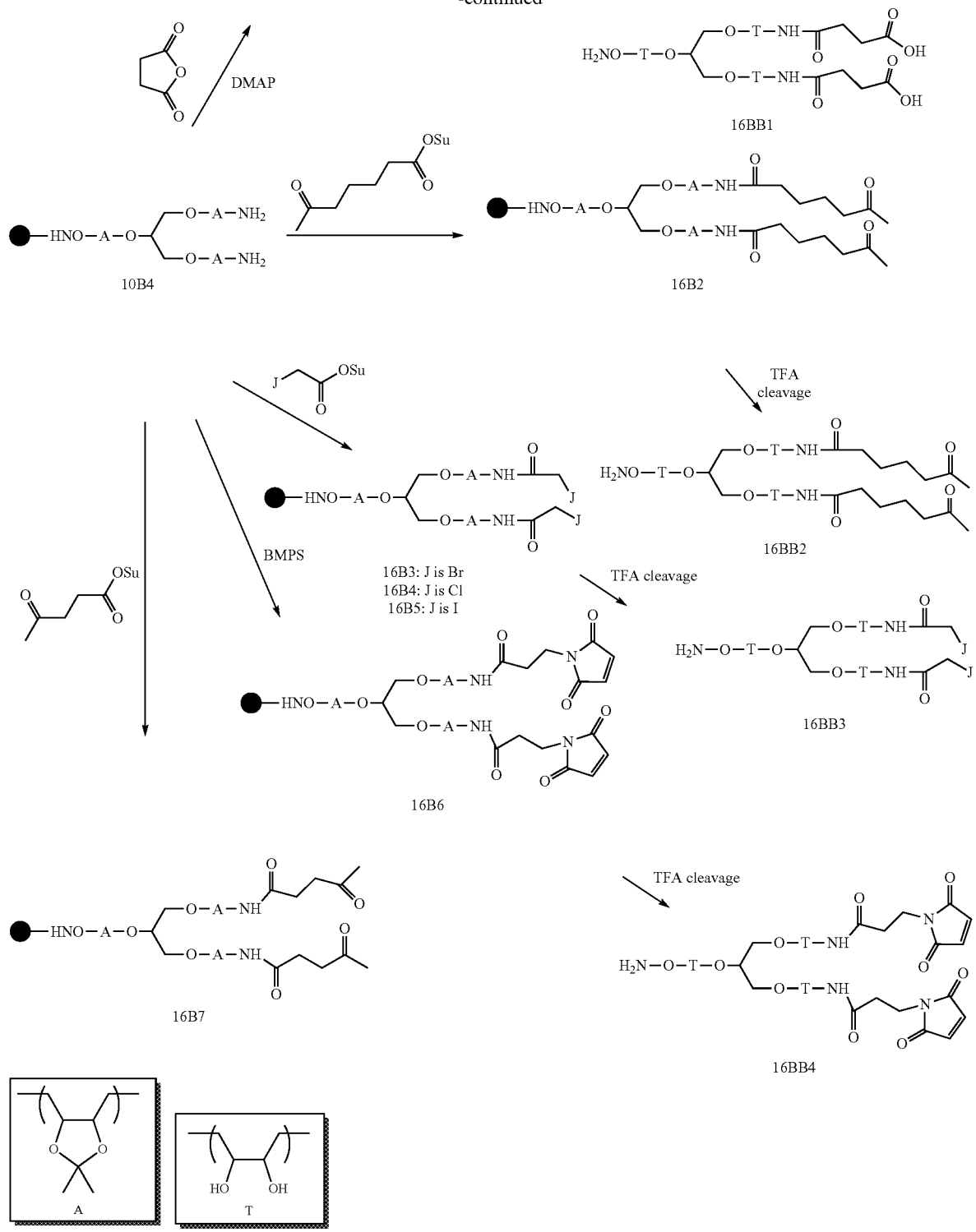

Synthesis of 16B1: 16B1 is synthesized following the same protocol as 13B1. The resin is washed with DMF and DCM to afford the desired product. A small amount of resin can be taken out for the ninhydrin test.

Synthesis of 16B2, 16B3, 16B4, 16B5, 16B6, and 16B7: 16B2-7 are synthesized following the standard NHS ester coupling protocol on solid support for 12B1. The resin is washed with DMF and DCM to afford the desired product. A small amount of resin can be taken out for the ninhydrin test.

Synthesis of 16BB1, 16BB2, 16BB3, and 16BB4: 16BB1-4 are released from the resin following the same protocol as 13BB1. Solvent is removed under vacuum to afford the desired product.

Example 17: Synthesis of Bifurcated SA Monomers Carrying Thiol and Aminooxy Functional Groups
The following shows examples of bifurcated SA monomer wherein X of the $Z^1$ is —$ONH_2$ and X of the $Z^2$ and $Z^3$ is selected from a group consisting of —NH—C(=O)—$CH_2$—S—C(=O)—$CH_3$, —NH—C(=O)—$R^9$—SH, —NH—C(=O)—$(CH_2)_2$—S—S-pyridyl, and —NH—C(=O)—$CH_2CH_2$—SH.
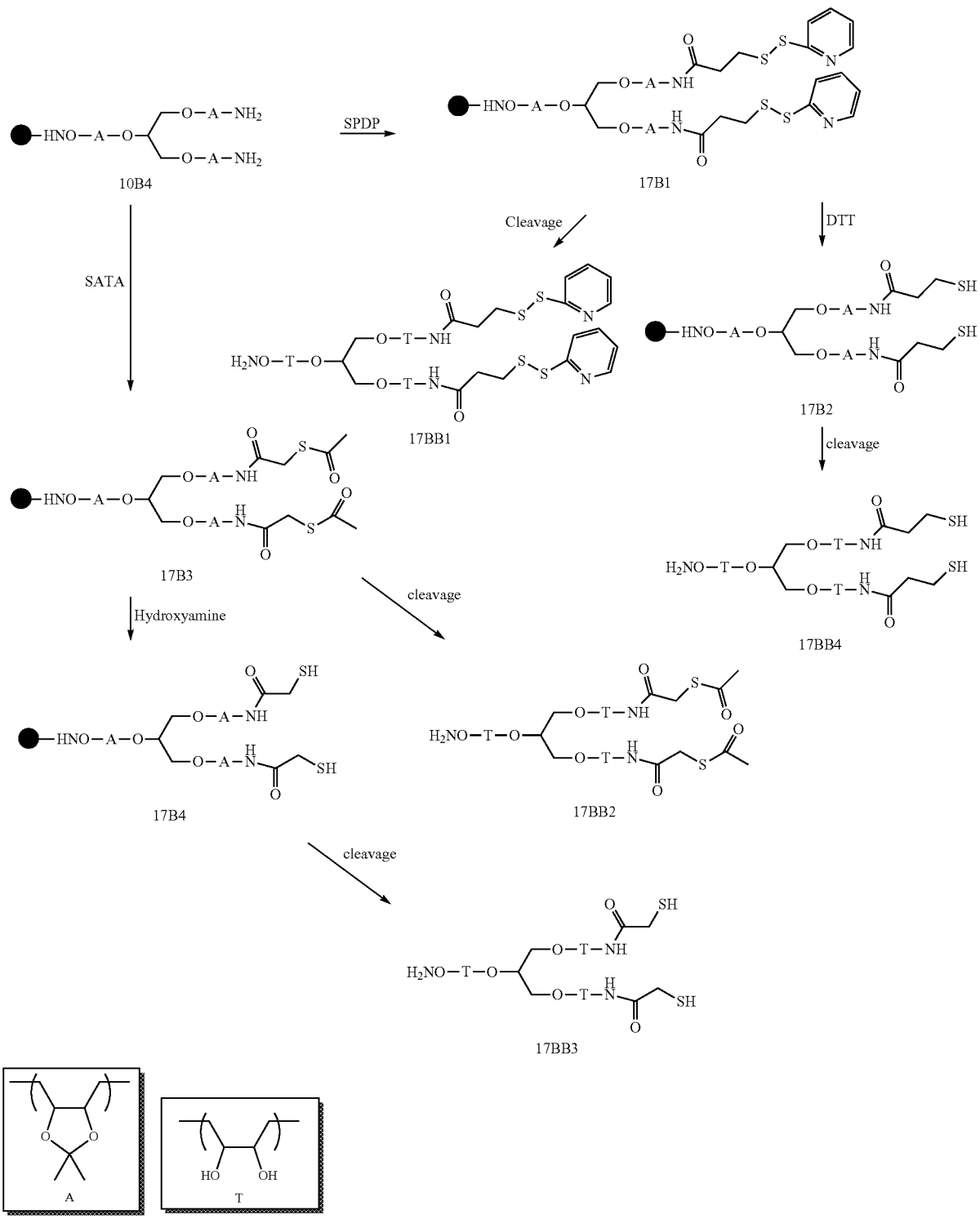
Scheme 17

Synthesis of 17B1 and 17B3: 17B1 and 17B3 are synthesized following the standard NHS coupling protocol on solid support for 12B1. The resin is washed with DMF and DCM to afford the desired product. A small amount of resin can be taken out for the ninhydrin test.

Synthesis of 17B2: 17B2 is synthesized following the same protocol as 14B5. The resin is washed with DMF and DCM to afford the desired product. The thiol content can be assayed using Ellman's reagent (DTNB).

Synthesis of 17B4: 17B4 is synthesized following the same protocol as 14B3. The resin is washed with DMF and DCM to afford the desired product. The thiol content can be assayed using Ellman's reagent (DTNB).

Synthesis of 17BB1, 17BB2, 17BB3, and 17BB4: 17BB1-4 are released from the resin following the same protocol as 13BB1. Solvent is removed under vacuum to afford the desired product.

Example 18: Synthesis of Heterobifunctional Bifurcated SA Monomers Carrying Thiol and Aminooxy Functional Groups The following shows examples of bifurcated SA monomer wherein X of the $Z^1$ is —$ONH_2$ and X of the $Z^2$ and $Z^3$ is either —S—S-pyridyl or —SH.

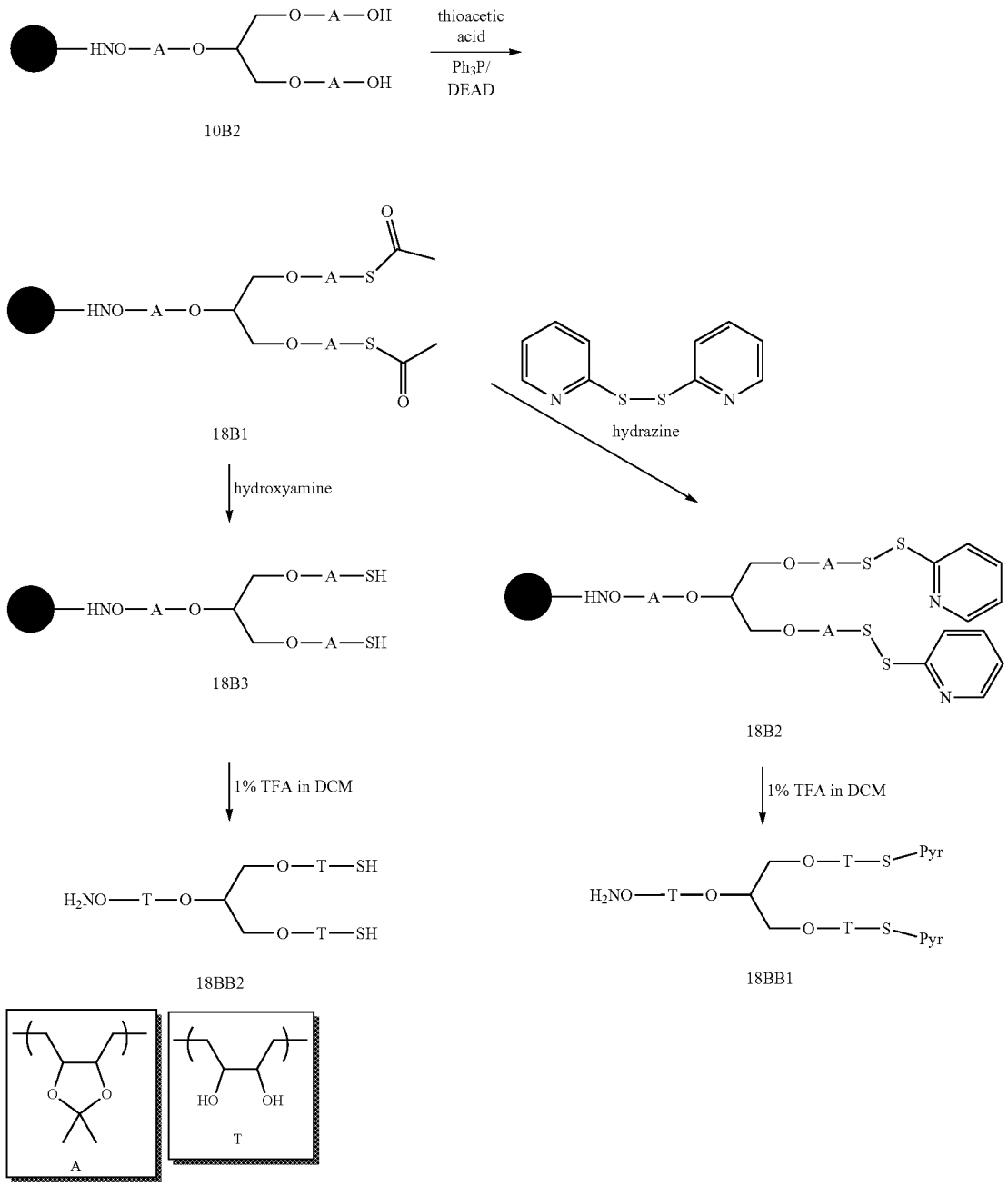

Scheme 18

Synthesis of 18B1: 18B1 is synthesized following a similar protocol as the linear SA molecule. Triphenylphosphine (0.126 g, 0.48 mmol) is added to a flask containing 10B2 (0.1 g resin containing 0.016 mmol of SA molecule). After flushing the flask with $N_2$, 2 mL of THF is added and the solution cooled below 4° C. DEAD (0.11 g, 0.64 mmol) is added, followed by drop-wise addition of 34 µL thioacetic acid (0.48 mmol). The reaction is warmed to RT and left on a shaker overnight. The resin is washed 6 times with 10 mL DCM and dried under vacuum to afford the desired product.

Synthesis of 18B2: 18B2 is synthesized following a similar protocol as the linear SA molecule. 2'-Aldrithiol (0.106 g, 0.48 mmol) and 24 µL hydrazine monohydrate (0.48 mmol) are added to a flask containing 10B1 (0.1 g resin containing 0.016 mmol of SA molecule) in 2 mL of DMF. The reaction is mixed for 2 h. The resin is washed 6 times with 10 mL DCM and dried under vacuum to afford the desired product.

Synthesis of 18B3: 18B3 is synthesized following the same protocol as 14B3. The resin is washed with DMF and DCM to afford the desired product.

Synthesis of 18BB1 and 18BB2: 18BB1 and 18BB2 are released from the resin following the same protocol as 13BB1. Solvent is removed under vacuum to afford the desired product.

Example 19: Synthesis of Bifurcated SA Monomer with Aminooxy Groups at the Branch Positions The following shows examples of bifurcated SA monomer wherein X of the $Z^1$ is —$ONH_2$ and X of the $Z^2$ and $Z^3$ is either —O—N(-phthalimidyl) or —$ONH_2$.

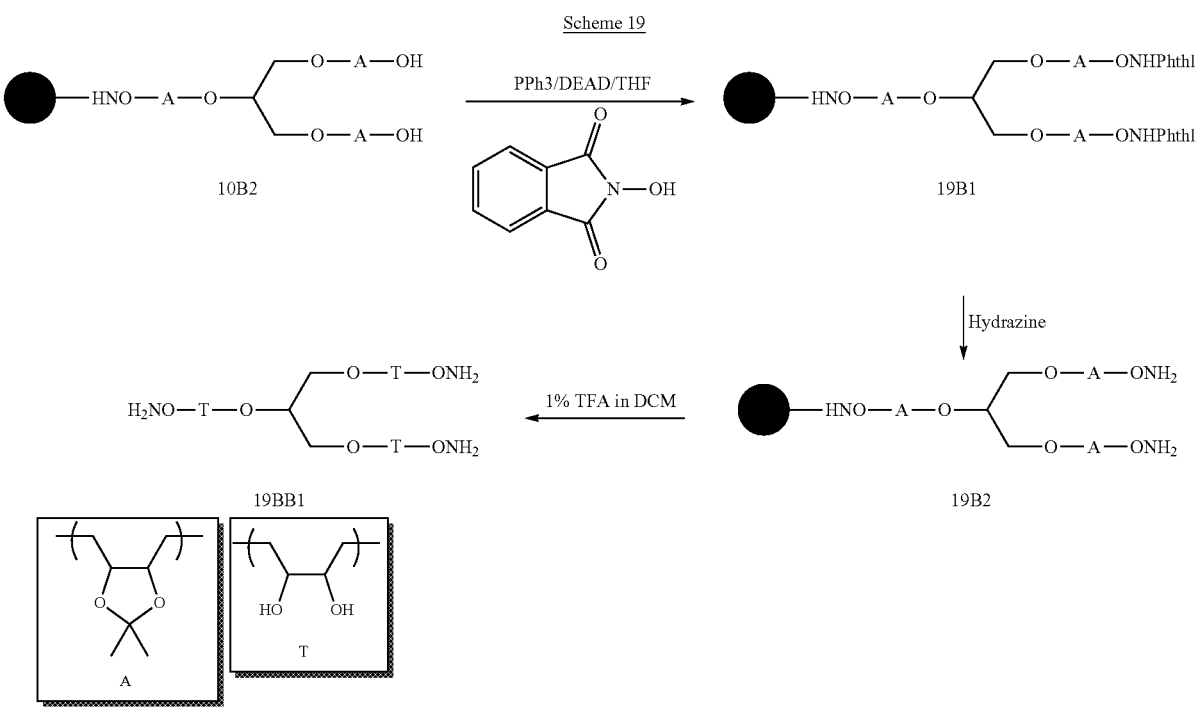

Scheme 19

Synthesis of 19B1: 19B1 is synthesized following the same protocol as 9B3, but using N—OH phthalimide instead. The resin is washed with DMF and DCM to afford the desired product.

Synthesis of 19B2: The phthalimidyl groups of 19B1 are removed by hydrazine following the same protocol as 9B4. The resin is washed with DMF and DCM to afford the desired product.

Synthesis of 19BB1: 19BB1 is released from the resin following the same protocol as 13BB1. The solvent is removed under vacuum to afford the desired product.

Example 20: Synthesis of Heterobifunctional Bifurcated SA Monomers with Aminooxy at Branched Positions
The following shows examples of bifurcated SA monomer wherein X of the $Z^1$ is —$NH_2$, —NH—C(=O)—$CH_2$-J, or —NH—C(=O)—$(CH_2)_2$—C(=O)OH, and X of the $Z^2$ and $Z^3$ is either —O—N-$(Boc)_2$ or —$ONH_2$.
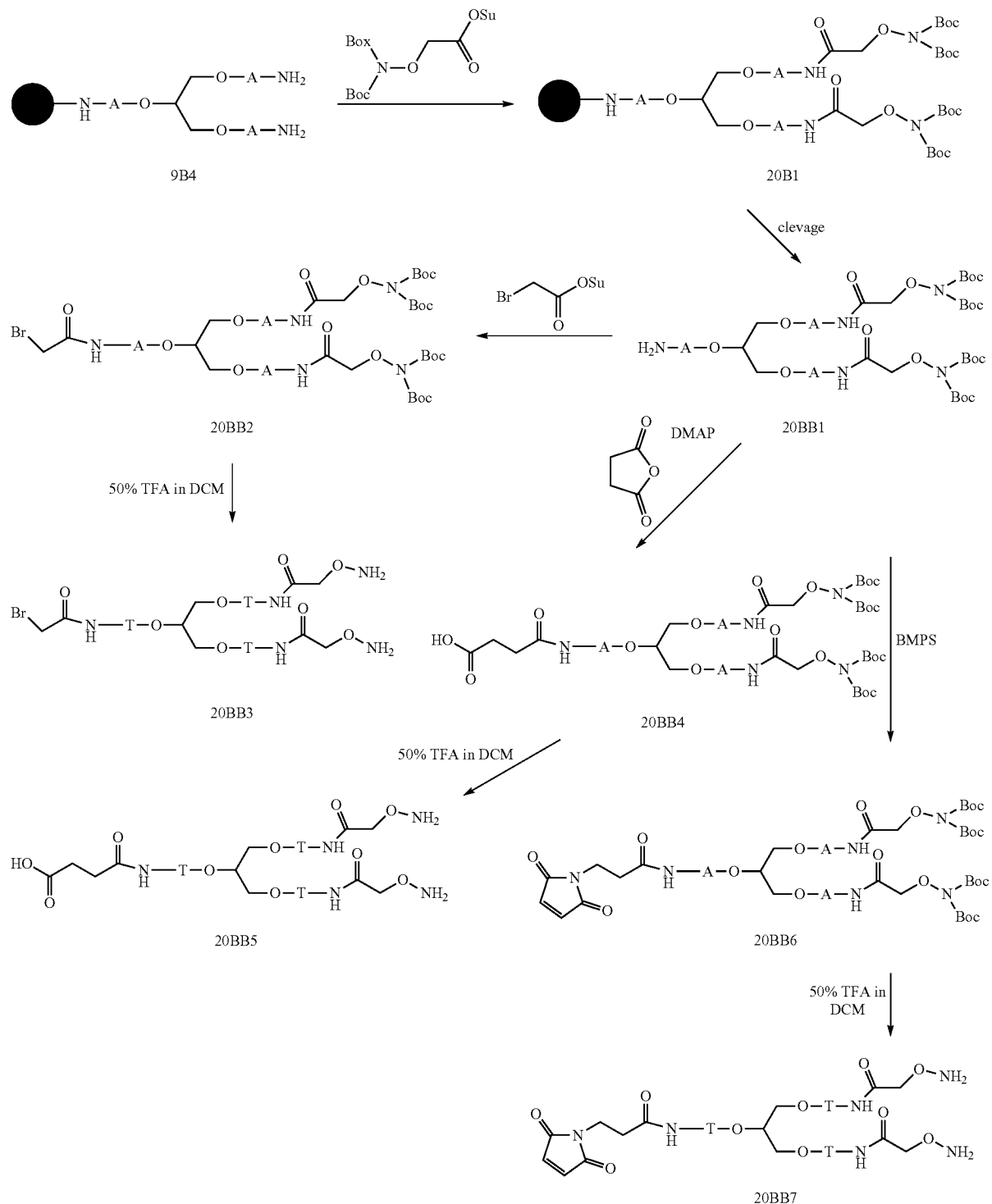

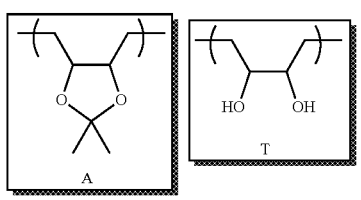

Synthesis of 20B1: 20B1 is synthesized following the standard NHS coupling protocol on solid support for 12B1. The resin is washed with DMF and DCM to afford the desired product. A small amount of resin can be taken out for the ninhydrin test.

Synthesis of 20BB1: 20BB1 is released from the resin following the exact protocol for 10BB2. The solvent is removed under vacuum to afford the product.

Synthesis of 20BB2 and 20BB6: 20BB2 and 20BB6 are synthesized following the standard NHS coupling protocol in solution for 12BB2. The progress of the reaction is monitored by HPLC. The final product is purified by HPLC and the structure confirmed by MS.

Synthesis of 20BB4: 20BB4 is synthesized following the same protocol as 15BB2. The progress of the reaction is monitored by HPLC. The final product is purified by HPLC and the structure confirmed by MS.

Synthesis of 20BB3, 20BB5, and 20BB7: The acetonide and Boc protecting groups of 20BB3, 20BB5, and 20BB7 are removed by 50% TFA in DCM (20 μL per mg of compound). The reaction mixture is stirred at RT for a few hours. The progress of the reaction is monitored by HPLC. The solvent is removed under vacuum to afford the desired product.

Example 21: Synthesis of Bifurcated SA Monomers Carrying an Aminooxy Functional Group at the Branched Position The following shows examples of bifurcated SA monomer wherein X of the $Z^1$ is —$NH_2$, and X of the $Z^2$ and $Z^3$ is either —O—N-(phthalimidyl) or —$ONH_2$.

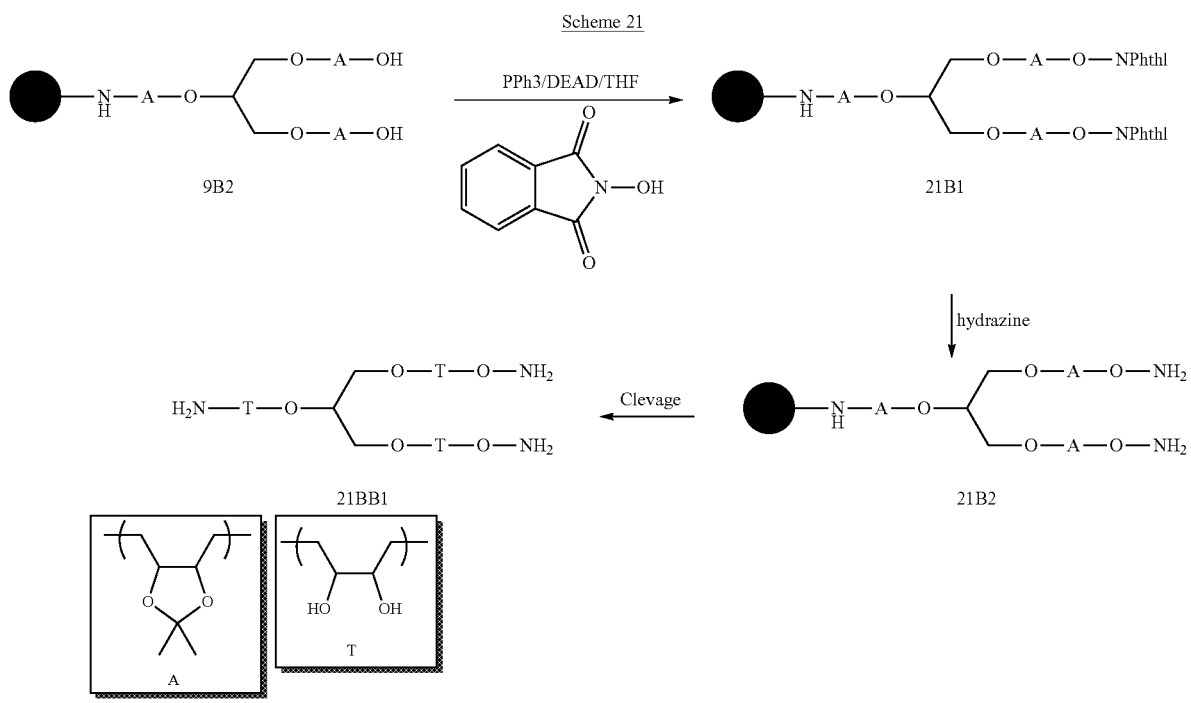

Synthesis of 21B1: 21B1 is synthesized following the same protocol as 19B1. The resin is washed with DMF and DCM to afford the desired product.

Synthesis of 21B2: The phthalimidyl groups of 21B1 are removed by hydrazine following the same protocol as 9B4. The resin is washed with DMF and DCM to afford the desired product.

Synthesis of 21BB1: 21BB1 is released from the resin following the same protocol as 13BB1. The solvent is removed under vacuum to afford the desired product.

Example 22: Synthesis of a Bifurcated SA Monomer for Repetitive Dendrimer Formation Via Amide Bond Formation The following shows an example of bifurcated SA monomer wherein X of the $Z^1$ is —$NH_2$ or —NH—C(=O)—$(CH_2)_2$—C(=O)OH, and X of the $Z^2$ and $Z^3$ is —NH-(Fmoc).

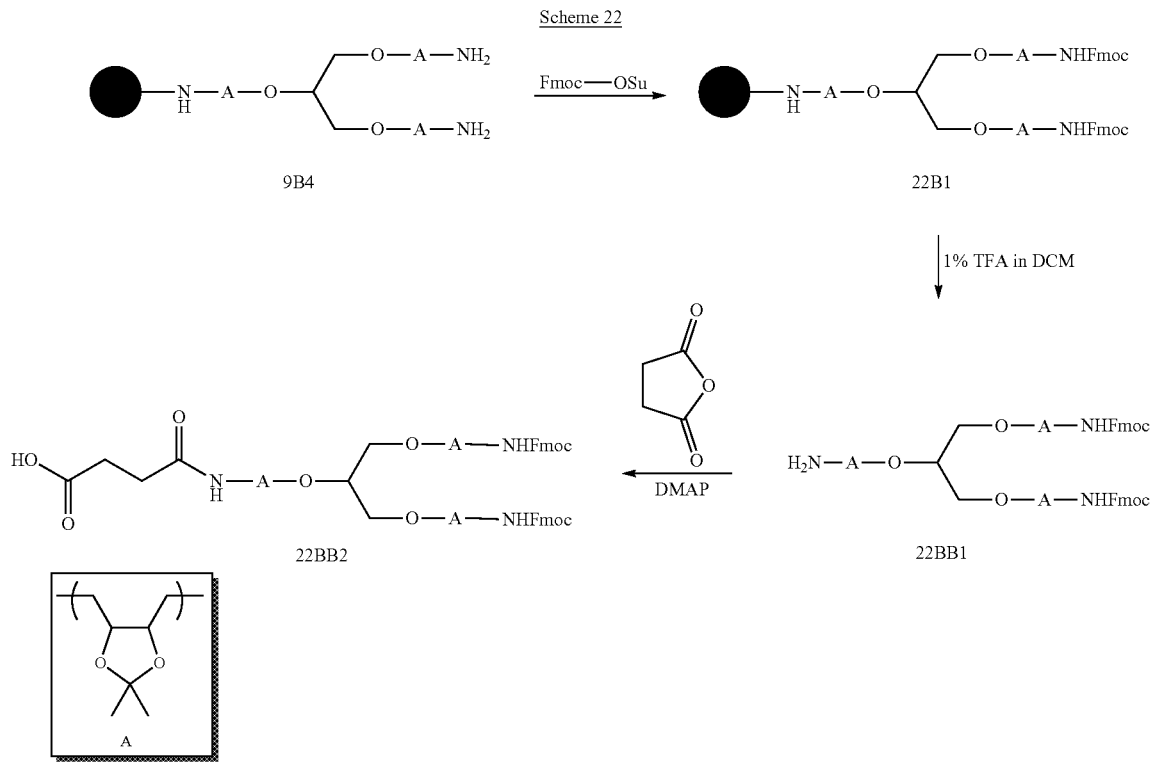

Synthesis of 22B1: 22B1 is synthesized following the standard NHS ester coupling protocol on solid support for 12B1. The resin is washed with DCM and DMF to afford the desired product. A small amount of resin is taken out for the ninhydrin test.

Synthesis of 22BB1: 22BB1 is released from the resin following the same protocol as 10BB2. Solvent is removed under vacuum to afford the desired product.

Synthesis of 22BB2: 22BB2 is synthesized following the same protocol as 15BB2. The progress of the reaction is monitored by HPLC. The final product is purified by HPLC and the structure confirmed by MS.

Example 23: Synthesis of a Bifurcated SA Unit for Dendrimer Formation Via Thiol Ether Formation The following shows an example of a bifurcated SA monomer wherein X of $Z^1$ is —NH—C(=O)—$CH_2$-J and X of the $Z^2$ and $Z^3$ is —NH—C(=O)—$(CH_2)_2$—S—S-pyr.

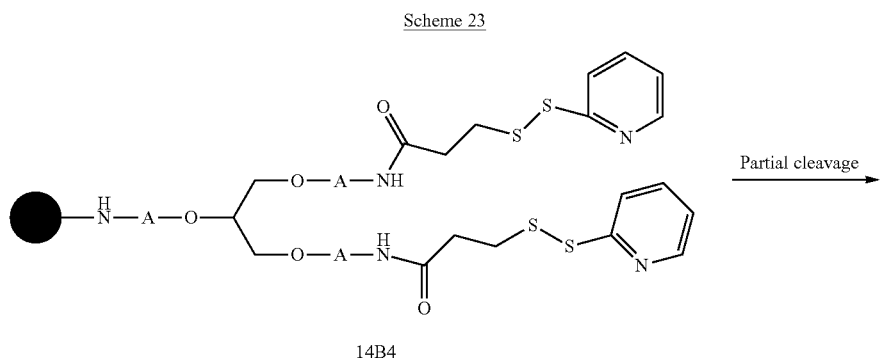

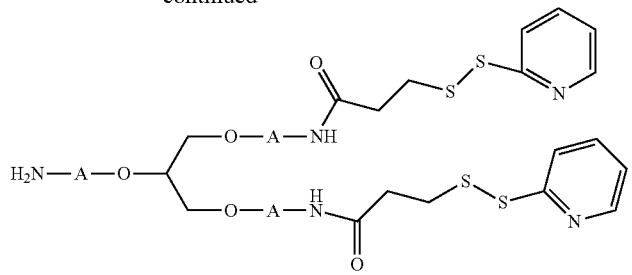

23BB1

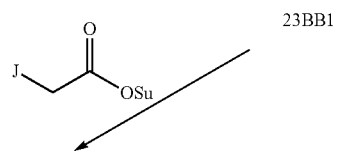

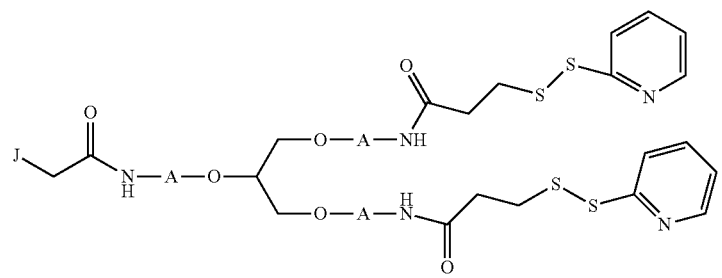

23BB2, J = I
23BB3, J = Br
23BB4, J = Cl

Synthesis of 23BB1: 14B4 is released from the resin following the same protocol as 10BB2. The solvent is removed under vacuum to afford the desired product.

Synthesis of 23BB2, 23BB3, and 23BB4: 23BB2-4 are synthesized following the standard NHS ester coupling protocol in solution for 12BB2. The progress of the reaction is monitored by HPLC. The final product is purified by HPLC and the structure confirmed by MS.

C. Examples of Dendrimer-Like SA Molecules

Example 24: Synthesis of Dendrimer-Like SA Molecules Via Reductive Amination

Scheme 24

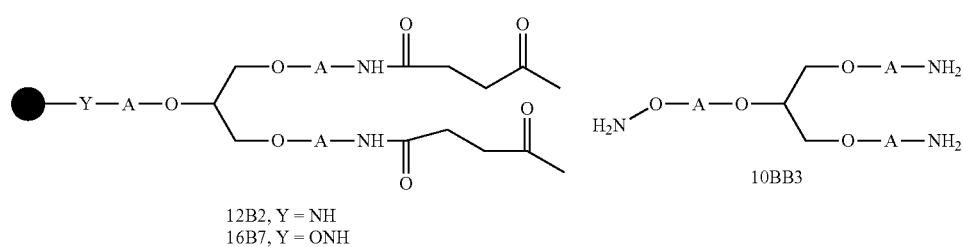

12B2, Y = NH
16B7, Y = ONH

10BB3

Step 1

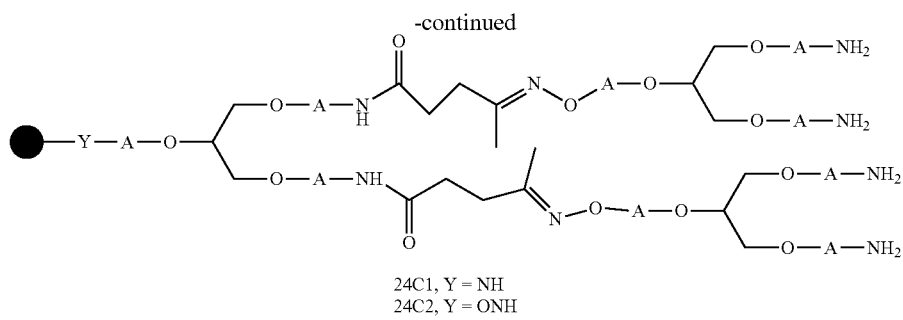

24C1, Y = NH
24C2, Y = ONH

Step 2
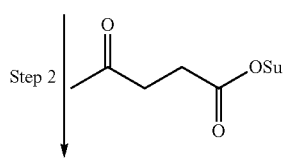

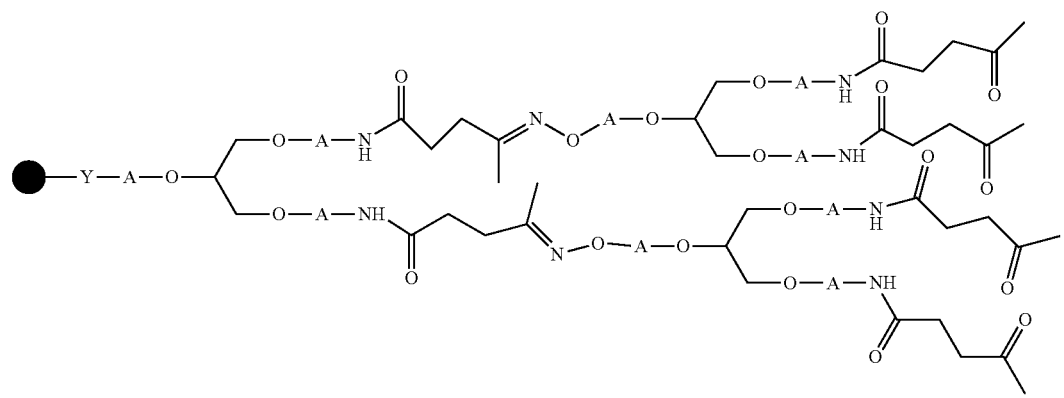

24C3, Y = NH
24C4, Y = ONH

Repeat

Higher order dendrimer

Synthesis of 24C$_1$ and 24C$_2$ (1$^{st}$ degree branch): 10 equiv. of 10BB3 in DMF with 0.1% TEA is added to a tube containing 100 mg of 12B2 or 16B7 (0.016 mmol). The solution and resin are mixed at RT overnight. The resin is washed with DCM and DMF to afford the desired product.

Synthesis of 24C3 and 24C4: 24C3 and 24C4 are synthesized following the same protocol as 12B2. The resin is washed with DCM and DMF to afford the desired product. A small amount of resin is taken out for the ninhydrin test.

Synthesis of higher order dendrimers: Repeat step 1 and step 2 to generate higher order dendrimers. Once a desired dendrimer is obtained, the resin is cleaved with 1% TFA in DCM to remove all protecting groups and afford the desired product.

Example 25: Synthesis of Dendrimer-Like SA Molecules Via Amide Bond Formation

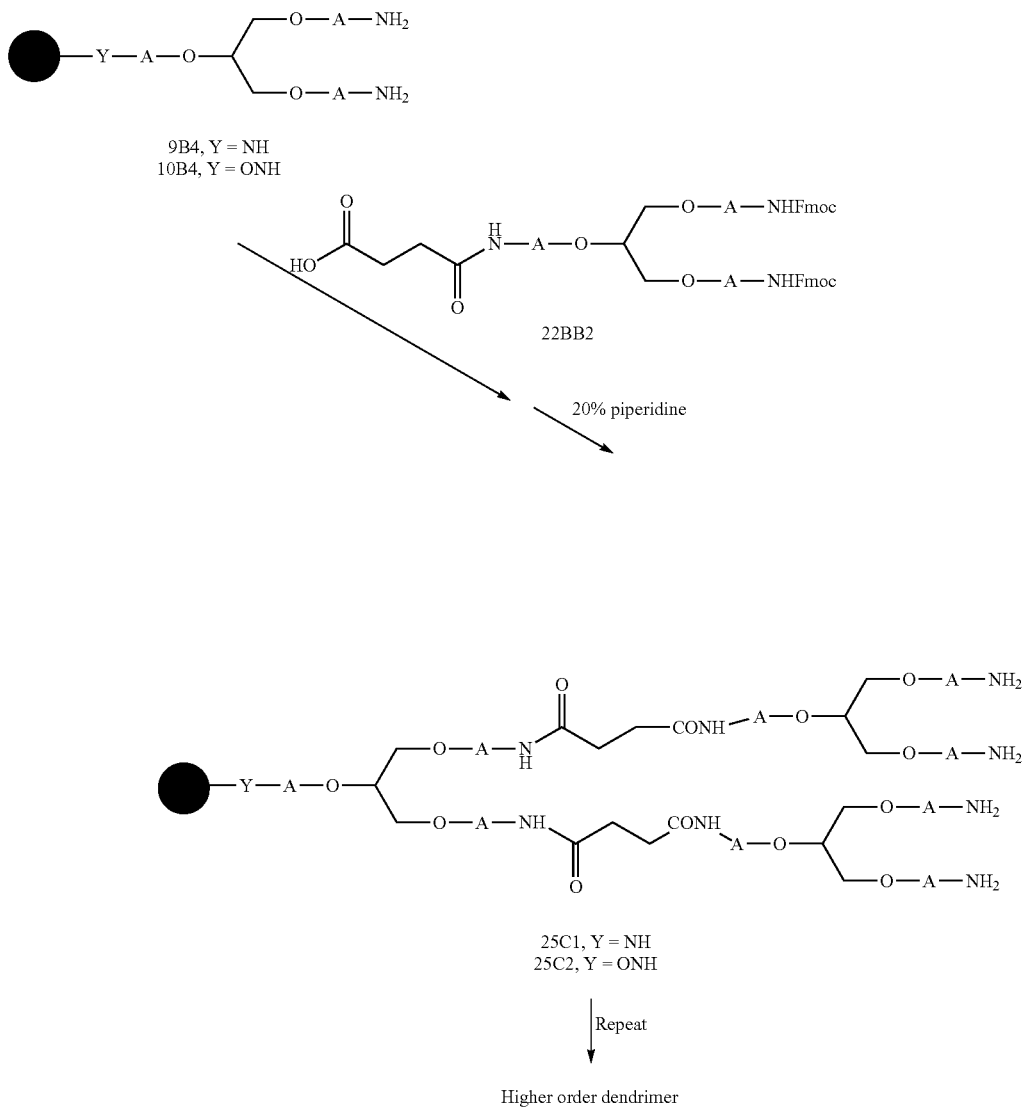

Scheme 25

Synthesis of 25C1 and 25C2 (1$^{st}$ degree branch): 25C1 and 25C2 are synthesized following the standard Fmoc solid phase peptide synthesis protocol. 22BB2 is first activated by mixing 1 equiv. of 22BB2 with 1 equiv. of HATU and 3 equiv. of DIPEA in DMF for 5 minutes. The final concentration of 22BB2 is 0.2M. 2.5 mL of this solution is added to a solid phase synthesis flask with a frit containing 100 mg of 9B4 or 10B4 (0.016 mmol). The solution and resin are mixed by bubbling N$_2$ at RT for a few hours to overnight. The progress of the reaction is checked by the ninhydrin test. After the reaction is complete, the resin is washed extensively with DMF. 10 mL of 20% piperidine in DMF is added to the resin. After 15 minutes, the resin is washed extensively with DMF to afford the desired product.

Synthesis of higher order dendrimers: Repeat the synthesis steps of 25C1 to generate higher order dendrimers. Once a desired dendrimer is obtained, the resin is cleaved with 1% TFA in DCM to remove all protecting groups and afford the desired product.

Example 26: Synthesis of Dendrimer-Like SA Molecules Via Thiol Ether Formation

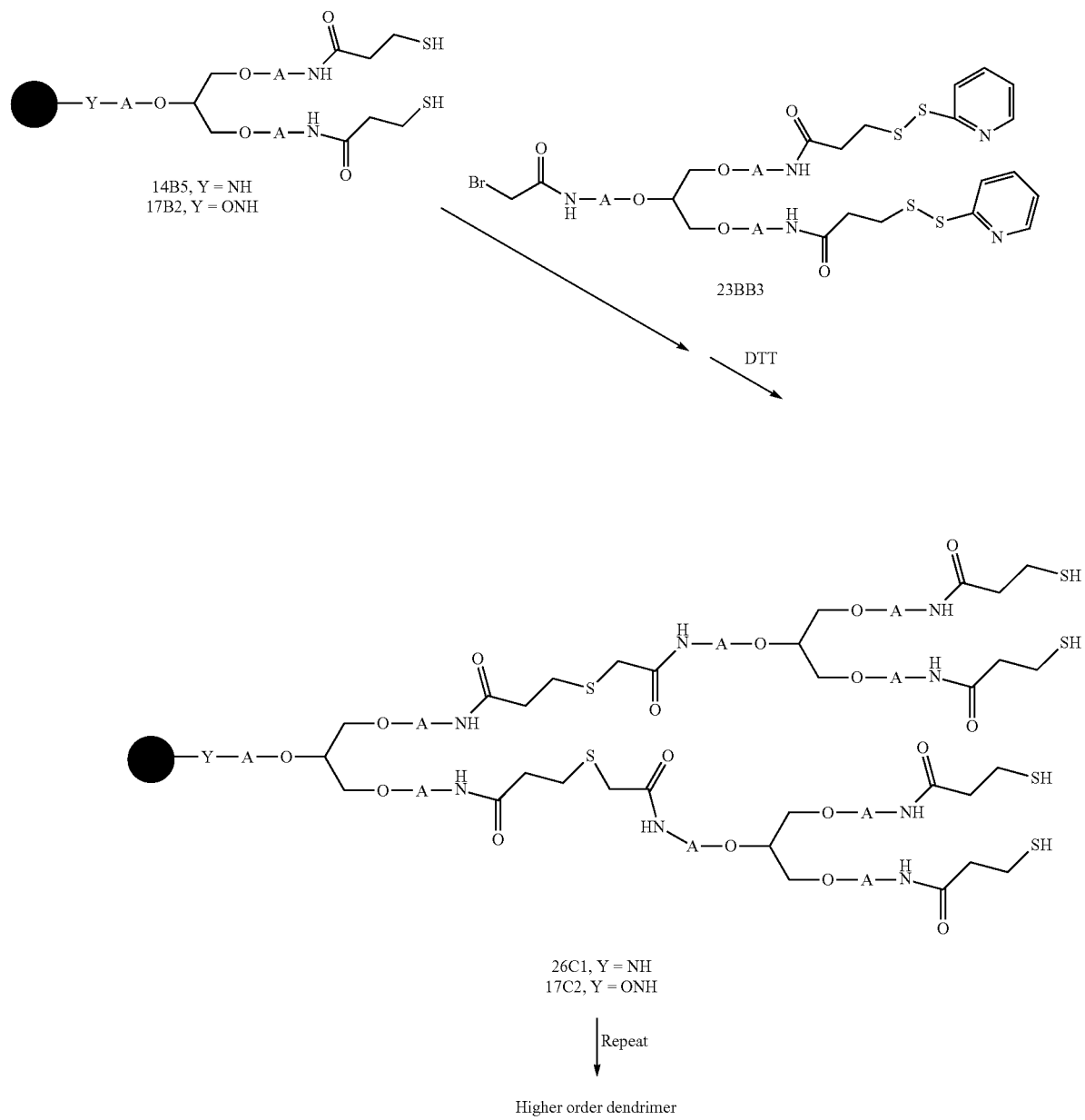

Synthesis of 26C1 and 26C2 (1$^{st}$ degree branch): 10 equiv. of 23BB3 in 2 mL of DMF with 0.1% DIPEA is added to a solid phase synthesis flask with a frit containing 100 mg of 14B5 or 17B2 (0.016 mmol). The solution and resin are mixed by bubbling $N_2$ at RT for a few hours to overnight. The progress of the reaction is checked by the ninhydrin test. After completion of the reaction, the resin is washed extensively with DMF. 10 mL of 0.2M DTT solution in DMF is then added to the resin. After 1 h, the solvent is removed and the resin washed extensively with DMF to afford the desired product.

Synthesis of higher order dendrimers: Repeat the synthesis steps of 26C1 to generate higher order dendrimers. Once a desired dendrimer is obtained, the resin is cleaved with 1% TFA in DCM to remove all protecting groups and afford the desired product.

D. Examples of the Preparation of Conjugates $M_1$-$(L_2$-B$)_r$ or $M_1$-$(L_2$-$B_1)_r$.

The following shows examples of labeling various molecules or solid support with heterobifunctional bifurcated SA monomers. The methods are generally taken from standard bioconjugation protocols in Greg Hermanson's book (Bioconjugation Techniques, 2$^{nd}$ Edition, 2018, ISBN: 978-0-12-370501-3) or from CellMosaic. The usage of dendrimer-like SA molecules for labeling is the same as the bifurcated SA monomers.

Example 27: Preparation of $M_1$-$(L_2$-$B)_r$ Using Carboxylic and Keto Bifurcated SA Monomer (15BB3 as an Example)

Scheme 27

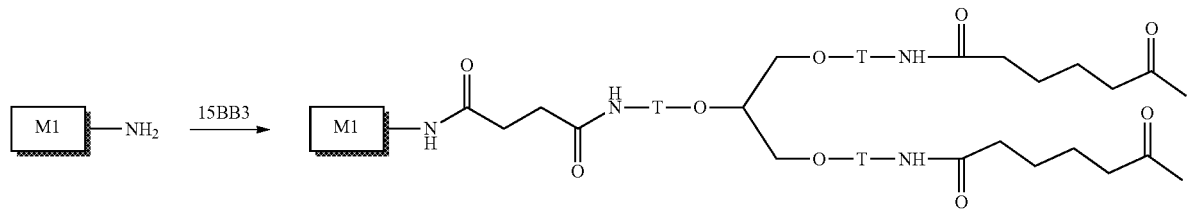

Labeling antibody (IgG) with 15BB3: Antibody (3 mg) is dissolved or buffer exchanged into 0.1M MES, 0.15M NaCl, pH 4.7 (reaction buffer) at a concentration of 10 mg/ml (total 300 µL). To this solution, add 100-500 µL of 4 mg/mL of 15BB3 solution in reaction buffer, followed by 50-400 µL of 10 mg/mL EDC in water. After reacting at RT for 2 h, unreacted 15BB3 is removed by gel filtration or dialysis. Note: the amount of 15BB3 and EDC can be adjusted depending on the extent of the antibody labeling (the number of r).

Labeling peptide with 15BB3: A 15-mer peptide (3 mg) with free N-terminal amine is dissolved in 0.1M MES, 0.15M NaCl, pH 4.7 (reaction buffer) at a concentration of 10 mg/mL (total 300 µL). To this solution, add 300 µL of 10 mg/mL 15BB3 solution in reaction buffer, followed by 10 mg of solid EDC. After reacting at RT for 2 h, the conjugate is purified by a C18 HPLC column using the standard TFA system for peptide. Note: if there are Lys residues in the peptide, the ε-amino groups of these Lys residues will also be labeled. To prevent labeling of the ε-amino groups of Lys, amino groups can be protected with trityl during the peptide synthesis. After conjugation and purification, the trityl group is removed in 1% TFA in water.

Labeling oligo with 15BB3: A 15-mer oligo (3 mg) with 5' C6 amino modification is dissolved or buffer exchanged into 0.1M MES, 0.15M NaCl, pH 4.7 (reaction buffer) at a concentration of 10 mg/mL (total 300 µL). To this solution, add 300 µL of 10 mg/mL 15BB3 solution in reaction buffer, followed by 10 mg of solid EDC. After reacting at RT for 2 h, the conjugate is purified by a C18 HPLC column using the standard TEAA system for oligo.

Labeling HRP or proteins with 15BB3: The procedure for labeling HRP or protein with 15BB3 is similar to the procedure for antibody. Unreacted 15BB3 is removed by gel filtration or dialysis.

Labeling small molecules with 15BB3: A small molecule carrying an amino group can be labeled with 15BB3 in a similar way as peptide. If the small molecule is not soluble in water, then DMSO can be added to the buffer up to 50% (v/v). The final conjugate is purified by C18 HPLC using the standard TFA system.

Labeling agarose beads with 15BB3: 4% cross-linked agarose beads containing amino functional groups were either purchased commercially or prepared following literature protocols (Jose M. Guisan Immobilization of Enzymes and Cells, Volume 1 of the series Methods in Biotechnology 2006, pp 277-287. C. Mateo et al. Enzyme and Microbial Technology, vol. 36, pp. 447-454, 2005). 4% agarose beads were first treated with sodium periodate to obtain agarose beads with 10-15 µmoles glyoxyl groups per ml of beads. The glyoxyl beads were further reacted with ethylenediamine and the resulting shift bases were reduced by sodium borohydride to afford the agarose beads containing amino groups. Amino agarose beads (10 mL settle down beads) are then suspended in 20 mL of 0.1M MES, 0.15M NaCl, pH 4.7 (reaction buffer). 10 mL of 20 mg/ml of 15BB3 solution in reaction buffer is added, followed by 10 mL of 50 mg/mL EDC in water. After reacting at RT for 2 h, agarose beads are transferred to a filtration setup with a Buchi Funnel and the beads are washed extensively with deionized buffer to obtain the agarose beads with SA molecule attached (Note: the amount of 15BB3 and EDC can be adjusted depending on the loading requirement (the number of r).

Labeling poly(methyl methacrylate)(PMMA) beads with 15BB3: PMMA beads were functionalized with amino groups following literature protocol (Fixe F. et al. Nucleic acid research 2004, 32 (1), e9.). PMMA beads were treated with ethylene diamine to obtain the amino functioned PMMA beads. A typical batch contains 500 nmole amino functional groups per ml of settled down beads. The amino PMMA is then reacted with 15BB3 (10 mole equivalent of amino groups) in the presence of EDC (50 equivalent of amino groups) following same protocol as agarose beads. The amount of 15BB3 and EDC can be adjusted depending on the loading requirement (the number of r).

Example 28: Preparation of $M_1$-$(L_2$-$B)_r$ Using Bromoacetyl and Aminooxy Bifurcated SA Monomer 20BB3

Scheme 28

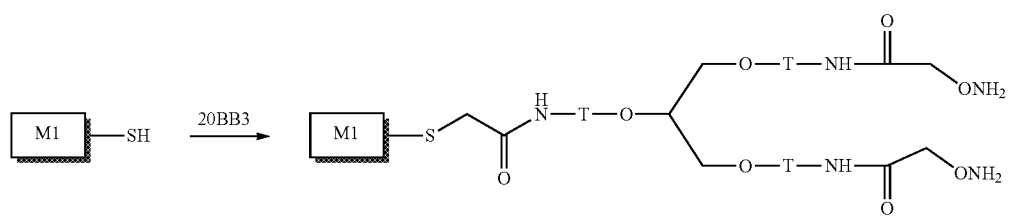

Labeling antibody (IgG) with 20BB3: Antibody (3 mg) is dissolved or buffer exchanged into 500 µL of 0.1M sodium phosphate, 0.15M NaCl, 10 mM EDTA, pH 7.2 (reaction buffer). To this solution, add 3 mg of 2-mercaptoethylamine (MEA) and then incubate the mixture at 37° C. for 1.5 h. The solution is then loaded onto a NAP-5 desalting column (GE bioscience) pre-equilibrated with reaction buffer. The reduced antibody is eluted with 1.0 mL of reaction buffer and 20BB3 added to a final concentration equal to 10 mole equivalents per mole of antibody. After reacting at RT for 2 h, unreacted 20BB3 is removed by gel filtration or dialysis. The average loading of 20BB3 is around 2-4.

Labeling peptide with 20BB3: A 15-mer peptide (3 mg) with a free Cys is dissolved in 0.1M sodium phosphate, 0.15M NaCl, 10 mM EDTA, pH 7.2 (reaction buffer) at a concentration of 10 mg/mL (total 300 µL). To this solution, 20BB3 is added to a final concentration equal to 2 mole equivalents per mole of peptide. After reacting at RT for 2 h, the conjugate is purified by a C18 HPLC column using the standard TFA system for peptide.

Labeling oligo with 20BB3: A 15-mer oligo (3 mg) with 5' or 3' disulfide modifier is dissolved in 0.1M sodium phosphate, 0.15M NaCl, 10 mM EDTA, pH 7.2 (reaction buffer) at a concentration of 10 mg/mL (total 300 µL). To this solution, TCEP is added to a final concentration equal to 10 mole equivalents per mole of oligo. The solution is mixed at 37° C. for 1.5 h. Oligo is then precipitated out by ethanol and dissolved in 300 µL of reaction buffer. To this solution, 20BB3 is added to a final concentration equal to 2 mole equivalents per mole of peptide. After reacting at RT for 2 h, the conjugate is purified by a C18 HPLC column using the standard TEAA system for oligo.

Labeling HRP or proteins with 20BB3: Protein (3 mg) is dissolved or buffer exchanged into 500 µL of 0.1M sodium phosphate, 0.15M NaCl, 10 mM EDTA, pH 7.2 (reaction buffer). To this solution, add 2-iminothiolane to give a molar excess of 20-40× over the amount of protein present. The solution is mixed at RT for 1 h. The solution is then loaded onto a NAP-5 desalting column (GE bioscience) pre-equilibrated with reaction buffer. The thiol protein is eluted with 1.0 mL of reaction buffer and 20BB3 added to a final concentration equal to 10 mole equivalents per mole of antibody. After reacting at RT for 2 h, unreacted 20BB3 is removed by gel filtration or dialysis.

Labeling small molecules with 20BB3: A small molecule carrying a thiol group can be labeled with 20BB3 in a similar way as Cys peptide. If the small molecule is not soluble in water, then DMSO can be added to the buffer up to 50% (v/v). The final conjugate is purified by C18 HPLC using the standard TFA system.

E. Examples of Preparation of Conjugates B-$(L_1$-$M_2)_q$

The following shows examples of labeling various molecules with heterobifunctional bifurcated SA monomers. The usage of dendrimer-like SA molecules for labeling is the same as for the bifurcated SA monomers.

Example 29: Loading Small Molecules with Free Thiol onto a Bifurcated SA Monomer (Mertansine DM1 as an Example)

Scheme 29

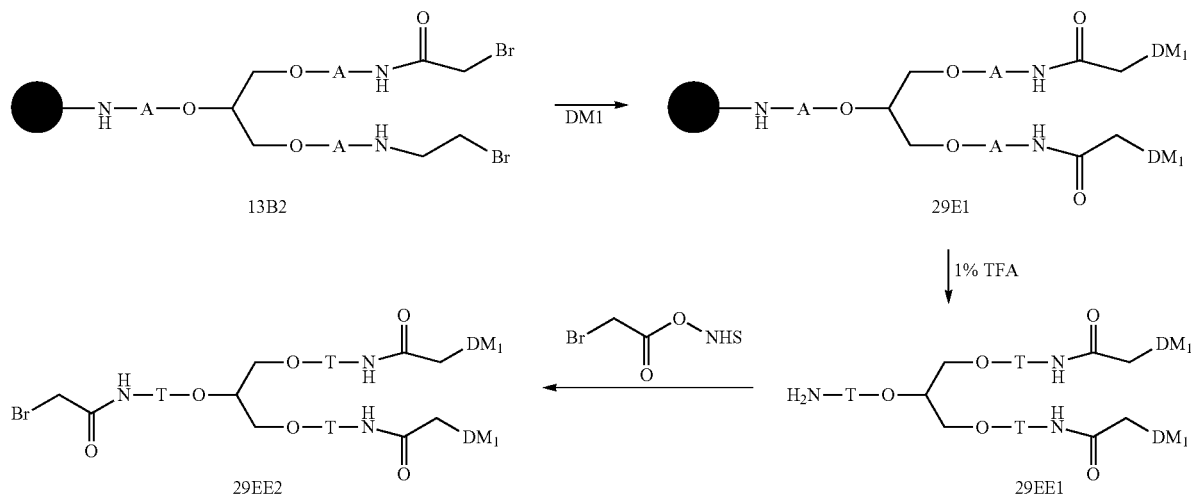

Synthesis of 29E1: DM1 (mertansine) is coupled to 13B2 following the same protocol as linear SA molecule. 143.5 μL of 0.4M DIPEA solution in NMP and 861 μL of 0.05M mertansine solution in NMP are added to a tube containing 111 mg of 13B2 (~0.018 mmol of SA monomer). After incubating at RT overnight, the resin was washed extensively with DCM and DMF to afford the desired product.

Synthesis of 29EE1: 29EE1 is released from the resin following the same protocol as 13BB1. The solvent was removed under vacuum to afford the desired product.

Synthesis of 29EE2: 29EE2 is synthesized following the standard NHS coupling protocol in solution for 12BB2. The progress of the reaction is monitored by HPLC. The final product is purified by HPLC and the structure confirmed by MS.

Example 30: Loading Small Molecules with Carboxylic Acid onto a Bifurcated SA Monomer with an Aminooxy Group (Fluorescein and Biotin as an Example)

-continued

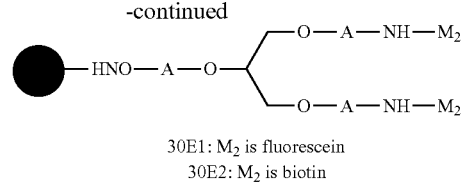

30E1: $M_2$ is fluorescein
30E2: $M_2$ is biotin

30EE1: $M_2$ is fluorescein
30EE2: $M_2$ is biotin

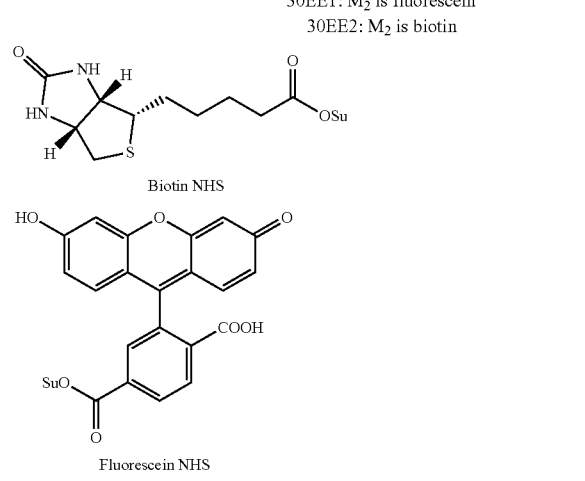

Biotin NHS

Fluorescein NHS

Scheme 30

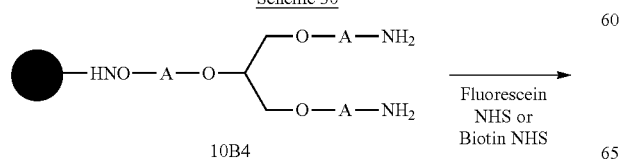

Synthesis of 30E1: 30E1 was synthesized following a similar NHS ester coupling protocol on solid support as 12B1. 6-FAM NHS ester (7 equiv.) and DIPEA (18 equiv.) dissolved in 1.3 mL of a mix solvent of NMP/DCM (3:1) were added to a tube containing 170 mg of 10B4 (~0.034 mmol SA monomer). After incubating at RT overnight, the resin was washed extensively with DCM and DMF to afford the desired product.

Synthesis of 30E2: 30E2 is synthesized following the same NHS ester coupling protocol on solid support for 12B1. After incubating at RT overnight, the resin is washed extensively with DCM and DMF to afford the desired product.

Synthesis of 30EE1: 30EE1 was released from the resin following the same protocol as 13BB1. The solvent was removed under vacuum to afford the desired product.

Synthesis of 30EE2: 30EE2 is released from the resin following the same protocol as 13BB1. The solvent is removed under vacuum to afford the desired product.

Example 31: Loading Small Molecules with Carboxylic Acid onto a Bifurcated SA Monomer with a Thiol Reacting Group (Biotin and Fluorescein as an Example)

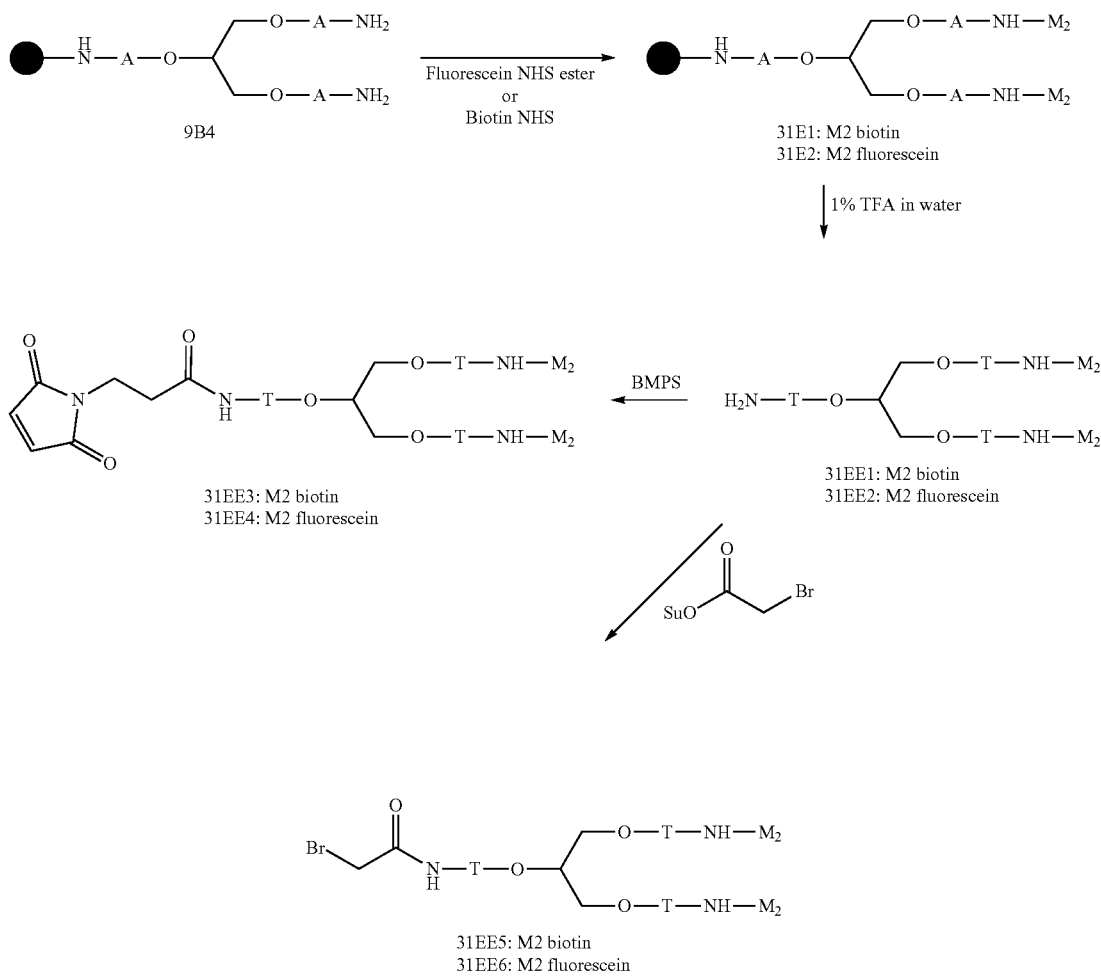

Synthesis of 31E1 and 31E2: 31E1 and 31E2 are synthesized following the same NHS ester coupling protocol on solid support for 12B1. After incubating at RT overnight, the resin is washed extensively with DCM and DMF to afford the desired product.

Synthesis of 31EE1 and 31EE2: 31EE1 and 31EE2 are released from the resin following the same protocol as 13BB1. The solvent was removed under vacuum to afford the desired product.

Synthesis of 31EE3, 31EE4, 31EE5, and 31EE6: 31EE3-6 are released from the resin following the same protocol as 13BB1. The solvent is removed under vacuum to afford the desired product.

Example 32: Labeling Bifurcated SA Monomer with Ketone-Containing Small Molecules on Solid Phase (Doxorubicin as an Example)

A small molecule containing a keto group, such as doxorubicin, can be coupled to a bifurcated SA molecule containing an aminooxy functional group on solid phase.

Scheme 32

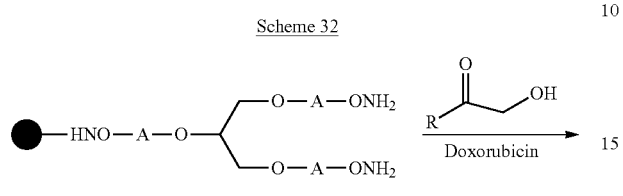

19B2

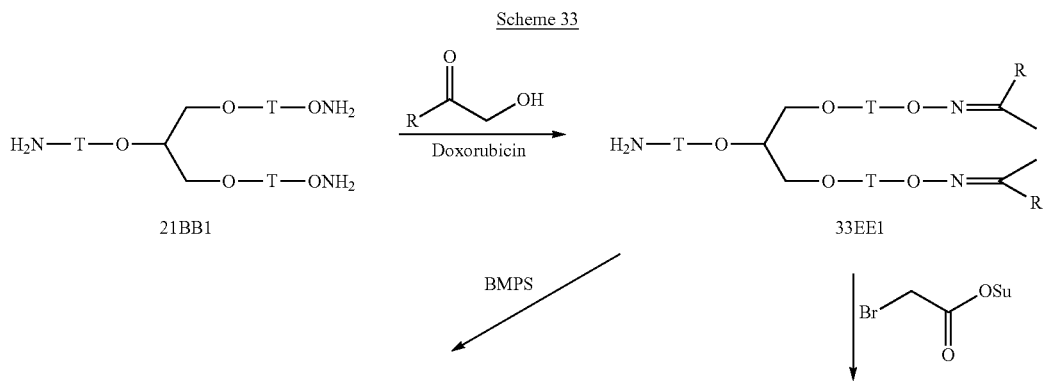

32E1

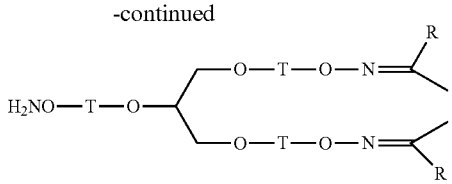

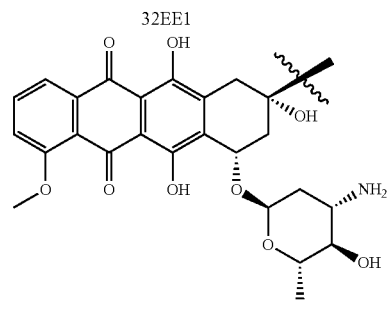

32EE1

Synthesis of 32E1: 10 equiv. of doxorubicin in DMF with 0.1% TEA is added to a tube containing 100 mg of 19B2 (~0.016 mmol of SA monomer). The solution and resin are mixed at RT overnight. The resin is washed extensively with DCM and DMF to afford the desired product.

Synthesis of 32EE1: 32EE1 is released from the resin following the same protocol as 13BB1. The solvent was removed under vacuum to afford the desired product.

Example 33: Labeling Bifurcated SA Monomer with Ketone-Containing Small Molecules in Solution (Doxorubicin as an Example)

Scheme 33

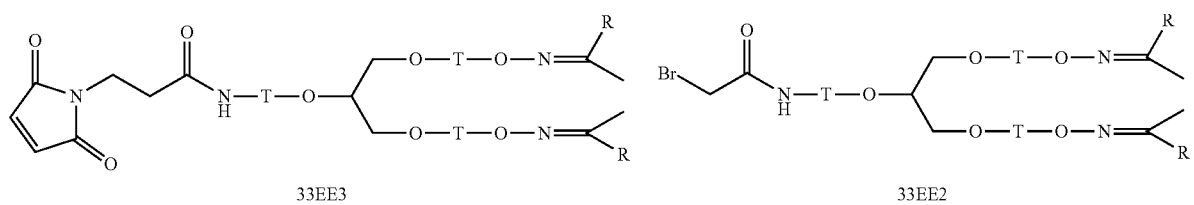

21BB1                        33EE1

33EE3                        33EE2

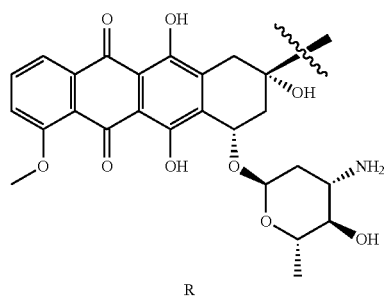

R

Synthesis of 33EE1: 0.5 mL of doxorubicin hydrochloride (7 mg, 1 equiv.) in water is added to a centrifuge tube containing 5 mg of 21BB1 in 0.5 mL of 0.1% acetic acid solution. The solution is mixed at RT overnight. The solvent is removed under vacuum to afford the product.

Synthesis of 33EE2 and 33EE3: 33EE2 and 33EE3 are synthesized following the standard NHS ester coupling protocol in solution for 12BB2. The progress of the reaction is monitored by HPLC. The final product is purified by HPLC and the structure confirmed by MS.

Example 34: Labeling Bifurcated SA Monomer with OH-Containing Small Molecule (SN38 as an Example)

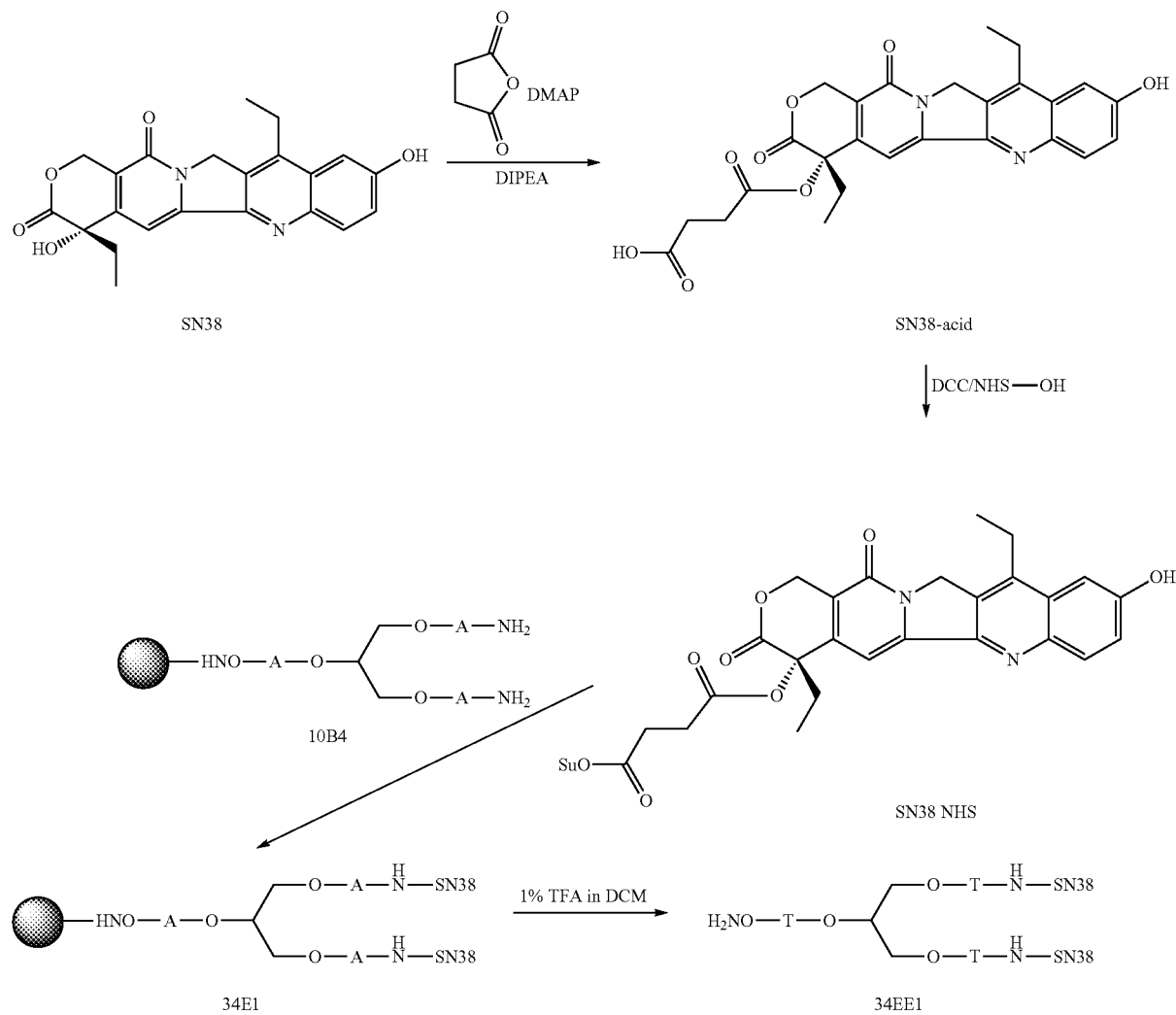

Synthesis of SN38-acid: DMF (2.5 mL) and DIPEA (784 μL) were added to a 5 mL vial containing SN38 (199 mg, 0.5 mmol) and succinic anhydride (304 mg, 3 mmol). After stirring at RT for a few minutes, DMAP (122 mg, 1 mmol) was added directly into the solution as a solid. The reaction mixture was heated at 45° C. overnight. A large excess of water was added and the pH of the solution adjusted to 2 by adding 2M HCl. Bluish or dark solid precipitated out. The solid was washed with water three times and then dried under vacuum to afford 200 mg of product (80% yield). MS confirms the structure (ESI-MS: M+H: 492.3).

Synthesis of SN38 NHS ester: SN-38 acid (50 mg, 0.102 mmol), N-hydroxy succinimide (16.6 mg, 0.144 mmol), dicyclohexlcarbodiimide (DCC, 25 mg, 0.12 mmol), and 0.5 mL of DMF were added sequentially to a 1.5 mL centrifuge tube. The mixture was heated at 45° C. for 2 h. The solid precipitate was filtered out. Ether was added to the filtrate to precipitate the product. The product was washed with ether three times and then dried under vacuum to afford 45 mg of product (75% yield).

Synthesis of 34E1: 34E1 is synthesized following the standard NHS ester coupling protocol in solution for 12BB2. The progress of the reaction is monitored by HPLC. The final product is purified by HPLC and the structure confirmed by MS.

Synthesis of 34EE1: 34EE1 is released from the resin following the same protocol as 13BB1. The solvent was removed under vacuum to afford the desired product.

Example 35: Labeling Bifurcated SA Monomer with NH$_2$-Containing Small Molecule (Doxorubicin as an Example)

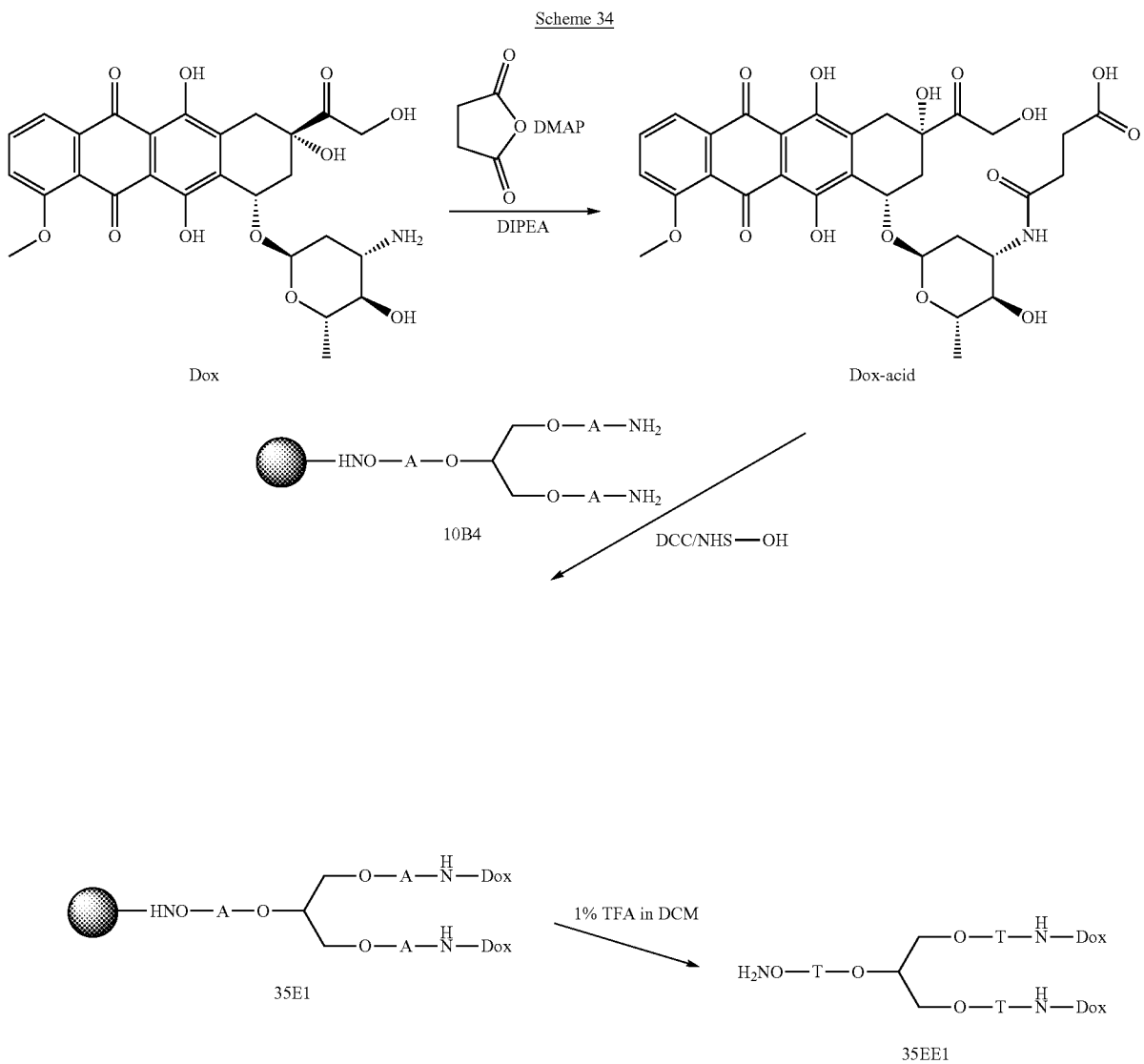

Scheme 34

Synthesis of Dox-acid: Dox-acid was synthesized following the literature protocol (Synthetic Communications, 2003, 33 (14), 2401-2421). DMF (54 mL) was added to a flask containing doxorubicin HCl salt (0.41 g, 0.707 mmol), followed by 0.613 mL of DIPEA. The flask was wrapped with aluminum foil and the reaction mixture stirred at RT under $N_2$ for 30 minutes. 13.6 mL of DMF and 2.453 mL of DIPEA were added to a separate flask containing succinic anhydride (0.564 g, 5.64 mmol). The doxorubicin solution was added to the succinic anhydride solution drop-wise over 10 minutes. After stirring the reaction mixture at RT in the dark for 2 h, 5 mL of 20% MeOH in water was added and stirred for another 30 minutes. The solvent was removed and the oily residue mixed with a solution of 50% MeOH in water. The mixture was placed in an ultrasonic bath for 2 min at RT before allowing to stand for 3 h at 4° C. The solid precipitate was further purified by HPLC to afford 0.16 g of final product (48%). MS confirms the structure.

Synthesis of 35E1: 35E1 is synthesized following the standard NHS ester coupling protocol on solid support for 12B1. However, the NHS ester is generated following the same protocol as SN38 NHS ester, but without ether precipitation. The NHS ester formed in DMF solution is added directly to the solid support. After the reaction, the resin is washed with DMF and DCM to obtain the desired product. A small amount of resin can be taken out for the ninhydrin test.

Synthesis of 35EE1: 35EE1 is released from the resin following the same protocol as 13BB1. The solvent was removed under vacuum to afford the desired product.

F. Conjugates $M_1$-($L_1$-B-($L_1$-$M_2$)q)r

The following shows examples of linking various molecules together with heterobifunctional bifurcated SA monomers. The methods are generally taken from standard bioconjugation protocols in Greg Hermanson's book (Bioconjugation Techniques, $2^{nd}$ Edition, 2018, ISBN: 978-0-12-370501-3) or from CellMosaic unless otherwise stated. The usage of dendrimer-like SA molecules for labeling is the same as the bifurcated SA monomers. The advantages of using bifurcated SA crosslinkers over other crosslinkers are obvious in these examples because bifurcated SAs are so hydrophilic that little or no organic solvent is needed for the reaction. Particularly in the cases of drug, biotin, and fluorescent dye labeling of an antibody, the SA molecule will greatly reduce the hydrophobicity of the small molecule and make it easy to react it with an antibody in the aqueous buffer after modification. One can also expect less aggregation and more stable conjugate.

Example 36: Site-Specific Labeling Antibody with SA Molecule Labeled with DM1

Scheme 36

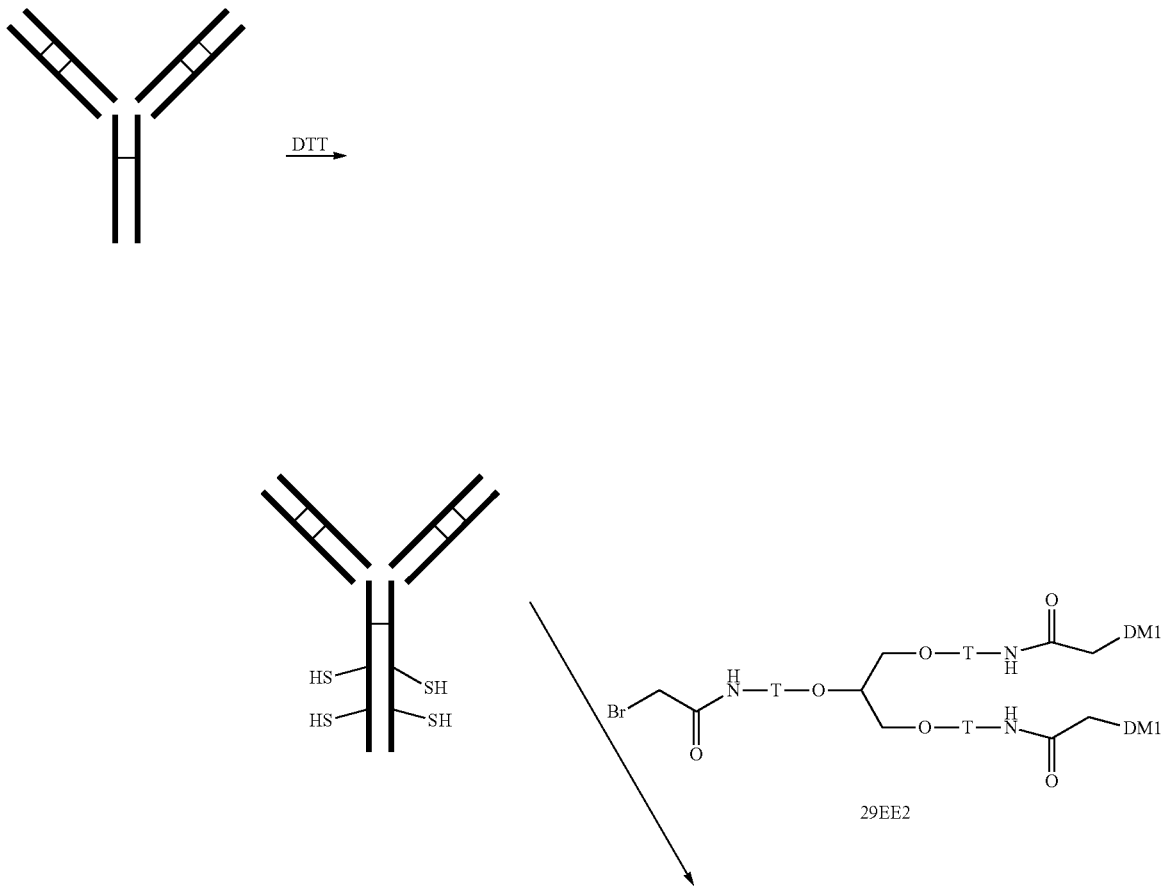

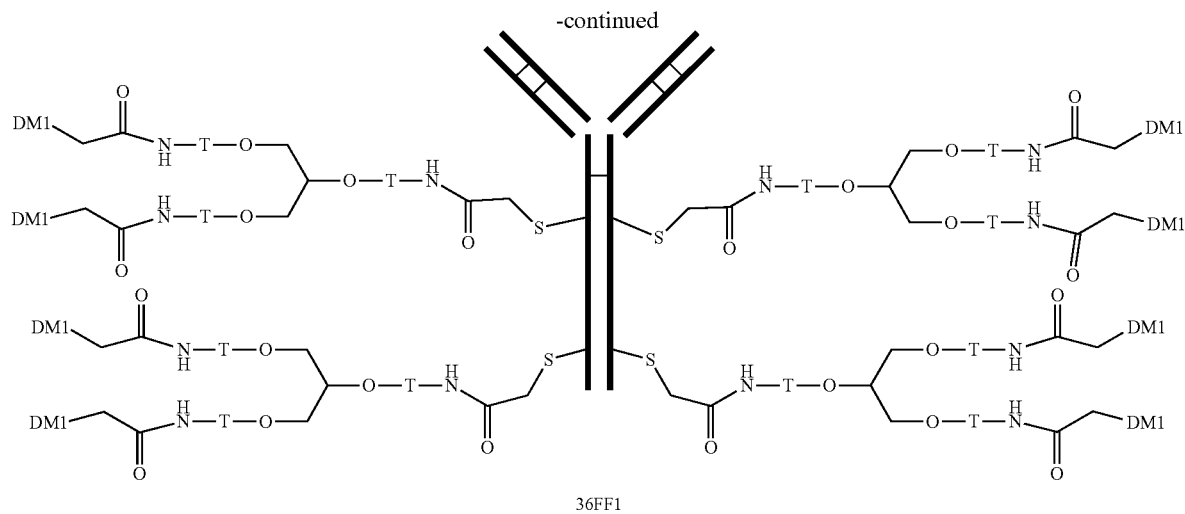

36FF1

Synthesis of 36FF1: Antibody is reduced following the literature procedure (Michael M. C. et al. Bioconjugate Chem. 2005, 16, 1282-1290). Briefly, antibody (3 mg) is treated with 3.25 molar equiv. of DTT in 0.5 mL of 25 mM sodium borate, pH 8.0, 25 mM NaCl buffer for 2 h at 37° C. The partially reduced antibody is purified by passing through a NAP-5 column (GE bioscience). The product is eluted out with 1 mL of 10 mM sodium phosphate, 10 mM NaCl, pH 7.0 buffer, and then 4 molar equiv. of 29EE2 in water is added. The solution is mixed at RT for 1 h. The unreacted 29EE2 is removed by gel filtration. The final product is analyzed by size exclusion HPLC to check the aggregation profile. Due to the extreme hydrophilicity of the SA molecules, there will be limited or no aggregation of the ADC. The product is also checked by hydrophobic interaction chromatographic HPLC for the drug distribution (usually 2-4 drugs per antibody). ADC can also be fully reduced and then submitted to LC-MS analysis.

Example 37: Labeling Antibody with SA Molecule Labeled with Dox or SN38 Via Surface Amines Synthesis of 37FF1: 18 molar equiv. of 5-acetylvaleric NHS ester in 25 µL of DMSO is added to a centrifuge tube containing 0.45 mL of antibody (5 mg/mL) in 10 mM sodium phosphate, 10 mM NaCl, pH 8.0 buffer. The reaction is mixed at RT for 4 h, then passed through a NAP-5 column pre-equilibrated with 10 mM sodium phosphate, 10 mM NaCl, pH 6.0 buffer to remove the unreacted 5-acetylvaleric NHS ester and obtain the product.

Synthesis of 37FF2 and 37FF3: 35EE1 or 34EE1 (6 molar equiv.) is added to a centrifuge tube containing 2.25 mg of antibody in 1 mL 10 mM sodium phosphate, 10 mM NaCl, pH 6.0 buffer. The reaction is mixed at RT overnight. The unreacted 35EE1 or 34EE1 is removed by gel filtration. The final product is analyzed by size exclusion HPLC to check the aggregation profile. Due to the extreme hydrophilicity of the SA molecules, there will be limited or no aggregation of the ADC. The ADC can also be fully reduced and then submitted to LC-MS analysis.

Scheme 37

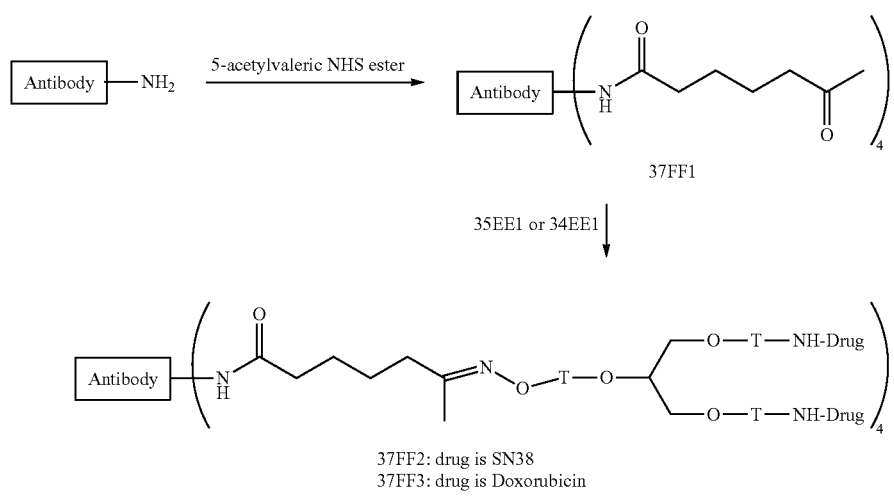

37FF2: drug is SN38
37FF3: drug is Doxorubicin

Example 38: Labeling SA Molecule Modified Antibody with Doxorubicin

Antibody (IgG, 3 mg) modified with several molecules of 20BB3 is buffer exchanged into 0.5 mL of 10 mM sodium phosphate, 10 mM NaCl, pH 6.0 buffer. 16 molar equiv. of doxorubicin in 25 µL of DMSO is added to the antibody solution. The reaction is mixed at RT for 4 h, then passed through a NAP-5 column pre-equilibrated with PBS buffer to remove the unreacted doxorubicin and obtain the product.

Example 39: Site-Specific Labeling Antibody with SA Molecule Labeled with Biotin or Fluorescein Antibody can be site-specifically loaded with multiple biotins or fluorescein dyes without aggregation following the same protocol as 36FF1 using 31EE5 and 31EE6 as labeling reagents.

Example 40: Labeling Antibody with SA Molecule Labeled with Biotin or Fluorescein Via Surface Amines Antibody can also be labeled at its surface amines with multiple biotins or fluorescein dyes without any aggregation following the same protocol as 37FF2 using 30EE1 or 30EE2 as the labeling reagents.

Example 41: Labeling Peptide with SA Molecule Labeled with Biotin or Fluorescein Via Cys A 15-mer peptide (3 mg) with a free Cys is dissolved in 0.1M sodium phosphate, 0.15M NaCl, 10 mM EDTA, pH 7.2 (reaction buffer) at a concentration of 10 mg/mL (total 300 µL). To this solution, 31EE5 or 31EE6 is added to a final concentration equal to 2 mole equivalents per mole of peptide. After reacting at RT for 2 h, the conjugate is purified by a C18 HPLC column using the standard TFA system for peptide.

Example 42: Labeling Oligo with SA Molecule Labeled with Biotin or Fluorescein Via Reduced Thiol A 15-mer oligo (3 mg) with 5' or 3' disulfide modifier is dissolved in 0.1M sodium phosphate, 0.15M NaCl, 10 mM EDTA, pH 7.2 (reaction buffer) at a concentration of 10 mg/mL (total 300 µL). To this solution, TCEP is added to a final concentration equal to 10 mole equivalents per mole of oligo. The solution is mixed at 37° C. for 1.5 h. Oligo is then precipitated out by ethanol and dissolved in 300 µL of reaction buffer. To this solution, 31EE5 or 31EE6 is added to a final concentration equal to 2 mole equivalents per mole of peptide. After reacting at RT for 2 h, the conjugate is purified by a C18 HPLC column using the standard TEAA system for oligo.

Example 43: Loading SA Molecule Modified Biotin onto Agarose Beads

Agarose beads containing thiol functional groups are readily available commercially and can be easily prepared by reacting amino agarose beads with succinimidyl 3-(2-pyridyldithio) propionate (SPDP). 4% cross-lined agarose beads (10 mL settle down beads) with disulfide groups are suspended in 20 mL of 0.1M sodium bicarbonate buffer, pH 9.0. 10 mL of TCEP (50 mg/ml) is added. The beads are stirred at 37° C. for 1 h before being transferred to a filtration setup with a Buchi Funnel. The beads are washed extensively with deionized water and then 20 mL of 0.1M sodium phosphate, 0.15M NaCl, 10 mM EDTA, pH 7.2 (reaction buffer). After washing, the beads are resuspended in 20 mL of reaction buffer and 10 mL of 20 mg/mL of 31BB5 solution in reaction buffer is added. After reacting at RT for 2 h, agarose beads are transferred to a filtration setup with a Buchi Funnel and the beads are washed extensively with deionized buffer to obtain the agarose beads with biotin attached.

Using SA linker, one can obtain biotin labeled agarose beads without much aggregation. Agarose beads with biotin loaded are useful for many biochemical experiments such as protein separation.

INCORPORATION BY REFERENCE

The entire disclosure of each of the publications and patent documents referred to herein is incorporated by reference in its entirety for all purposes to the same extent as if each individual publication or patent document were also individually denoted.

EQUIVALENTS

The invention may be embodied in other specific forms without departing from the spirit or essential characteristics thereof. The foregoing embodiments are therefore to be considered in all respects illustrative, rather than limiting, of the invention described herein. Thus, the scope of the invention is indicated by the appended claims rather than by the foregoing description, and all changes that come within the meaning and range of equivalent with the claims are intended to be embraced therein.

The invention claimed is:
1. A bifurcated SA monomer having a chemical structure of Formula I:

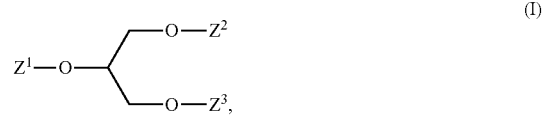

wherein
each of $Z^1$, $Z^2$, and $Z^3$ is independently selected from the group consisting of $R^{11}$,

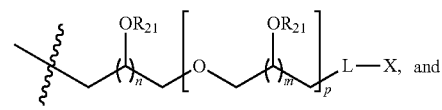

and

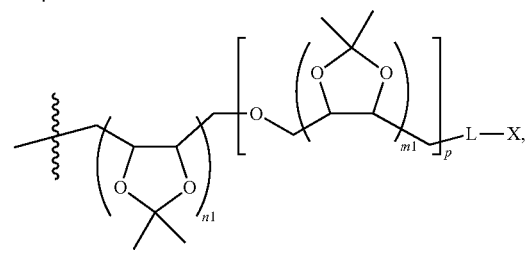

and at least one of $Z^1$, $Z^2$, and $Z^3$ is not $R^{11}$;

each $R^{11}$ is independently selected from the group consisting of acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methylthiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;

each $R^{21}$ is independently selected from the group consisting of hydrogen, acetyl, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methylthiomethyl ether, pivaloyl, tetrahydropyranyl, tetrahydrofuran, tetrahydrothiofuranyl, trityl, silyl ether, $C_1$-$C_8$ alkyl silyl, methyl ethers, ethoxyethyl ethers, $C_1$-$C_8$ alkyl, cyclic ortho ester, and acetonide of vicinal alcohol;

n is an integer selected from 2 to 8;
m is an integer selected from 1 to 8;
p is an integer selected from 0 to 50;
n1 is an integer selected from 1 to 4;
m1 is an integer selected from 1 to 4;

each L is independently selected from the group consisting of $R^2$ and a structure of —$V_1$—$R^2$—$V_2$—, wherein $V_1$ and $V_2$ are independently selected from the group consisting of a Diels-Alder adduct, a 1,3-dipolar adduct, —C($R^4$)(=N)—O—, —O—C($R^4$)(=N)—, —S—CH$_2$—C(=O)—NH—, —NH—C(=O)—CH$_2$—S—, —C(=$G^2$)-$G^1$-, -$G^1$-C(=$G^2$)-, -$G^3$-, -$G^1$-C(=$G^2$)-$G^1$-, —S—S—, —S—(CH$_2$)$_2$—S(O)$_2$—, —S(O)$_2$—(CH$_2$)$_2$—S—, —S(O)$_2$—N($R^3$)—, —N($R^3$)—S(O)$_2$—, —C(O)—NH—NH—CH$_2$—, —C(O)—NH—N=CH—, —CH=N—NH—C(O)—, —CH$_2$—NH—NH—C(O)—, —N($R^3$)—S(O)$_2$—N($R^3$)—, —C(O)—NH—CH(CH$_2$SH)—, —N=CH—, —NH—CH$_2$—, —NH—C(O)—CH$_2$—C(O)—NH—, —CH=N-$G^4$-, —CH$_2$—NH-$G^4$-, -$G^4$-NH—CH$_2$—, -$G^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—, wherein
each $G^1$ is independently selected from $NR^3$, O, and S;
each $G^2$ is independently O or S;
each $G^3$ is independently selected from S, O, $NR^3$, and SO$_2$;
each $G^4$ is independently O or $NR^3$;

each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, —CH$_2$—(CHOH)$_{1-6}$—, —(CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;

each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl, each $R^4$ is independently selected from $C_1$-$C_{16}$ alkyl, each X is independently selected from —OH, -J, —$R^5$J, —C(=O)-J, —C(=O)—CH$_2$-J, —NH—C(=O)—CH$_2$-J, —OR$^5$, —OR$^6$, —OR$^7$, —O-mesyl, —O-tosyl, —NH—C(=O)—CH$_2$—O-mesyl, —NH—C(=O)—CH$_2$—O-tosyl, —SH, —S—S-t-butyl, —SR$^7$, —SR$^5$, —S—S—R$^8$, —NH—C(=O)—R$^9$—S—S—R$^8$, —NH—C(=O)—CH$_2$—SH, —S(=O)$_2$-J, —NH—C(=O)—R$^9$—S—C(=O) R$^5$, —NH$_2$, —NHR$^5$, —N(R$^5$) R$^5$, —NHR$^7$, —NH-Fmoc, —NH-Boc, N-(phthalimidyl), —C(=O) H, —C(=O)—R$^5$, NH—C(=O)—R$^9$—C(=O)—R$^5$, —C(=O)OH, NH—C(=O)—R$^9$—C(=O)OH, —N=C=S, —N=C=O, —C≡C—R$^5$, —N=N$^+$=N$^-$, —O—NH$_2$, —O—NH-Fmoc, —O—NH-Boc, —O—N-(Boc)$_2$, —O—N(-phthalimidyl), —NH—C(=O)—R$^9$—O—NH-Boc, —NH—C(=O)—R$^9$—O—N-(Boc)$_2$, NH—C(=O)—R$^9$—O—N(-phthalimidyl), —NH—NH$_2$, —C(=O)—NH—NH$_2$, —NH—C(=O)—NH—NH$_2$, —NH—C(=S)—NH—NH$_2$, -toluenesulfonylhydrazide, —R$^5$—NH—C(=NH$_2^+$)—NH$_2$, —NH—C(=NH$_2^+$)—CH$_2$CH$_2$CH$_2$—SH,

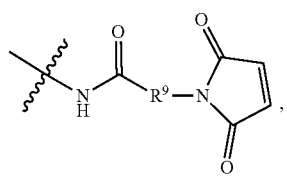

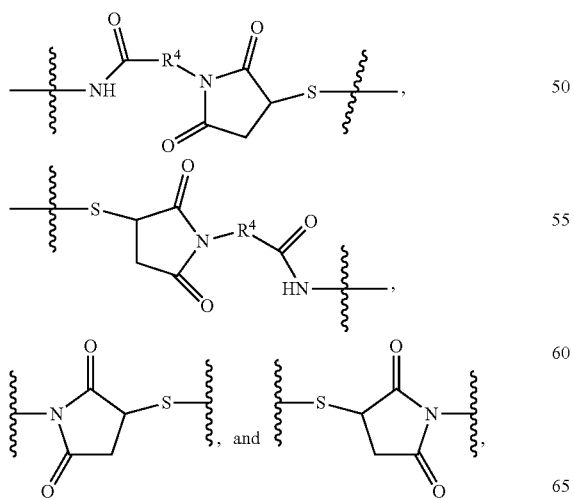

a benzophenone, an aryl diazonium, a diazoalkane, a diazoacetyl, an anthraquinone, a diazirine, an optionally substituted trifluoromethylphenyldiazirine, a diene, a dienophile, a 1,3-dipole, a dipolarophile, an alkene, a ketene, an alkene with allylic hydrogen, a dicarbonyl group, an epoxide, an oxirane, an organosilane, a phosphonium group, an ester, an anhydride, a carbonate group, a glyoxal, —C(=N$^+$H$_2$)—O—R$^5$, a hydroxymethyl phosphine, an ethyl vinyl, a maleimide, a vinylsulfone, an allyl sulfone, a thioester, a cisplatin, an aziridine, and an acryloyl group, wherein
- each $R^5$ is independently selected from optionally substituted $C_1$-$C_8$ alkyl, alicyclyl, heteroalicyclyl, benzyl, and aryl, wherein any ring in $R^5$ is optionally substituted;
- each $R^6$ is independently selected from benzoyl, acetyl, benzyl, $C_1$-$C_8$ alkyl silyl, tetrahydropyranyl, tetrahydrofuranyl, and tetrahydrothiofuranyl;
- each $R^7$ is independently selected from trityl, MMT, and DMT;
- each $R^8$ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
- each $R^9$ is independently selected from $C_1$-$C_{16}$ alkyl; and
- each J is independently selected from Cl, Br and I.

2. The monomer of claim 1, wherein $Z^2$ and $Z^3$ are $R^{11}$, $Z^1$ is a sugar alcohol linked group having a structure of

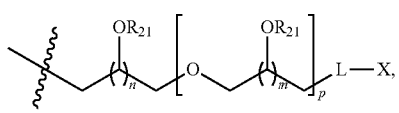

wherein n is an integer selected from 2 to 8, m is an integer selected from 1 to 8, and p is an integer selected from 0 to 8.

3. The monomer of claim 2, wherein L is a bond.

4. The monomer of claim 3, wherein each $R^{11}$ is independently selected from the group consisting of acetyl, benzoyl, benzyl, tetrahydropyranyl, trityl, and $C_1$-$C_8$ alkyl silyl.

5. The monomer of claim 4, wherein $R_{21}$ is independently selected from the group consisting of acetyl, benzoyl, benzyl, tetrahydropyranyl, trityl, and $C_1$-$C_8$ alkyl silyl, and an acetonide group of vicinal alcohol when there is more than one secondary OH group in a sugar alcohol.

6. The monomer of claim 5, wherein X of the $Z^1$ is —OBn.

7. The monomer of claim 3, wherein $R_{21}$ is acetyl and $R^{11}$ is TBDMS.

8. The monomer of claim 1, wherein each of $Z^1$, $Z^2$, and $Z^3$ is independently a sugar alcohol linked group having a structure of

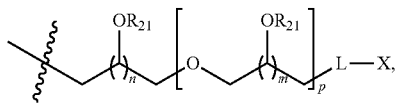

wherein $R_{21}$ is OH.

9. The monomer of claim 1, wherein $Z^2$, and $Z^3$ are $R^{11}$, $Z^1$ is a protected sugar alcohol linked group having a structure of

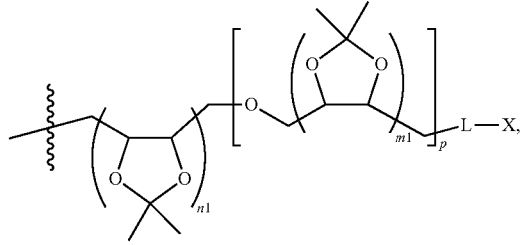

wherein n1 is an integer selected from 1 to 4, m1 is an integer selected from 1 to 4, and p is an integer selected from 0 to 8.

10. The monomer of claim 1, wherein each of $Z^1$, $Z^2$, and $Z^3$ is a protected sugar alcohol linked group having a structure of

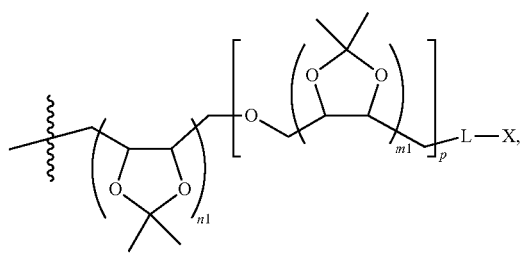

wherein n1 is an integer selected from 1 to 4, m1 is an integer selected from 1 to 4, and p is an integer selected from 0 to 50.

11. The monomer of claim 10, wherein p is an integer selected from 0 to 4.

12. The monomer of claim 11, wherein L is a bond.

13. The monomer of claim 12, wherein X of $Z^1$ is selected from OH, —NH—C(═O)—CH$_2$-J, —OR$^5$, —OR$^6$, —OR$^7$, —SH, —S—S-t-butyl, —SR$^5$, —S—S—R$^8$, —NH—C(═O)—R$^9$—S—S—R$^8$, —NH—C(═O)—CH$_2$—SH, —NH—C(═O)—R$^9$—S—C(═O)—R$^5$, —NH$_2$, —NH-Fmoc, —NH-Boc, N-(phthalimidyl), NH—C(═O)—R$^9$—C(═O)—R$^5$, NH—C(═O)—R$^9$—(═O)OH, —N═N$^+$═N$^-$, —O—NH$_2$, —O—NH-Fmoc, —O—NH-Boc, —O—N-(Boc)$_2$, —O—N(-phthalimidyl), —NH—C(═NH$_2^+$)—CH$_2$CH$_2$CH$_2$—SH, and

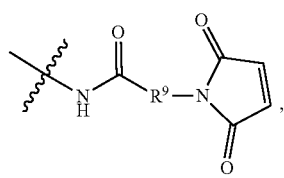

14. The monomer of claim 12, wherein X of $Z^2$ and $Z^3$ is the same and is selected from —OH, —NH—C(═O)—CH$_2$-J, —OR$^5$, —OR$^6$, —OR$^7$, —SH, —S—S-t-butyl, —SR$^5$, —S—S—R$^8$, —NH—C(═O)—R$^9$—S—S—R$^8$, —NH—C(═O)—CH$_2$—SH, —NH—C(═O)—R$^9$—S—C(═O)—R$^5$, —NH$_2$, —NH-Fmoc, —NH-Boc, N-(phthalimidyl), NH—C(═O)—R$^9$—C(═O)—R$^5$, NH—C(═O)—R$^9$—(═O)OH, —N═N$^+$═N$^-$, —O—NH$_2$, —O—NH-Fmoc, —O—NH-Boc, —O—N-(Boc)$_2$, —O—N(-phthalimidyl), —NH—C(═O)—R$^9$—O—NH-Boc, —NH—C(=O)—R$^9$—O—N-(Boc)$_2$, NH—C(=O)—R$^9$—O—N(-phthalimidyl), —NH—C(=NH$_2^+$)—CH$_2$CH$_2$CH$_2$—SH, and

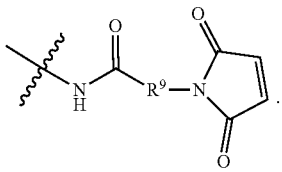

15. A bifurcated SA monomer having a chemical structure of Formula I:

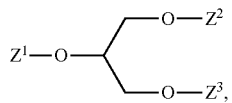

(I)

wherein
each of $Z^1$, $Z^2$, and $Z^3$ is independently selected from the group consisting of $R^{11}$ and

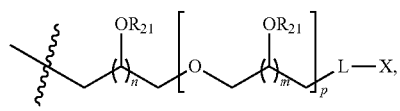

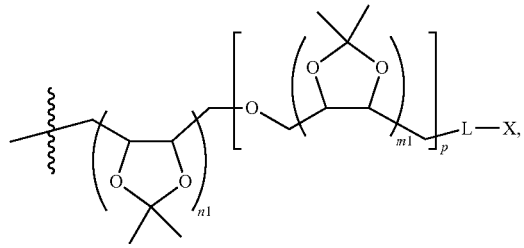

and at least one of $Z^1$, $Z^2$, and $Z^3$ is not $R^{11}$;
each $R^{11}$ is independently selected from the group consisting hydrogen, acetyl, acetate, benzoyl, benzyl, beta-methoxyethoxymethyl ether, dimethoxytrityl, methoxymethyl ether, methoxytrityl [(4-methoxyphenyl)diphenylmethyl], p-methoxybenzyl ether, methythiomethyl ether, pivaloyl, tetrahydropyranyl, tetrahydrofuran, tetrahydrothiofuranyl, trityl, silyl ether, $C_1$-$C_8$ alkyl silyl, methyl ethers, and ethoxyethyl ethers;
n1 is an integer selected from 1 to 4;
m1 is an integer selected from 1 to 4;
each L is independently selected from the group consisting of $R^2$ and a structure of —V$_1$—R$^2$—V$_2$—, wherein V$_1$ and V$_2$ are independently selected from the group consisting of a Diels-Alder adduct, a 1,3-dipolar adduct, —C(R$^4$)(=N)—O—, —O—C(R$^4$)(=N)—, —S—CH$_2$—C(=O)—NH—, —NH—C(=O)—CH$_2$—S—, —C(=G$^2$)-G$^1$-, -G$^1$-C(=G$^2$)-, -G$^3$-, -G$^1$-C(=G$^2$)-G$^1$-, —S—S—, —S—(CH$_2$)$_2$—S(O)$_2$—, —S(O)$_2$—(CH$_2$)$_2$—S—, —S(O)$_2$—N(R$^3$)—, —N(R$^3$)—S(O)$_2$—, —C(O)—NH—NH—CH$_2$—, —C(O)—NH—N=CH—, —CH=N—NH—C(O)—, —CH$_2$—NH—NH—C(O)—, —N(R$^3$)—S(O)$_2$—N(R$^3$)—, —C(O)—NH—CH(CH$_2$SH)—, —N=CH—, —NH—CH$_2$—, —NH—C(O)—CH$_2$—C(O)—NH—, —CH=N-G$^4$-, —CH$_2$—NH-G$^4$-, -G$^4$-NH—CH$_2$—, -G$^4$-N=CH—, —C(=NH$_2^+$)—NH—, —NH—C(=NH$_2^+$)—, —O—P(=O)(O$^-$)—NH—, —NH—P(=O)(O$^-$)—O—, —CH$_2$—CH(NH$_2$)—CH$_2$—S—, —S—CH$_2$—CH(NH$_2$)—CH$_2$—, —O—P(=O)(O$^-$)—O—, —O—P(=O)(S$^-$)—O—, —O—P(=S)(S$^-$)—O—,

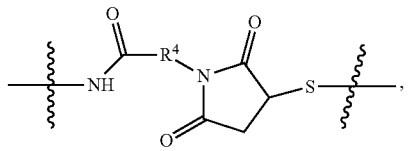

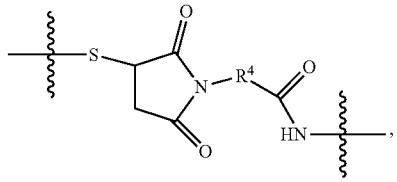

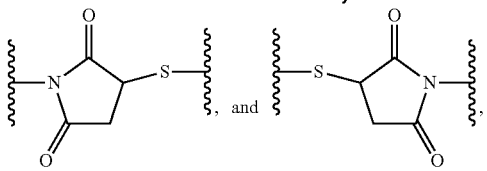, and wherein
each $G^1$ is independently selected from NR$^3$, O, and S;
each $G^2$ is independently O or S;
each $G^3$ is independently selected from S, O, NR$^3$, and SO$_2$;
each $G^4$ is independently O or NR$^3$;
each $R^2$ is independently selected from a bond, $C_1$-$C_{12}$ alkyl, —(CH$_2$CH$_2$O)$_{1-10}$—, —(CH$_2$CH$_2$O)$_{1-10}$—CH$_2$—, —CH$_2$—(CHOH)$_{1-6}$—, —(CHOH)$_{1-6}$—CH$_2$—, —(CHOH)$_{1-6}$—, optionally substituted alicyclyl, heteroalicyclyl, aryl, a peptide, p-aminobenzylcarbonyl spacer, a peptide with p-aminobenzylcarbonyl spacer, a dipeptide with p-aminobenzylcarbonyl spacer, and a peptidomimetic oligomer;
each $R^3$ is independently selected from hydrogen, $C_1$-$C_8$ alkyl, —(OCH$_2$CH$_2$)$_{1-3}$, optionally substituted alicyclyl, and optionally substituted heteroalicyclyl,
each $R^4$ is independently selected from $C_1$-$C_{16}$ alkyl,
each X is independently selected from —OH, -J, —R$^5$J, —C(=O)-J, —C(=O)—CH$_2$-J, —NH—C(=O)—CH$_2$-J, —OR$^5$, —OR$^6$, —OR$^7$, —O-mesyl, —O-tosyl, —NH—C(=O)—CH$_2$—O-mesyl, —NH—C(=O)—CH$_2$—O-tosyl, —SH, —S—S-t-butyl, —SR$^7$, —SR$^5$, —S—S—R$^8$, —NH—C(=O)—R$^9$—S—S—R$^8$, —NH—C(=O)—CH$_2$—SH, —S(=O)$_2$-J, —NH—C(=O)—R$^9$—S—C(=O) R$^5$, —NH$_2$, —NHR$^5$, —N(R$^5$) R$^5$, —NHR$^7$, —NH-Fmoc, —NH-Boc, N-(phthalimidyl), —C(=O) H, —C(=O)—R$^5$, NH—C(=O)—R$^9$—C(=O)—R$^5$, —C(=O)OH, NH—C(=O)—R$^9$—C(=O)OH, —N=C=S, —N=C=O, —C≡C—R$^5$, —N=N$^+$=N$^-$, —O—NH$_2$, —O—NH-Fmoc, —O—NH-Boc, —O—N-(Boc)$_2$, —O—N(-phthalimidyl), —NH—C(=O)—R⁹—O—NH-Boc, —NH—C(=O)—R⁹—O—N-(Boc)₂, NH—C(=O)—R⁹—O—N(-phthalimidyl), —NH—NH₂, —C(=O)—NH—NH₂, —NH—C(=O)—NH—NH₂, —NH—C(=S)—NH—NH₂, -toluenesulfonylhydrazide, —R⁵—NH—C(=NH₂⁺)—NH₂, —NH—C(=NH₂⁺)—CH₂CH₂CH₂—SH,

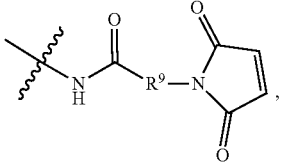

a benzophenone, an aryl diazonium, a diazoalkane, a diazoacetyl, an anthraquinone, a diazirine, an optionally substituted trifluoromethylphenyldiazirine, a diene, a dienophile, a 1,3-dipole, a dipolarophile, an alkene, a ketene, an alkene with allylic hydrogen, a dicarbonyl group, an epoxide, an oxirane, an organosilane, a phosphonium group, an ester, an anhydride, a carbonate group, a glyoxal, —C(=N⁺H₂)—O—R⁵, a hydroxymethyl phosphine, an ethyl vinyl, a maleimide, a vinylsulfone, an allyl sulfone, a thioester, a cisplatin, an aziridine, and an acryloyl group, wherein
each R⁵ is independently selected from optionally substituted C₁-C₈ alkyl, alicyclyl, heteroalicyclyl, benzyl, and aryl, wherein any ring in R⁵ is optionally substituted;
each R⁶ is independently selected from benzoyl, acetyl, benzyl, C₁-C₈ alkyl silyl, tetrahydropyranyl, tetrahydrofuranyl, and tetrahydrothiofuranyl;
each R⁷ is independently selected from trityl, MMT, and DMT;
each R⁸ is independently selected from 2-pyridyl, 4-pyridyl, 5-nitro-2-pyridyl, 5-nitro-4-pyridyl, 2-nitrophenyl, 4-nitrophenyl, 3-carboxy-4-nitrophenyl, and 2,4-dinitrophenyl;
each R⁹ is independently selected from C₁-C₁₆ alkyl; and
each J is independently selected from Cl, Br and I.

16. The monomer of claim 15, wherein L is a bond.
17. The monomer of claim 16, wherein each X is independently selected from OH, -J, —R⁵J, —C(=O)-J, —C(=O)—CH₂-J, —NH—C(=O)—CH₂-J, —OR⁵, —OR⁶, —OR⁷, —SH, —S—S-t-butyl, —SR⁵, —S—S—R⁸, —NH—C(=O)—R⁹—S—S—R⁸, —NH—C(=O)—CH₂—SH, —S(=O)₂-J, —NH—C(=O)—R⁹—S—C(=O)—R⁵, —NH₂, —NHR⁵, —N(R⁵) R⁵, —NH-Fmoc, —NH-Boc, N-(phthalimidyl), —C(=O) H, —C(=O)—R⁵, NH—C(=O)—R⁹—C(=O)—R⁵, —C(=O)OH, NH—C(=O)—R⁹—(=O)OH, —C≡C—R⁵, —N=N⁺=N⁻, —O—NH₂, —O—NH-Fmoc, —O—NH-Boc, —O—N-(Boc)₂, —O—N(-phthalimidyl), —NH—C(=O)—R⁹—O—NH-Boc, —NH—C(=O)—R⁹—O—N-(Boc)₂, NH—C(=O)—R⁹—O—N(-phthalimidyl), —NH—NH₂, —C(=O)—NH—NH₂, —NH—C(=O)—NH—NH₂, —NH—C(=S)—NH—NH₂, -toluenesulfonylhydrazide, —R⁵—NH—C(=NH₂⁺)—NH₂, —NH—C(=NH₂⁺)—CH₂CH₂CH₂—SH,

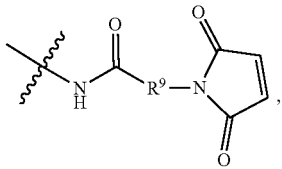

an aryl diazonium, a diazoalkane, a diazoacetyl, a diazirine, an optionally substituted trifluoromethylphenyldiazirine, an epoxide, a carbonate group, a glyoxal, —C(=NH₂)—O—R⁵, and a maleimide group.

18. The monomer of claim 16, wherein X of Z¹, Z², and Z³ is independently selected from OH, —NH—C(=O)—CH₂-J, —SH, —S—S-t-butyl, —SR⁵, —S—S—R⁸, —NH—C(=O)—R⁹—S—S—R⁸, —NH—C(=O)—CH₂—SH, —NH—C(=O)—R⁹—S—C(=O)—R⁵, —NH₂, —NHR⁵, —N(R⁵) R⁵, —NH-Fmoc, —NH-Boc, N-(phthalimidyl), —C(=O) H, —C(=O)—R⁵, NH—C(=O)—R⁹—C(=O)—R⁵, —C(=O)OH, NH—C(=O)—R⁹—(=O)OH, —O—NH₂, —O—NH-Fmoc, —O—NH-Boc, —O—N-(Boc)₂, —O—N(-phthalimidyl), —NH—C(=O)—R⁹—O—NH-Boc, —NH—C(=O)—R⁹—O—N-(Boc)₂, NH—C(=O)—R⁹—O—N(-phthalimidyl), —NH—C(=NH₂⁺)—CH₂CH₂CH₂—SH, and

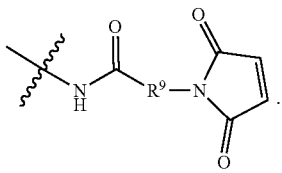

19. The monomer of claim 16, wherein X of Z¹ is independently selected from OH, —NH—C(=O)—CH₂-J, —SH, —S—S-t-butyl, —S—S—R⁸, —NH—C(=O)—R⁹—S—S—R⁸, —NH—C(=O)—CH₂—SH, —NH—C(=O)—R⁹—S—C(=O)—R⁵, —NH₂, —NH—C(=O)—R⁹—C(=O)—R⁵, —C(=O)OH, NH—C(=O)—R⁹—(=O)OH, —O—NH₂, —NH—C(=NH₂⁺)—CH₂CH₂—SH, and

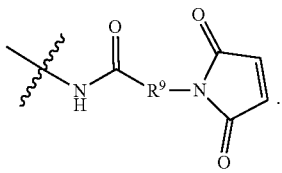

* * * * *